US007247634B2

(12) United States Patent
Ma et al.

(10) Patent No.: US 7,247,634 B2
(45) Date of Patent: Jul. 24, 2007

(54) RIFAMYCIN DERIVATIVES EFFECTIVE AGAINST DRUG-RESISTANT MICROBES

(75) Inventors: Zhenkun Ma, Dallas, TX (US); Yafei Jin, Dallas, TX (US); Jing Li, Dallas, TX (US); Charles Z. Ding, Plano, TX (US); Keith P. Minor, Dallas, TX (US); Jamie C. Longgood, Carrollton, TX (US); In Ho Kim, Flower Mound, TX (US); Susan Harran, Dallas, TX (US); Keith Combrink, Fort Worth, TX (US); Timothy W. Morris, Coppell, TX (US)

(73) Assignee: Cumbre Pharmaceuticals Inc., Dallas, TX (US)

( * ) Notice: Subject to any disclaimer, the term of this patent is extended or adjusted under 35 U.S.C. 154(b) by 228 days.

(21) Appl. No.: 11/034,195

(22) Filed: Jan. 12, 2005

(65) Prior Publication Data

US 2005/0261262 A1 Nov. 24, 2005

Related U.S. Application Data

(60) Provisional application No. 60/535,990, filed on Jan. 13, 2004.

(51) Int. Cl.
*C07D 498/08* (2006.01)
*A61K 31/395* (2006.01)
*A61P 31/04* (2006.01)

(52) U.S. Cl. .................. 514/253.04; 514/253.08; 514/278; 514/300; 514/312; 540/456

(58) Field of Classification Search ............ 540/456; 514/253.04, 253.08, 278, 300, 312
See application file for complete search history.

(56) References Cited

U.S. PATENT DOCUMENTS

| 3,738,980 | A | 6/1973 | Bickel |
| 4,179,438 | A | 12/1979 | Marchi et al. |
| 4,327,096 | A | 4/1982 | Marsili et al. |
| 5,180,718 | A | 1/1993 | Kump et al. |
| 5,786,350 | A | 7/1998 | Occelli et al. |

FOREIGN PATENT DOCUMENTS

| CH | 562831 | 6/1975 |
| GB | 1388880 | 3/1975 |
| WO | WO 02/09758 A2 | 2/2002 |
| WO | WO 03/045319 A2 | 6/2003 |
| WO | WO 03/084965 A1 | 10/2003 |

OTHER PUBLICATIONS

Brufani, M., Cerrini, S., Fedeli, W., Vaciago, Rifamycins: an Insight into Biological Activity Based on Structural Investigations, J. Mol. Biol. (1974) 87, 409-435.
Domagala, J. M. et al., Synthesis and Biological Activity of 5-Amino- and 5-Hydroxyquinolones, and the Overwhelming Influence of the Remote N1-Substituent in Determining the Structure-Activity Relationship, J. Med. Chem. 1991, 34, 1142-1154.
Sanchez, J. P. et al. Quinolone Antibacterial Agents. Synthesis and Structure-Activity Relationships of 8-Substituted Quinoline-3-carboxylic Acids and 1,8-Naphthyridine-3-carboxylic Acids, J. Med. Chem. 1988, 31, 983-991.
Farr, B. M., Rifamycins, Mandell, Douglas, and Bennett's Basic Principles and Practice in the Diagnosis and Management of Infection Diseases, 2000, Philadelphia; pp. 348-361.
Hutchinson, D. K., Oxazolidinone Atibacterial Agents: A Critical Review, Current Topics in Medicinal Chemistry, 2003, 3, 1021-1042.
Ince, D., Hooper, D.C., Mechanisms and Frequency of Resistance to Premafloxacin in *Staphylococcus aureus*: Novel Mutations Suggest Novel Drug-Target Interactions, Antimicrobial Agents and Chemotherapy, Dec. 2000, vol. 44, pp. 3344-3350.
Smith, P. W., et al, New Spiropiperidines as Potent and Selective Non-Peptide Tachykinin NK2 Receptor Antagonists, J. Med. Chem.; 1995; 38(19); 3772-3779.
Stender, W., et al., Studies of the Topography of the Binding Site of DNA-Dependent RNA Polymerase from *Escherichia coli* for the Antibiotic Rifamycin SV, Eur. J. Biochem.; 1977, 76, 591-600.
International Search Report and Written Opinion, European Patent Office, Jul. 27, 2005.

*Primary Examiner*—Bruck Kifle
(74) *Attorney, Agent, or Firm*—Jackson Walker L.L.P.

(57) ABSTRACT

Rifamycin derivatives having antimicrobial activities, including activities against drug-resistant microorganisms are claimed in this invention. The inventive rifamycin derivatives are uniquely designed in that they have a rifamycin moiety covalently linked to a linker group through the C-3 carbon of the rifamycin moiety and the linker is, in turn, covalently linked to a therapeutic moiety or antibacterial agent/pharmacophore. The therapeutic moiety can be a quinolone, an oxazolidinone, a macrolide, an aminoglycoside, a tetracycline core or a structure/pharmacophore associated with an antibacterial agent.

53 Claims, 14 Drawing Sheets

RIFAMYCIN DERIVATIVES EFFECTIVE AGAINST DRUG-RESISTANT MICROBES

BACKGROUND

"This application claims priority to U.S. Provisional Patent Application Ser. No. 60/535,990, entitled "RIFAMYCIN DERIVATIVES EFFECTIVE AGAINST DRUG-RESISTANT MICROBES" filed on Jan. 13, 2004, having Zhenkun Ma, Yafei Jin, Jing Li, Charles Z. Ding, Keith P. Minor, Jamie C. Longgood, and Timothy W. Morris, listed as the inventors, the entire content of which is hereby incorporated by reference."

This invention relates to a compound of rifamycin derivative having antimicrobial activities, its compositions, and methods for treatment and prevention of microbial infections. More particularly, the rifamycin derivative of the current invention is a rifanycin moiety covalently linked to a linker through the C-3 carbon of the rifamycin moiety and the linker is, in turn, covalently linked to a therapeutic moiety or antibacterial agent or pharmacophore. The inventive rifamycin derivatives are active against drug-resistant microorganisms with reduced frequency of developing mutational resistance in the microorganisms.

Rifamycins are natural products with potent antimicrobial activity. Examples of the naturally-occurring rifamycins are rifamycin B, rifamycin O, rifamycin R, rifamycin U, rifamycin S, rifamycin SV and rifamycin Y (Brufani, M., Cerrini, S., Fedeli, W., Vaciago, A. *J. Mol. Biol.* 1974, 87, 409-435). The therapeutic applications of the naturally-occurring rifamycins are limited due to their poor oral bioavailability, weak activity against Gram-negative pathogens and low distribution into the infected tissues. Significant efforts have been made toward identifying semi-synthetic rifamycin derivatives to address the deficiencies. As a result, many semi-synthetic rifamycin derivatives with improved spectrums and pharmacological profiles have been identified. Among the semi-synthetic compounds, rifampin, rifabutin and rifapetine have been developed into therapeutic agents and are widely used for the treatment of tuberculosis and other microbial infections (Farr, B. M. *Rifamycins*, in *Principles and Practice of Infectious Diseases*; Mandell, G. L., Bennett, J. E., Dolin, R., Eds.; Churchhill Livingstone: Philadelphia; p348-361).

At present, one of the major problems associated with the rifamycin class of antimicrobial agents is the rapid development of microbial resistance. Mutations in RNA polymerase are mainly responsible for the high frequency of microbial resistance to rifamycins. Consequently, rifamycins are currently used only in combination therapies with other antibiotics to minimize the development of resistance to this class of drug. Compounds of the current invention are designed to address the rifamycin resistance problem by covalently attaching another antibiotic pharmacophore to the C-3 position of the rifamycin molecules. The resulting rifamycin compounds of this invention exert their antimicrobial activity through dual or triple antibacterial mechanisms and therefore they exhibit reduced frequency of resistance.

Reference is made to U.S. Pat. No. 5,786,350 that discloses a series of C-36 derivatives of rifamycins, including derivatives formed by linking the C-3 carboxy group of a fluoroquinolone to the C-36 position of rifamycins through a chemically or metabolically labile ester group to deliver rifamycin and quinolone separately in vivo.

Reference is also made to PCT application WO 03/045319 A2 that discloses rifamycin derivatives formed by linking rifamycin and a therapeutic drug or antibacterial agent and the use of these derivatives as vehicles or pro-drugs for delivering the therapeutic drugs or antibacterial agents separately. However, this reference failed to demonstrate by specific examples that any drug is introduced to the C-3 position of a rifamycin molecule.

SUMMARY

One aspect of the current invention is a rifamycin compound having a Formula I:

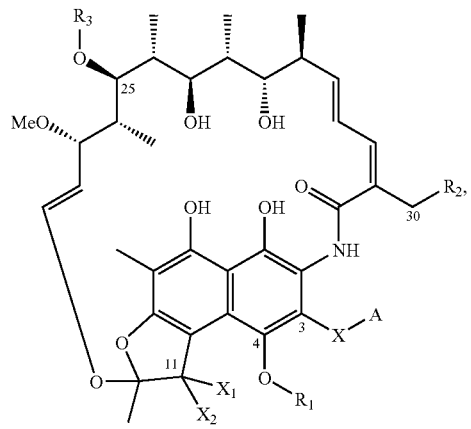

Formula I or its corresponding quinone form Formula II:

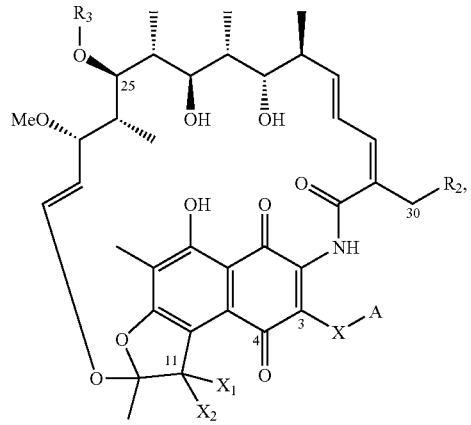

Formula II or its salt, hydrate, prodrug or a mixture thereof. In these Formulas, a therapeutic agent or its pharmacophore, such as an antibiotic, ("A") is covalently bonded or coupled to a rifamycin moiety, through a linker ("X"), to the C-3 carbon of the rifamycin core structure.

A preferred $R_1$ in the Formula I comprises: hydrogen, $(C_1-C_6)$alkyl, substituted $(C_1-C_6)$alkyl, —$CH_2COOH$, —$CH_2CONR_{11}R_{12}$; wherein, $R_{11}$ and $R_{12}$ independently represent hydrogen, $(C_1-C_6)$alkyl, substituted $(C_1-C_6)$alkyl; or $R_{11}$ and $R_{12}$ can join together with the nitrogen atom to which they are attached to form a 4- to 8-membered heterocyclic ring, optionally containing one additional heteroatom selected from O, N or S, wherein one of the carbon or nitrogen atoms is optionally substituted by a $(C_1-C_6)$alkyl or substituted $(C_1-C_6)$alkyl.

A preferred $R_2$ comprises hydrogen or hydroxyl group.

A preferred $R_3$ comprises hydrogen, acetyl, or —$COCH_2R_{21}$, wherein, $R_{21}$, represents hydrogen, halogen, hydroxyl, thio, amino, $(C_1-C_6)$alkoxy, $(C_1-C_6)$alkylthio, $(C_1-C_6)$acyloxy, $(C_1-C_6)$alkylamino, di$(C_1-C_6)$alkylamino, or heterocyclo group.

In the above Formulas I and II, one of $X_1$ and $X_2$ is a hydrogen and another is a hydroxyl. In a preferred embodiment, $X_1$, $X_2$ and the carbon atom to which they are attached join together to form a carbonyl.

In the preferred embodiments, the linkage group between "A" and rifamycin is not an imino (—C(H)=N—) group directly bonded to the C-3 position of the rifamycin moiety or its corresponding quinone form.

Preferred sets of linkers ("X") are shown in FIGS. 1, 4, and 6, where the left side of the linker is attached to the C-3 carbon of rifamycin molecule through a C—N or C—C bond, and the right side of the linker is attached to the quinolone core structure or its pharmacophore through a C—N or C—C bond.

The therapeutic drug or antibacterial agent "A" can be a quinolone, an oxazolidinone, a macrolide, an aminoglycoside, a tetracycline, and the like, or their antibacterial pharmacophores.

A preferred therapeutic molecule ("A") comprises Formula III and Formula IV,

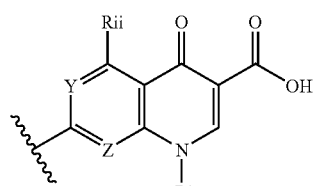

III

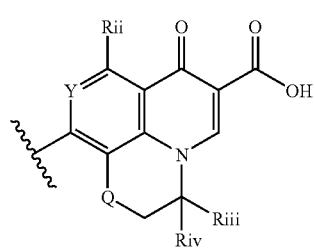

IV wherein, Ri comprises: $(C_1-C_6)$alkyl, $(C_3-C_6)$cycloalkyl, substituted $(C_3-C_6)$cycloalkyl, aryl, substituted aryl, heteroaryl, or substituted heteroaryl; Rii comprises hydrogen, halogen, amino, nitro or methyl group; Riii and Riv independently comprise hydrogen, $(C_1-C_6)$alkyl; or Riii and Riv join together with the carbon atom to which they are attached to form a 3- to 6-membered ring; Y represents C—H, C—F, or N; Z represents C—H, C—F, C—CN, C—$CF_3$, C—Cl, C-Me, C—OMe, C—$OCH_2F$, C—$OCHF_2$, or N; and Q represents $CH_2$, O or S. A specific therapeutic molecule ("A") may comprise any of the structural formulas related to quinolones shown in FIG. 5. The preferred therapeutic quinolone molecules ("A"), as shown in FIG. 5 described above are covalently coupled or bonded at the indicated or C-7 carbon of the quinolone core structure to the linker "X" which in turn is covalently coupled or bonded to the C-3 carbon of the rifamycin moiety.

Another preferred therapeutic molecule ("A") comprises the structural formulas of the macrolide antibiotics, as shown below:

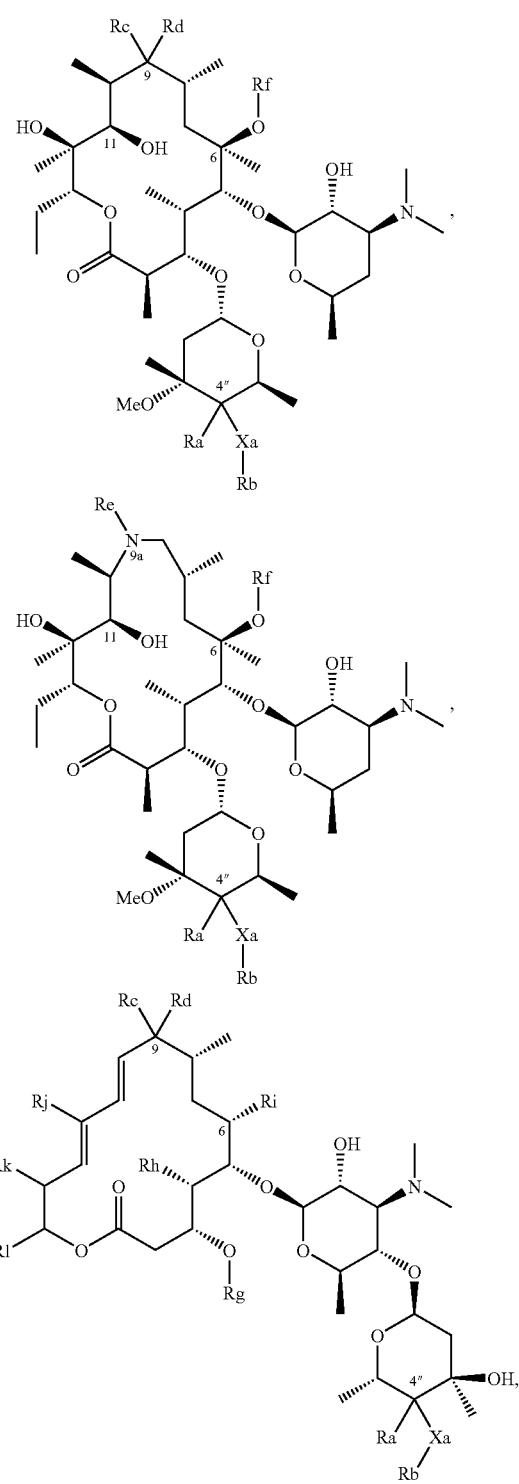

wherein, Ra is hydrogen or hydroxyl; Xa is —O—, —NH—, or —$CH_2NH$—; Rb is —X—Rx, wherein X is absent or the linker group described above; Rx comprises ($C_1$-$C_6$)alkyl, substituted ($C_1$-$C_6$)alkyl, aryl, substituted aryl, heteroaryl or substituted heteroaryl, or Rx represents a rifamycin structure; one of Rc and Rd is a hydrogen atom and another is selected from hydroxyl, amino-, alkylamino, dialkylamino, —NH—X—Rx, or Rc and Rd together with the carbon atom to which they are attached to form a C=O or C=N—O—X—Rx; Re is ($C_1$-$C_6$)alkyl, substituted ($C_1$-$C_6$)alkyl, or —X—Rx; Rf is hydrogen, ($C_1$-$C_6$)alkyl, or substituted ($C_1$-$C_6$)alkyl; Rg is hydrogen, acetyl or propionyl group; $R_h$ is methyl or methoxyl group; Ri is —$CH_2$CHO, —$CH_2$CH=N—O—X—Rx, —$CH_2$$CH_2$—NH—X—Rx; Rj is hydrogen or methyl; Rk is hydrogen or —$CH_2$—O-sugar; and R1 is methyl or ethyl. A specific set of therapeutic molecules "A" are represented in the structural formulas shown in FIG. 3. The preferred therapeutic macrolide molecules ("A"), as shown in FIG. 3 described above are covalently coupled to the linker "X" or coupled directly to the C-3 carbon of the rifamycin moiety through any one of C-4", C-6, C-9, or C-9a position of the macrolide. Preferred sets of linkers ("X") are shown in FIG. 4, where the left side of the linker is attached to the C-3 carbon of rifamycin molecule through a C—N or C—C bond and the right-hand side of the linker is attached to the macrolide molecule through a C—N or C—O bond.

Another aspect of the current invention comprises a method of treating a microbial infection in a subject; wherein the subject is any species of the animal kingdom. The microbial infection can be caused by a bacterium or microorganism. The term "subject" refers more specifically to human and animals, wherein the animals are raised for: pets (e.g. cats, dogs, etc.); work (e.g. horses, cows, etc.); food (chicken, fish, lambs, pigs, etc); and all others known in the art. The method comprises administering an effective amount of one or more compounds of the present invention to a subject suffering from microbial infection. The compounds of the current invention are effective against drug-resistant microbes and, in particular, against rifamycin-resistant microbes.

DETAILED DESCRIPTION

Figure 1:
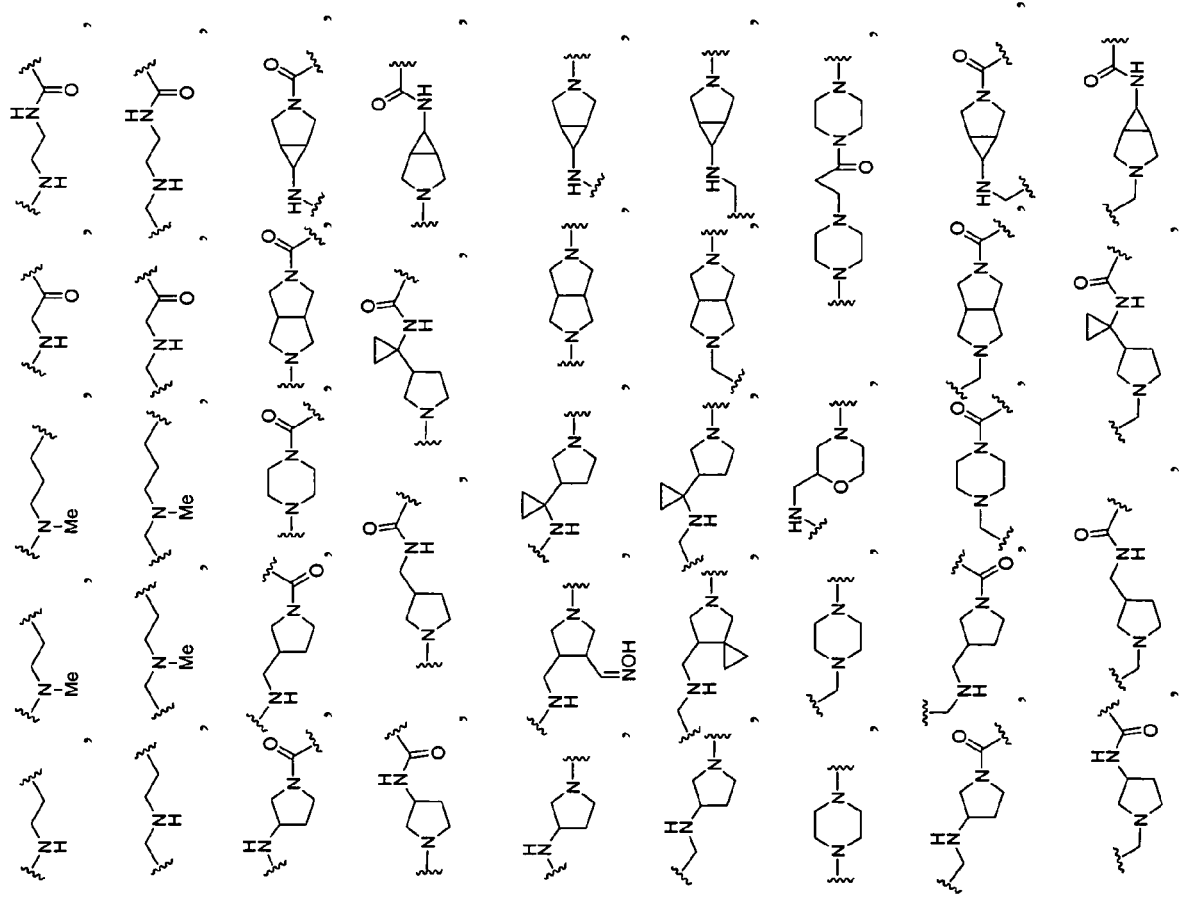
FIG. 1 shows a group of "universal" linkers.

Terms:

The term "alkenyl," as used herein, refers to a monovalent straight or branched chain group containing at least one carbon-carbon double bond. The alkenyl groups of this invention can be optionally substituted.

The term "alkenylene," as used herein, refers to a bivalent straight or branched chain group containing at least one carbon-carbon double bond. The alkenylene groups of this invention can be optionally substituted.

The term "alkyl," as used herein, refers to a monovalent, saturated, straight or branched chain hydrocarbon group. Examples of alkyl group include methyl, ethyl, propyl, iso-propyl, n-butyl, iso-butyl, tert-butyl, neo-pentyl, and n-hexyl. The alkyl groups of this invention can be optionally substituted.

The term "alkylene," as used herein, refers to bivalent saturated, straight or branched chain hydrocarbon structures. Examples of alkylene groups include methylene, ethylene, propylene, iso-propylene, n-butylene, isobutylene, and n-hexylene. The alkylene groups of this invention can be optionally substituted.

The term "alkylamino," as used herein, refers to an amino group (—$NH_2$), wherein one hydrogen atom is replaced by an alkyl group. Examples of alkylamino include methylamino, ethylamino, propylamino, and isopropylamino.

The term "alkylthio," as used herein, refers to an alkyl group, as defined herein, attached to the parent molecular group through a sulfur atom. Examples of alkylthio include methylthio, ethylthio, propylthio, and isopropylthio.

The term "alkoxy," as used herein, refers to an alkyl group, as previously defined, attached to the parent molecular group through an oxygen atom. Examples of alkoxy include methoxy, ethoxy, propoxy, iso-propoxy, n-butoxy, tert-butoxy, neo-pentoxy and n-hexoxy. The alkoxy groups of this invention can be optionally substituted.

The term "alkynyl," as used herein, refers to a monovalent straight or branched chain group of two to six carbon atoms containing at least one carbon-carbon triple bond. Examples of alkynyl include ethynyl, propynyl, and butynyl. The alkynyl groups of this invention can be optionally substituted.

The term "alkynylene," as used herein, refers to a bivalent straight or branched chain group of two to six carbon atoms containing at least one carbon-carbon triple bond. Examples of alkynylene include ethynylene, propynylene, and butynylene. The alkynylene groups of this invention can be optionally substituted The term "aprotic solvent," as used herein, refers to a solvent that is relatively inert to protonic activity, i.e., not acting as a proton donor. Examples include hexane, toluene, dichloromethane, ethylene dichloride, chloroform, tetrahydrofuran, N-methylpyrrolidinone, and diethyl ether.

The term "aryl" as used herein refers to a monovalent carbocyclic aromatic group such as phenyl, naphthyl, and anthracenyl, which can be optionally substituted.

The term "arylene" as used herein refers to bivalent carbocyclic aromatic groups which can be optionally substituted.

The term "benzyl," as used herein, refers to —$CH_2$$C_6$$H_5$.

The term "benzyloxy," as used herein, refers to a benzyl group, as defined herein, attached to the parent molecular group through an oxygen atom.

The term "carboxaldehyde," as used herein, refers to —CHO.

The term "cycloalkyl," as used herein, refers to a monovalent saturated carbocyclic group having three to eight carbons such as cyclopropyl, cyclobutyl, cyclopentyl, cyclohexyl, cycloheptyl and cyclooctyl.

The term "cycloalkylene," as used herein, refers to bivalent saturated carbocyclic groups having three to eight carbons. The cycloalkylene groups can be optionally substituted.

The term "formyl," as used herein, refers to —CH(=O).

The term "halogen," as used herein, refers to fluorine, chlorine, bromine and iodine atoms and the term "halo" refers to —F, —Cl, —Br, and —I as substituent.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. Heteroaryl groups of this invention include those derived from furan, imidazole, isothiazole, isoxazole, oxazole, pyrazine, pyrazole, pyridazine, pyridine, pyrimidine, pyrrole, quinoline, thiazole, 1,3,4-thiadiazole, triazole, and tetrazole.

The term "heteroarylene," as used herein, refers to a bivalent cyclic aromatic group having five or six ring atoms wherein at least one ring atom is selected from the group consisting of oxygen, sulfur, and nitrogen, and the remaining ring atoms are carbon. The heteroarylene group can be optionally substituted.

The term "heteroatom," as used herein, refers to oxygen, nitrogen or sulfur atom.

The term "heterocycloalkyl" as used herein, refers to a non-aromatic five-, six- or seven-membered ring or a bi- or tri-cyclic group having one or more heteroatoms independently selected from oxygen, sulfur, and nitrogen, wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to an aryl or heteroaryl ring. Representative heterocycles include, but are not limited to: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, morpholinyl, isothiazolidinyl, and tetrahydrofurranyl. The heterocycloalkyl groups of this invention can be optionally substituted with one, two, or three substituents independently selected from —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -cycloheteroalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, and -methylthiomethyl.

The term "heterocycloalkylene" as used herein, refers to a bivalent non-aromatic five-, six- or seven-membered ring having one or more heteroatoms independently selected from oxygen, sulfur and nitrogen wherein each 5-membered ring has zero to one double bonds and each six-membered ring has zero to 2 double bonds. The heterocycloalkylene groups of this invention can be optionally substituted.

The term "hydrate" as used herein, refers to a molecule that has been hydrated, or reacted with water in a hydration reaction. In a hydration reaction, molecules of water react with a compound, but the H—OH bond is not split. The water is usually split off from the hydrated compound by heat, yielding the anhydrous compound.

The term "hydroxyl," as used herein, refers to —OH.

The term "protecting group", as used herein, refers to an easily removable group to which are known in the art to protect a functional group, such as hydroxyl and amino, against undesirable reaction during synthetic procedures and to be selectively removable. The use of protecting groups is well-known in the art for protecting groups against undesirable reactions during a synthetic procedure and many such protecting groups are known (T. H. Greene and P. G. M. Wuts, Protective Groups in Organic Synthesis, 2nd edition, John Wiley & Sons, New York, 1991).

The term "pharmaceutically acceptable prodrugs," as used herein refers to the prodrugs of the compounds of the current invention which are suitable for use in humans and animals with acceptable toxicity, irritation, allergic response, and the like, commensurate with a reasonable benefit to risk ratio, and effective for their intended use.

The term "pharmaceutically acceptable salt," as used herein refers to those salts which are suitable for use in humans and animals with acceptable toxicity, irritation, and allergic response, etc., and are commensurate with a reasonable benefit to risk ratio. Pharmaceutically acceptable salts are well known in the art. The salts can be prepared in situ during the final step of isolation and purification of the compounds of the invention or separately prepared by reacting the compounds of the invention with an acid or base. Examples of pharmaceutically acceptable salts are salts of an amino group formed with inorganic acids such as hydrochloric acid, hydrobromic acid, phosphoric acid, and sulfuric acid or with organic acids such as acetic acid, oxalic acid, maleic acid, tartaric acid, citric acid, succinic acid, or malonic acid. Examples of pharmaceutically acceptable salts include salts of an acid group formed with inorganic bases such as sodium hydroxide, sodium carbonate, sodium phosphate, etc. Other metal salts include lithium, potassium, calcium, and magnesium. Additional pharmaceutically acceptable salts include ammonium cations formed with counterions such as halide, hydroxide, carboxylate, sulfate, phosphate, nitrate, loweralkyl sulfonate, and aryl sulfonate.

The term "pharmaceutically acceptable carrier," as used herein, refers to a non-toxic, inert solid, semi-solid or liquid filler, diluent, encapsulating material or formulation auxiliary of any type. Some examples of materials which can serve as pharmaceutically acceptable carriers include carbohydrates such as lactose, glucose and sucrose; starches such as corn starch and potato starch; cellulose and its derivatives such as sodium carboxymethyl cellulose, ethyl cellulose and cellulose acetate; glycols; such a propylene glycol; esters such as ethyl oleate and ethyl laureate; agar; buffering agents such as magnesium hydroxide and aluminum hydroxide; alginic acid; pyrogen-free water; isotonic saline; Ringer's solution; ethyl alcohol, and phosphate buffer solutions, as well as other nontoxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically, bucally, or as an oral, or nasal spray.

The term "pharmacophore", as used herein, refers to a structural element in a drug or bioactive molecule that is critical for biological interaction to its biological target and its subsequent biological effects. For example, for fluoroquinolone antibiotics, such as ciprofloxacin, its pharmacophore is 4-quinolone-3-carboxylic acid structural element The term "prodrug," as used herein, represents compounds which can be transformed in vivo to the active parent compounds defined herein.

The term "rifamycin moiety," as used herein, comprises both its phenolic and quinone forms of the rifamycin core structure (ansa-chain and naphthalene ring).

The term "substituted aryl" as used herein refers to an aryl group as defined herein, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heteroaryl" as used herein refers to a heteroaryl group as defined herein substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituted heterocycloalkyl," as used herein, refers to a heterocycloalkyl group, as defined above, substituted by independent replacement of one, two or three of the hydrogen atoms with —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

The term "substituent," as used herein, refer to —F, —Cl, —OH, —NO$_2$, —CN, —C(O)-alkyl, —C(O)-aryl, —C(O)-heteroaryl, —CO$_2$-alkyl, —CO$_2$-aryl, —CO$_2$-heteroaryl, —C(O)NH$_2$, —C(O)NH-alkyl, —C(O)NH-aryl, —C(O)NH-heteroaryl, —OC(O)-alkyl, —OC(O)-aryl, —OC(O)-heteroaryl, —OC(O)NH$_2$, —OC(O)NH-alkyl, —OC(O)NH-aryl, —OCONH-heteroaryl, —NHC(O)-alkyl, —NHC(O)-aryl, —NHC(O)-heteroaryl, —NHCO$_2$-alkyl, —NHCO$_2$-aryl, —NHCO$_2$-heteroaryl, —NHC(O)NH$_2$, —NHC(O)NH-alkyl, —NHC(O)NH-aryl, —NHC(O)NH-heteroaryl, —SO$_2$-alkyl, —SO$_2$-aryl, —SO$_2$-heteroaryl, —SO$_2$NH$_2$, —SO$_2$NH-alkyl, —SO$_2$NH-aryl, —SO$_2$NH-heteroaryl, -alkyl, -cycloalkyl, -heterocycloalkyl, —CF$_3$, —CH$_2$OH, —CH$_2$NH$_2$, -aryl, -heteroaryl, -benzyl, -benzyloxy, -aryloxy, -heteroaryloxy, -alkoxy, -methoxymethoxy, -methoxyethoxy, -amino, -benzylamino, -arylamino, -heteroarylamino, -alkylamino, -thio, -arylthio, -heteroarylthio, -benzylthio, -alkylthio, or -methylthiomethyl.

Abbreviations:

Abbreviations as used herein have the meanings known by one skilled in the art. Specifically, Ac represents acetyl group, AOC represents allyloxycarbonyl group, BOC represents t-butoxycarbonyl group, Bn represents benzyl group, Bu represents butyl group, Bz represents benzoyl group, Cbz represents benzyloxycarbonyl group, CDI represents carbonyldiimidazole, DCM represents dichloromethane, DMAP represents 4-N,N-dimethylaminopyridine, DME represents 1,2-dimethoxyethane, DMF represents N,N-dimethylformamide, DMSO represents dimethyl sulfoxide, Et represents ethyl group, EtOAc represents ethyl acetate, Me represents methyl group, MEM represents 2-methoxyethoxymethyl group, MOM represents methoxyl methyl group, NMP represents N-methylpyrrolidinone, Ph represents phenyl group, Pr represents propyl group, TEA represents triethylamine, TFA represents trifluoroacetic acid, THF represents tetrahydrofuran, TMS, trimethylsilyl group, and Ts represents p-toluenesulfonyl group.

Broadly, one aspect of the present invention comprises a rifamycin compound having a formula:

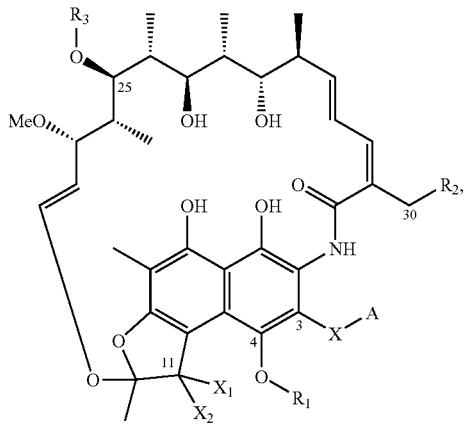

or its corresponding quinone form:

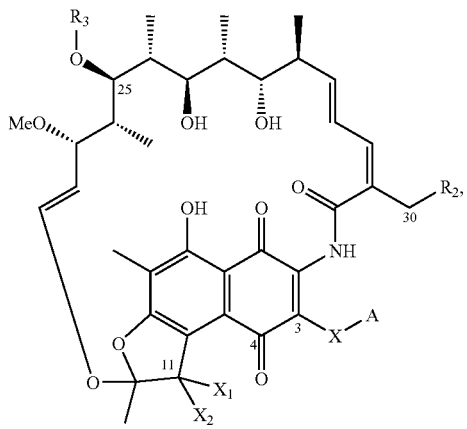

or its salt, hydrate, prodrug or a mixture thereof;
wherein,
A is an antibacterial agent or its pharmacophore covalently coupled to a linker ("X"), wherein A comprises an antibiotic, such as, a quinolone, a macrolide, an oxazolidinone, an aminoglycoside, or a tetracycline core structure and the like;
X is a linker group that is covalently coupled to both rifamycin on one side and antibiotic "A" on the other, wherein "X" comprises any combination of 1 to 5 of the following structural elements:
a) —($C_1$-$C_6$)alkylene,
b) —($C_1$-$C_6$)alkenylene,
c) —($C_1$-$C_6$)alkynylene,
d) —($C_3$-$C_8$)cycloalkylene,
e) —O—,
f) —C(H)=—,
g) —C(=O)—,
h) —C(=N—O—$R_{13}$)—, wherein $R_{13}$ represents hydrogen, ($C_1$-$C_6$)alkyl, substituted ($C_1$-$C_6$)alkyl,
i) —S(O)$_n$—, wherein n is 0, 1, or 2,
j) —N($R_{14}$)—, wherein $R_{14}$ represents hydrogen, ($C_1$-$C_6$)alkyl, substituted ($C_1$-$C_6$)alkyl;
k) arylene,
l) heteroarylene, and
m) bivalent heterocyclic structure containing 1 to 3 heteroatoms,
wherein, the carbon or nitrogen atoms of the linker group "X" can be optionally substituted by 1 to 3 substituents selected from ($C_1$-$C_6$)alkyl, substituted ($C_1$-$C_6$)alkyl, heterocycloalkyl, amino, ($C_1$-$C_6$)alkylamino, di($C_1$-$C_6$)alkylamino, hydroxyl, or ($C_1$-$C_6$)alkoxy;
$R_1$ comprises: hydrogen, ($C_1$-$C_6$)alkyl, substituted ($C_1$-$C_6$)alkyl, —$CH_2COOH$, —$CH_2CONR_{11}R_{12}$; wherein, $R_{11}$ and $R_{12}$ independently represent hydrogen, ($C_1$-$C_6$)alkyl, substituted ($C_1$-$C_6$)alkyl; or $R_{11}$ and $R_{12}$ join together with the nitrogen atom to which they are attached to form a 4- to 8-membered heterocyclic ring, optionally containing one additional heteroatom selected from O, N or S, wherein one of the carbon or nitrogen atoms is optionally substituted by a ($C_1$-$C_6$)alkyl or substituted ($C_1$-$C_6$)alkyl;
$R_2$ comprises hydrogen or hydroxyl group;
$R_3$ comprises hydrogen, heterocyclic group, or —$COCH_2R_{21}$, wherein, $R_{21}$ represents hydrogen, halogen, hydroxyl, thio, amino, ($C_1$-$C_6$)alkoxyl, ($C_1$-$C_6$)alkylthio, ($C_1$-$C_6$)acyloxy, ($C_1$-$C_6$)alkylamino, di($C_1$-$C_6$)alkylamino or heterocyclic group; and
one of $X_1$ and $X_2$ is a hydrogen and another is a hydroxyl; or $X_1$, $X_2$ and the carbon atom to which they are attached join together to form a carbonyl (>C=O).

The compounds of Formulas I and II may form salts which are also within the scope of this invention. Reference to a compound of Formulas I and II herein is understood to include reference to salts thereof, unless otherwise indicated. The term "salt(s)," as employed herein, denotes acidic and/or basic salts formed with inorganic and/or organic acids and bases. In addition, when a compound of Formulas I and II contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of Formulas I and II may be formed, for example, by reacting a compound of Formula I and II with an amount of acid or base, such as an equivalent amount, in a medium such as one in which the salt precipitates or in an aqueous medium followed by lyophilization.

The compounds of Formula I and II which may contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of Formula I and II which may contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), arylalkyl halides (e.g., benzyl and phenethyl bromides), and others.

Compounds of Formulas I and II, and salts thereof, may exist in their tautomeric form (for example, as an amide or imino ether). All such tautomeric forms are contemplated herein as part of the present invention.

All stereoisomers of the present compounds, such as those, for example, which may exist due to asymmetric carbons, including enantiomeric forms (which may exist even in the absence of asymmetric carbons) and diastereomeric forms, are contemplated and within the scope of this invention. Individual stereoisomers of the compounds of this invention may, for example, be substantially free of other isomers, or may be admixed, for example, as racemates or with all other or other selected, stereoisomers. The chiral centers of the present invention can have the S or R configuration as defined by the IUPAC 1974 Recommendations.

In addition, compounds of Formulas I and II may be present in prodrug forms. Any compound that will be converted in vivo to provide the bioactive agent (i.e., a compound of Formula I and II) is a prodrug which is within the scope and spirit of the invention.

For example, pro-drug compounds of Formulas I and II may be carboxylate ester moieties. A carboxylate ester may be conveniently formed by esterifying any of the carboxylic acid functionalities found on the disclosed ring or chain structure(s).

Compositions:

The compounds of the current invention are rifamycin derivatives of Formula I and Formula II, which have been labeled at the C-3, C-4, C-11, C-25 and C-30 positions of the rifamycin structure for illustration purposes. Formula I and Formula II are different in their oxidation states and can be transformed from one to another by utilizing an oxidation or reduction reaction. In one aspect, compounds of the current invention contain 9 asymmetric and 3 geometric centers. In some cases, one or more of the asymmetric or geometric centers can be converted to their opposite configurations. These stereoisomers of rifamycin are within the scope of the present invention.

EXAMPLE 1

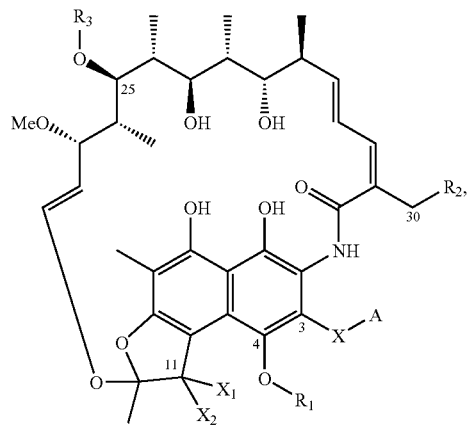

Formula I or its quinone form Formula II

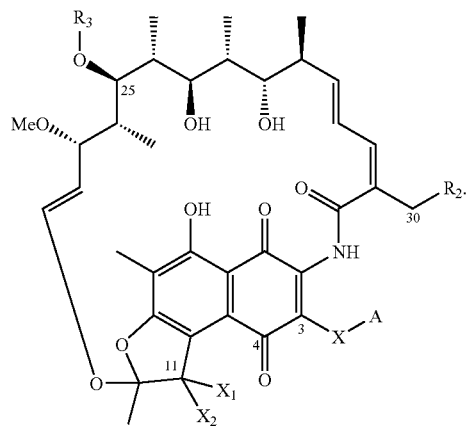

Formula II $R_1$ group in Formula I can be a hydrogen atom and the molecule is in the same oxidation state as that of rifamycin SV. $R_1$ can also be a lower alkyl or substituted lower alkyl group of between 1 to 6 carbon atoms. The C-4 position of rifamycins can tolerate a substituent group, these compounds may have activity against microorganisms. In addition, $R_1$ can be a —$CH_2COOH$, or a —$CH_2C(O)NR_{11}R_{12}$ group. Compounds with these substituents can be conveniently derived from rifamycin B, although they can be prepared from other rifamycin compounds as well. The structure of the amide group —$C(O)NR_{11}R_{12}$ herein can be varied from a simple amide, wherein $R_{11}$ and $R_{12}$ are both hydrogen atoms to more complex structure, wherein either one or both $R_{11}$ and $R_{12}$ independently are lower alkyl groups between 1 to 6 carbon atoms, where the alkyl groups can be substituted by a variety of substituent groups. Examples of the substituent groups include alkyl, substituted alkyl, amino, alkylamino, dialkylamino, hydroxyl, alkoxy, or halogens. Furthermore, $R_{11}$ and $R_{12}$ together with the nitrogen atom to which they are attached can form a 4- to 8-membered heterocyclic ring. This ring can optionally contain one additional heteroatom selected from oxygen, nitrogen and sulfur, wherein one of the carbon or nitrogen atoms is optionally substituted by a lower alkyl or substituted lower alkyl group.

$R_2$ represents a group attached to the C-30 position that can be a hydroxyl group or a hydrogen. In the preferred embodiment, $R_2$ is a hydrogen atom.

$R_3$ group of the current invention represents a hydrogen, an acetyl or a substituted acetyl group of formula —C(O)CH$_2$R$_{21}$. In their natural form, rifamycins have an acetyl group at the C-25 position. Chemical or enzymatic hydrolysis of the acetyl group provides the de-acetylated compounds wherein $R_3$ is a hydrogen atom. The de-acetylated compounds can be further transformed to compounds where $R_3$ is a group of formula —C(O)CH$_2$R$_{21}$. $R_{21}$ can be a variety of groups such as halogen, hydroxyl, thio, amino, (C$_1$-C$_6$)alkoxy, (C$_1$-C$_6$)alkylthio, (C$_1$-C$_6$)acyloxy, (C$_1$-C$_6$)alkylamino, di(C$_1$-C$_6$)alkylamino, or a heterocyclic group.

One of $X_1$ and $X_2$ is hydrogen and another is hydroxyl. In the preferred embodiment for the practice of the invention, $X_1$ and $X_2$ together with the carbon atom they are attached to form a carbonyl group.

Figure 4:
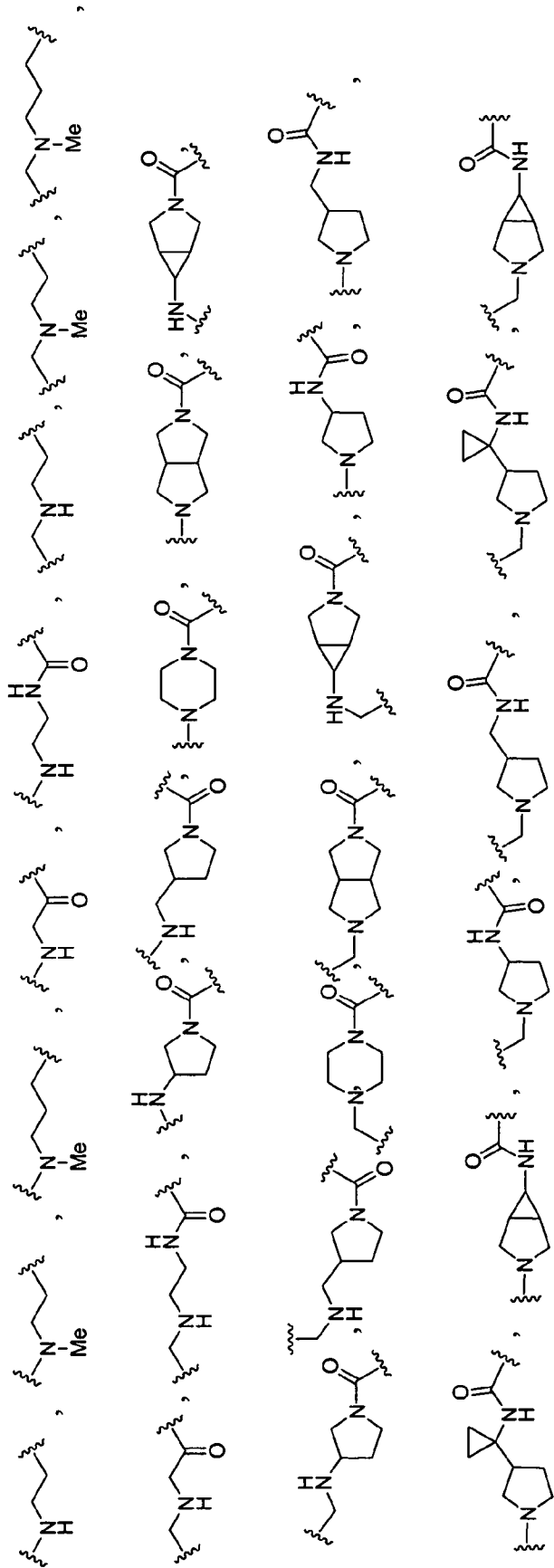
FIG. 4 shows a group of linkers, preferably used when linking rifamycin to a macrolide.
Figure 6:
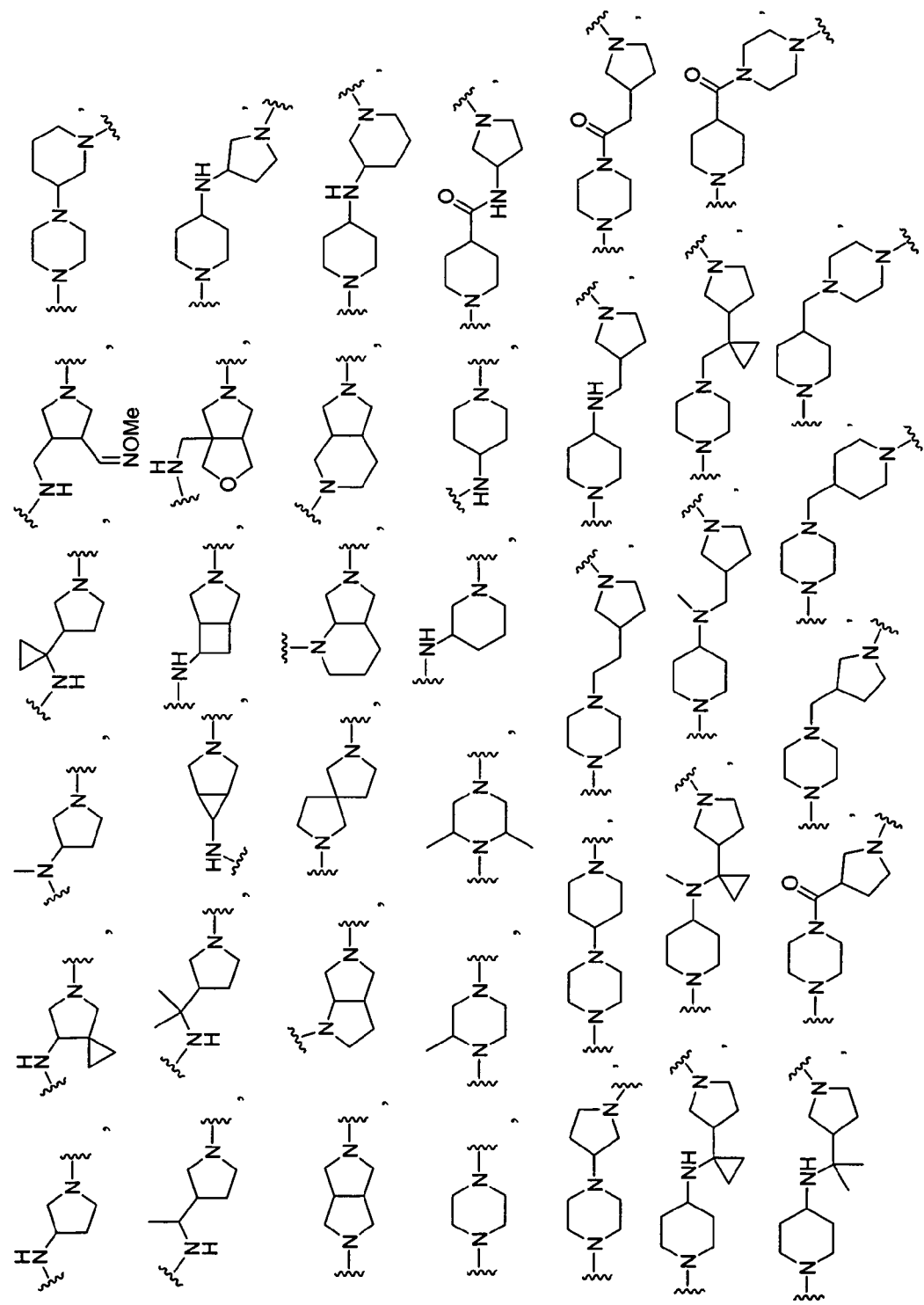
FIG. 6 shows a group of linkers, preferably used when linking rifamycin to a quinolone.

X represents a linker group consisting of various compositions and structural elements. In the preferred embodiments, the linkage group between the antibiotic "A" and the rifamycin molecule is not an imino (—C(H)=N—) group directly bonded to the C-3 position of the rifamycin moiety or its corresponding quinone form. "X" may consist of any combination of 1 to 5 of the following structures: —(C$_1$-C$_6$)alkylene, —(C$_1$-C$_6$)alkenylene, —(C$_1$-C$_6$)alkynylene, —(C$_3$-C$_8$)cycloalkylene, —O—, —C(H)=N—, —C(=O)—, —C(=N—O—R$_{13}$)—, —S—, —S(O)—, —S(O)$_2$—, —N(R$_{14}$)—, arylene, heteroarylene and heterocyclic structure containing 1 to 3 heteroatoms, wherein R$_{13}$ represents hydrogen, (C$_1$-C$_6$)alkyl, substituted (C$_1$-C$_6$)alkyl and R$_{14}$ represents hydrogen, (C$_1$-C$_6$)alkyl, substituted (C$_1$-C$_6$)alkyl. The carbon or nitrogen atoms of the linker group can be optionally substituted by 1 to 3 substituents selected from (C$_1$-C$_6$)alkyl, substituted (C$_1$-C$_6$)alkyl, heterocycloalkyl, amino, (C$_1$-C$_6$)alkylamino, di(C$_1$-C$_6$)alkylamino, hydroxyl, or (C$_1$-C$_6$)alkoxy. Examples of the linker groups are shown in FIGS. 1, 4, and 6. These examples are intended for illustration purposes only and are not intended to limit the scope of this invention.

As illustrated by Formula I and Formula II, the left-hand side of the linker group (FIGS. 1, 4, and 6) is covalently bonded or attached to the C-3 position of the rifamycin and the right-hand side of the linker is covalently bonded or attached to an antibiotic structure represented by "A." "A" can be an antibacterial pharmacophore associated with an antibacterial agent. Examples of "A" include compounds belonging to the macrolide class, the fluoroquinolone class, the non-fluoroquinolone class, the oxazolidinone class, the tetracycline class, the aminoglycoside class, the beta-lactam class, the sulfonamide class, the trimethoprim class, the glycopeptide class, the lipopeptide class, and the like.

Figure 2:
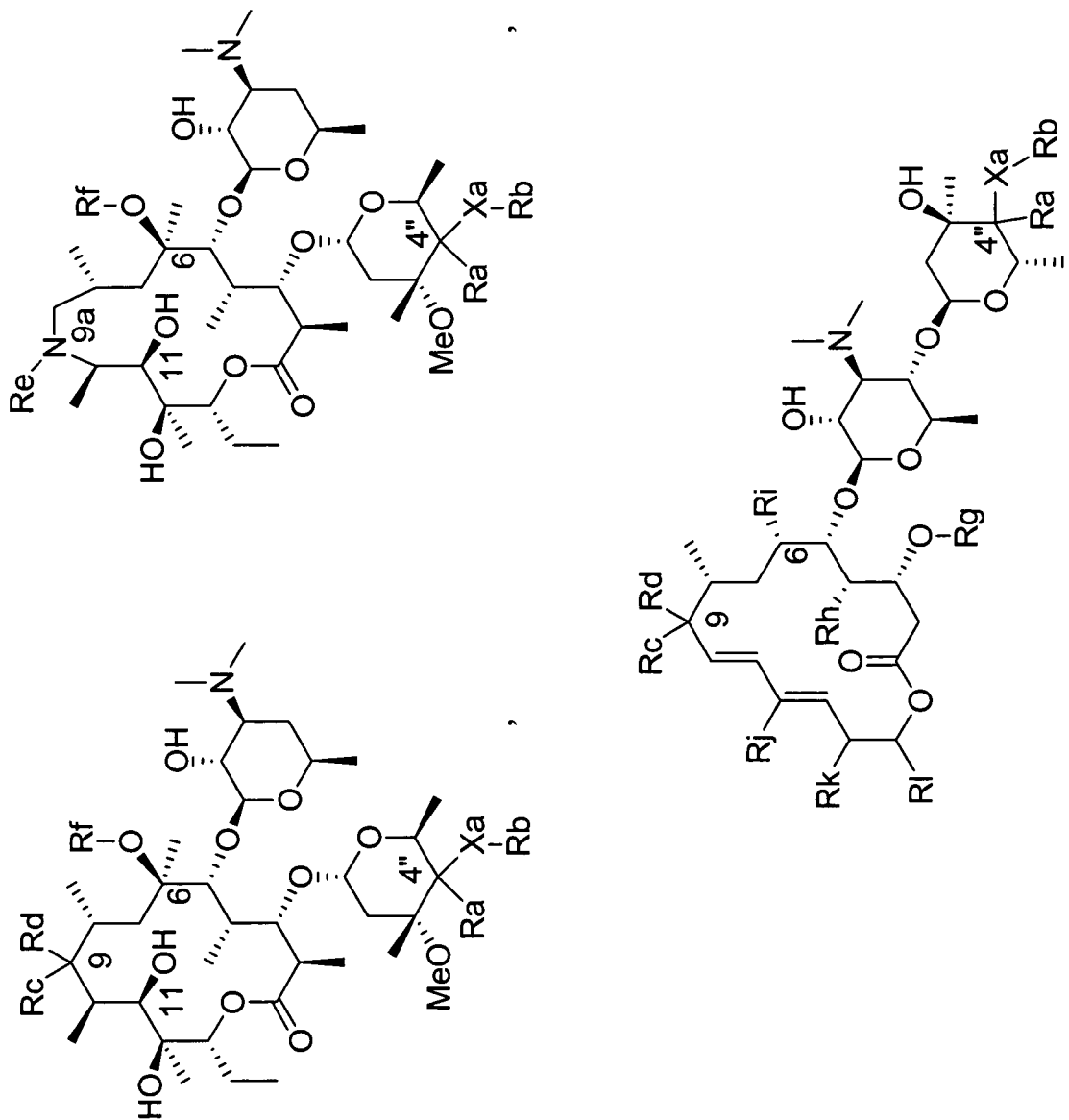
FIG. 2 shows a group of macrolides.

In a preferred embodiment, the group "A" is a structure related to the macrolide class of antibiotics. "A" can be a 14-membered ring, a 15-memebred ring or a 16-membered ring macrolide. Examples of macrolide antibiotics include erythromycin, erythromycylamine, clarithromycin, azithromycin, roxithromycin, dirithromycin, flurithromycin, oleandomycin, telithromycin, cethromycin, leucomycin, spiramycin, tylosin, rokitamycin, miokamycin, josamycin, rosaramycin, virginiamycin, and midecamycin. The preferred linking points on a macrolide structure is the C-4", C-6, C-9 or C9a position as illustrated by FIG. 2. The substituents in FIG. 2 are as follows: $R_a$ is hydrogen or hydroxyl; $X_a$ is —O—, —NH—, or —CH$_2$NH—; $R_b$ is —X—R$_x$, wherein X is a linker group exemplified by FIG. 1, R$_x$ is a group consisting of (C$_1$-C$_6$)alkyl, substituted (C$_1$-C$_6$)alkyl, aryl, substituted aryl, heteroaryl or substituted heteroaryl, or R$_x$ represents a rifamycin structure; R$_c$ or R$_d$ is hydrogen atom while the other constituent is a one of the following groups: hydroxyl, amino-, alkylamino, dialkylamino, —NH—X—R$_x$; both R$_c$ and R$_d$ and the carbon atom they are attached form >C=O or >C=N—O—X—R$_x$, wherein X and R$_x$ are defined above; R$_e$ is (C$_1$-C$_6$)alkyl, substituted (C$_1$-C$_6$)alkyl, or —X—R$_x$, wherein X and R$_x$ are the same as defined above; R$_f$ is hydrogen, (C$_1$-C$_6$)alkyl, or substituted (C$_1$-C$_6$)alkyl; R$_g$ is hydrogen, acetyl or propionyl group; R$_h$ is methyl or methoxyl group; R$_i$ is —CH$_2$CHO, —CH$_2$CH=N—O—X—R$_x$, —CH$_2$CH$_2$—NH—X—R$_x$, wherein X and R$_x$ are as defined above; R$_j$ is hydrogen or methyl; R$_k$ is hydrogen or —CH$_2$—O-sugar; and R$_l$ is methyl or ethyl.

Figure 3:
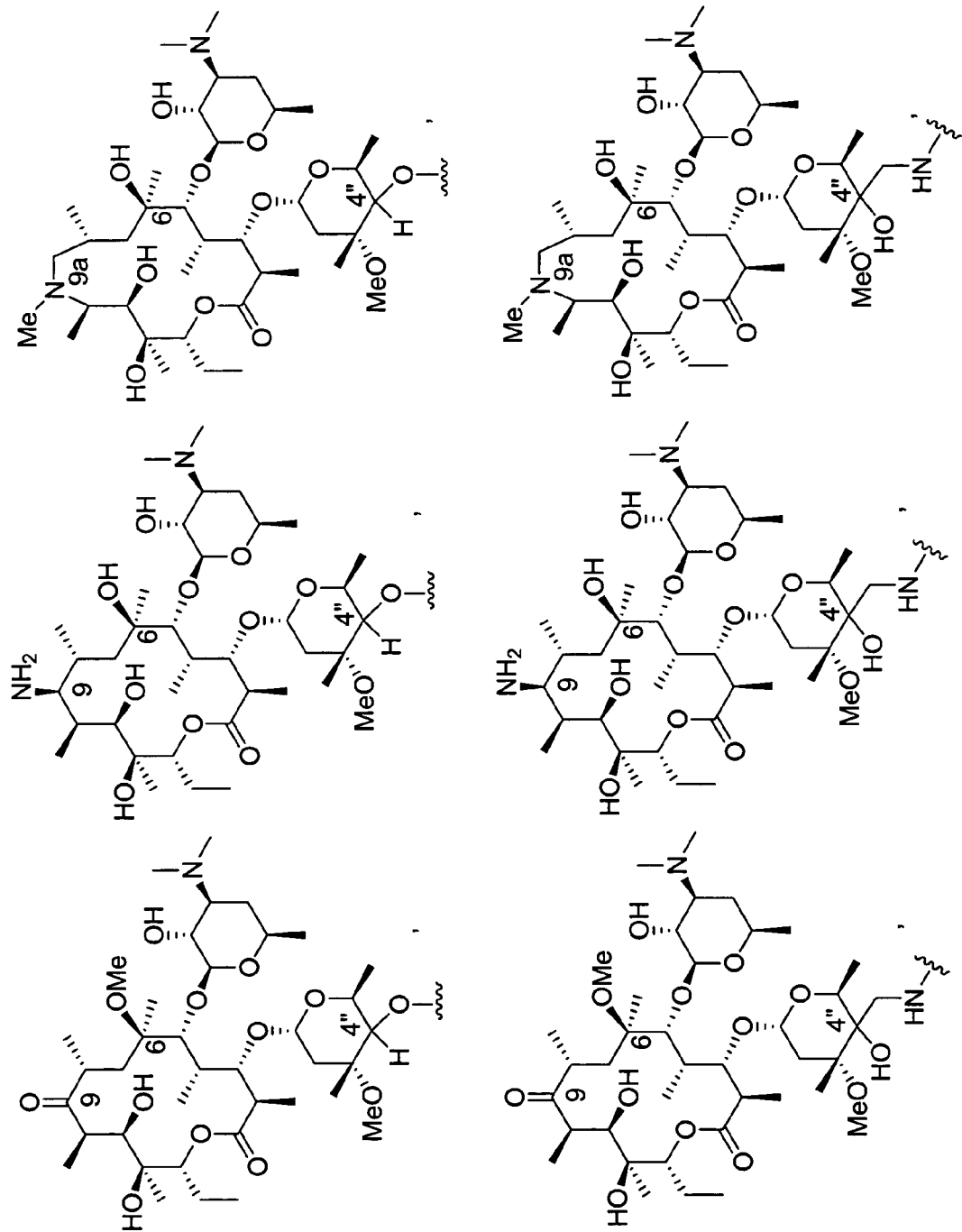
FIG. 3 shows a group of preferred macrolides.

In another preferred embodiment, A is a macrolide group selected from FIG. 3 and the linker "X" is selected from FIG. 4, wherein the left-hand side of the linker group is attached to the C-3 position of a rifamycin molecule and the right-hand side of the linker group is attached to the macrolide structure.

In yet another preferred embodiment, the antibiotic "A" is a structure related to the fluoroquinolone or non-fluoroquinolone class of antimicrobial agents selected from Formula III and IV:

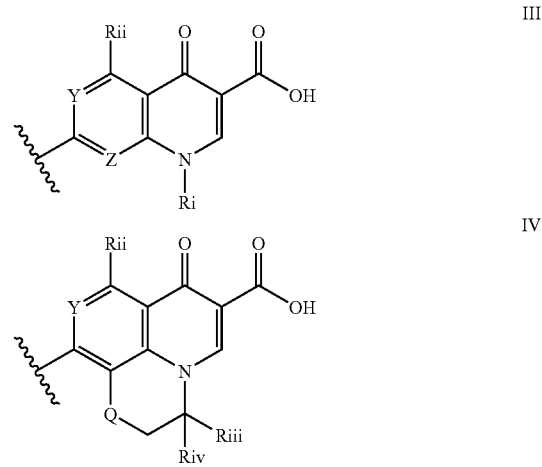

The substituents or groups in Formulas III and IV are as follows: $R_i$ represents (C$_1$-C$_6$)alkyl, (C$_3$-C$_6$)cycloalkyl, substituted (C$_3$-C$_6$)cycloalkyl, aryl, substituted aryl, heteroaryl, or substituted heteroaryl; $R_{ii}$ represents hydrogen, halogen, amino, nitro or methyl group; $R_{iii}$ and $R_{iv}$ independently represent hydrogen, (C$_1$-C$_6$)alkyl; or $R_{iii}$ and $R_{iv}$ join together with the carbon atom to which they are attached to form a 3- to 6-membered ring. Y represents C—H, C—F, or N; Z represents C—H, C—F, C—CN, C—CF$_3$, C—Cl, C-Me, C—OMe, C—OCH$_2$F, C—OCHF$_2$, or N. Q represents CH$_2$, O or S.

Figure 5:
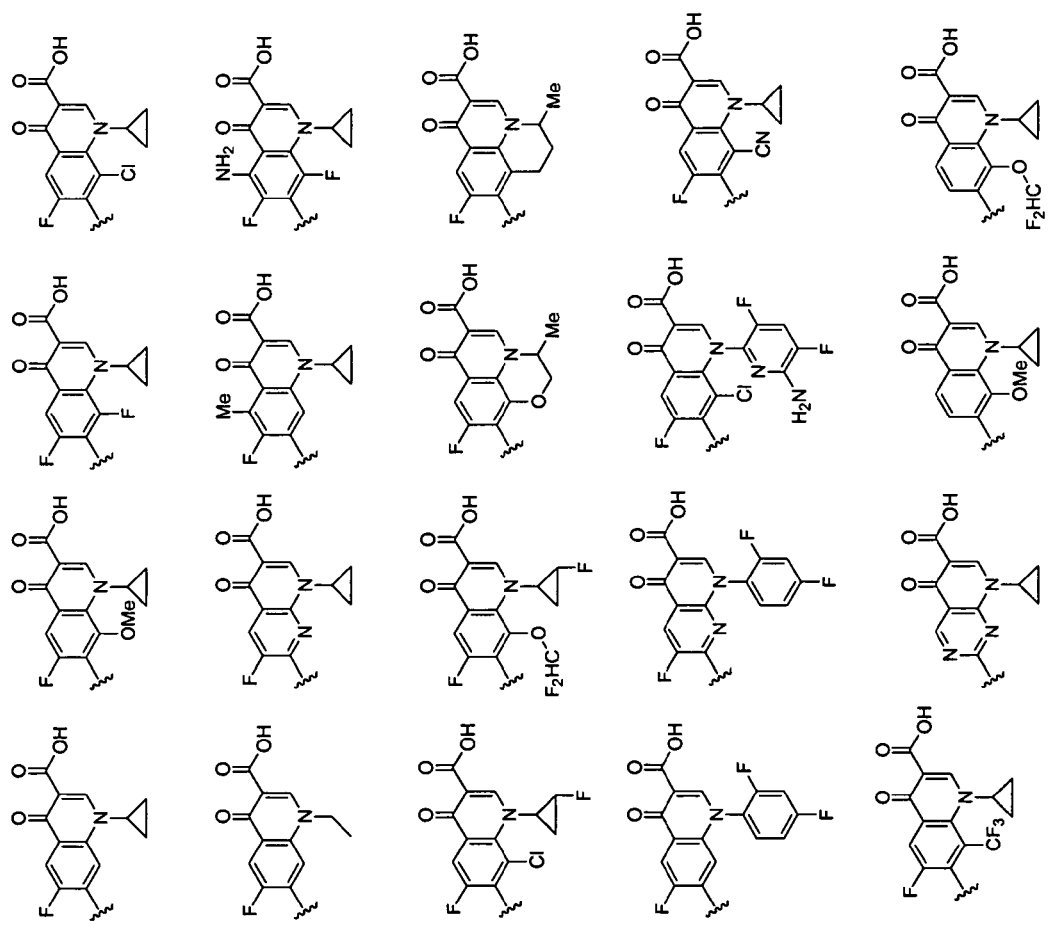
FIG. 5 shows a group quinolone structures.

In another more preferred embodiment, "A" is a quinolone structure selected from FIG. 5 and linker "X" is selected from FIG. 6, wherein the left-hand side of the linker group is attached to the C-3 position of a rifamycin molecule and the right-hand side of the linker group is attached to the quinolone structure at the indicated position.

Preferred antibiotic compounds of this invention are as follows: 3-[4-(3-Carboxy-1-cyclopropyl-6-fluoro-4-oxo-1,4-dihydroquinolin-7-yl)piperazin-1-yl]rifamycin S; 3-[4-(3-Carboxy-1-(2,4-difluorophenyl)-6-fluoro-4-oxo-1,4-dihydronaphthyridin-7-yl)piperazin-1-yl]rifamycin S; 3-[4-[3-[1-[3-Carboxy-1-(2,4-difluorophenyl)-6-fluoro-4-oxo-1,4-dihydronaphthyridin-7-yl]piperidin-4-yl]propyl]piperidin-1-yl]rifamycin S; (R/S)-3-[1-(3-Carboxy-8-chloro-1-cyclopropyl-6-fluoro-4-oxo-1,4-dihydroquinolin-7-yl)-pyrrolidin-3-ylamino]rifamycin S; (R)-3-[1-(3-Carboxy-1-cyclopropyl-6-fluoro-4-oxo-1,4-dihydroquinolin-7-yl)-pyrrolidin-3-ylamino]rifamycin S; (S)-3-[1-(3-Carboxy-1-cyclopropyl-6-fluoro-4-oxo-1,4-dihydroquinolin-7-yl)-pyrrolidin-3-ylamino]rifamycin S; (R,S)-3-[4-(3-Carboxy-1-cyclopropyl-6-fluoro-8-methoxy-4-oxo-1,4-dihydroquinolin-7-yl)-2-methylpiperazin-1-yl]rifamycin S; (R,S)-3-[4-(3-Carboxy-1-ethyl-6,8-difluoro-4-oxo-1,4-dihydroquinolin-7-yl)-2-methyl-piperazinyl]rifamycin SV; 3-[4-[3-Carboxy-1-cyclopropyl-6-fluoro-4-oxo-(1,4-dihydroquinolin-7-yl)]-piperazin-1-ylmethyl]rifamycin SV; (R/S)-3-[1-(8-Chloro-3-carboxy-1-cyclopropyl-6-fluoro-4-oxo-1,4-dihydroquinolin-7-yl)-pyrrolidinyl-3-aminomethyl]rifamycin SV; 3-[4-[3-carboxy-1-(2,4-Difluoro-phenyl)-6-fluoro-4-oxo-1,4-dihydro-[1,8]naphthyridin-7-yl]piperazin-1-ylmethyl]rifamycin SV; (R)-3-[1-(3-carboxy-1-cyclopropyl-6-fluoro-4-oxo-1,4-dihydroquinolin-7-yl)-pyrrolidinyl-3-aminomethyl]rifamycin SV; (s)-3-[1-(3-carboxy-1-cyclopropyl-6-fluoro-4-oxo-1,4-dihydroquinolin-7-yl)-pyrrolidinyl-3-aminomethyl]rifamycin SV; 3-[4-(3-Carboxy-1-cyclopropl-6-fluoro-4-oxo-1,4-dihydroquinolin-7-yl)piperazin-1-yl-aminomethylenyl]rifamycin SV; 3-[4-(3-Carboxy-1-cyclopropl-6-fluoro-4-oxo-1,4-dihydroquinolin-7-yl)-piperazin-1-yl-aminomethylenyl]rifamycin S; (R/S)-3-[1-(8-chloro-3-carboxy-1-cyclopropyl-6-fluoro-4-oxo-1,4-dihydroquinolin-7-yl)-pyrrolidin-3-ylhydrazinomethylenyl]rifamycin SV; (R/S)-3-[4-(3-Carboxy-1-cyclopropyl-6-fluoro-8-methoxy-4-oxo-1,4-dihydroquinolin-7-yl)-2-methyl-piperazin-1-yl-aminomethylenyl]rifamycin SV; (R/S)-3-[4-(3-Carboxy-1-ethyl-6,8-difluoro-8-4-oxo-1,4-dihydroquinolin-7-yl)-2-methyl-piperazin-1-yl-aminomethylenyl]rifamycin SV; (R/S)-3-[1-[3-Carboxy-1-(2,4-difluorophenyl)-6-fluoro-4-oxo-1,4-dihydro-[1,8]naphthyridin-7-yl]-pyrrolidinyl-3-hydrazinomethylenyl]rifamycin SV; 3-[4-[3-Carboxy-1-(2,4-difluoro-phenyl)-6-fluoro-4-oxo-1,4-dihydro-[1,8]naphthyridine-7-yl]-piperazin-1-ylaminomethylenyl]rifamycin S; 3-(Clarithromycin-4"-ylcarbamylethylamino)rifamycin S(R)-3-[3-(Clarithromycin-4"-ylcarbamylamino)-pyrrolidin-1-yl]-rifamycin S; (S)-3-[3-(Clarithromycin-4"-ylcarbamylamino)-pyrrolidin-1-yl]rifamycin S; 3-[4-(Clarithromycin-4"-ylcarbonyl)-piperazin-1-yl]rifamycin S; 3-(Azithromycin-4"-ylcarbamylethylamino)-rifamycin S; 3-(Clarithromycin-4"-ylcarbamylethylaminomethyl)rifamycin S V; (S)-3-[4-[4-(5-Acetylaminomethyl-2-oxo-oxazolidin-3-yl)-2-fluoro-phenyl]-piperazin-1-yl]rifamycin S; (S)-3-[4-[4-(5-Acetylaminomethyl-2-oxo-oxazolidin-3-yl)-2-fluoro-phenyl]-piperazin-1-ylethylamino]-rifamycin S; and 3-[1-(3-Carboxy-1-cyclopropyl-6-fluoro-4-oxo-1,4-dihydroquinolin-7-yl)azetidin-3-methylamino)rifamycin S, (R/S)-3-[4-(3-Carboxy-1-cyclopropyl-6-fluoro-8-methoxy-4-oxo-1,4-dihydroquinolin-7-yl)-piperazin-1-yl]rifamycin S, (R/S)-3-[1-(3-Carboxy-1-cyclopropyl-6-fluoro-8-methoxy-4-oxo-1,4-dihydroquinolin-7-yl)-pyrrolidin-3-ylamino-methyl]rifamycin S, (R/S)-3-{4-[1-(3-Carboxy-8-chloro-1-cyclopropyl-6-fluoro-4-oxo-1,4-dihydroquinolin-7-yl)-pyrrolidin-3-ylamino]-piperidin-1-yl}rifamycin S, (R/S)-3-{4-[1-(3-Carboxy-1-cyclopropyl-6-fluoro-8-methoxy-4-oxo-1,4-dihydroquinolin-7-yl)-pyrrolidin-3-ylamino]-piperidin-1-yl}rifamycin S, 3-{4-[1-(3-Carboxy-1-cyclopropyl-6-fluoro-8-methoxy-4-oxo-1,4-dihydroquinolin-7-yl)-piperazin-4-yl]-piperidin-1-yl}rifamycin S, (R/S)-3-{4-[1-(3-Carboxy-1-cyclopropyl-6-fluoro-8-methoxy-4-oxo-1,4-dihydroquinolin-7-yl)-piperidin-3-ylamino]-piperidin-1-yl}rifamycin S, 3-{4-[1-(3-Carboxy-1-cyclopropyl-6-fluoro-8-methoxy-4-oxo-1,4-dihydroquinolin-7-yl)-azetidin-3-ylamino]-piperidin-1-yl}rifamycin S, (R/S)-3-{4-[1-(3-Carboxy-1-cyclopropyl-6-fluoro-8-methoxy-4-oxo-1,4-dihydroquinolin-7-yl)-pyrrolidin-3-ylamino-methyl]-piperidin-1-yl}rifamycin S, 3-{4-[6-(3-Carboxy-1-cyclopropyl-6-fluoro-8-methoxy-4-oxo-1,4-dihydroquinolin-7-yl)-octahydro-pyrrolo[3,4-b]-pyrridin-1-yl]-piperidin-1-yl}rifamycin S, (R/S)-3-{4-[1-(3-Carboxy-8-chloro-1-cyclopropyl-6-fluoro-4-oxo-1,4-dihydroquinolin-7-yl)-(pyrrolidin-3-ylmethyl)-amino]-piperidin-1-yl}rifamycin S, (R/S)-3-{4-[1-(3-Carboxy-1-(2,3-difluoro-phenyl)-6-fluoro-4-oxo-1,4-dihydro[1,8]naphthyridine-7-yl)-(pyrrolidin-3-ylmethyl)-amino]-piperidin-1-yl}rifamycin S, 3-{4-[1-(3-Carboxy-8-chloro-1-cyclopropyl-6-fluoro-4-oxo-1,4-dihydroquinolin-7-yl)-piperazin-4-yl]-piperidin-1-yl}rifamycin S, 3-{4-[1-(3-Carboxy-1-cyclopropyl-6-fluoro-8-methoxy-4-oxo-1,4-dihydroquinolin-7-yl)-pyrrolidin-3-ylethylamino]-piperidin-1-yl}rifamycin S, (R/S)-3-{4-(1-[1-(3-Carboxy-1-(2,3-difluoro-phenyl)-6-fluoro-4-oxo-1,4-dihydro-[1,8]naphthyridine-7-yl)-pyrrolidin-3-yl]-piperazin-1-yl)-piperidin-1-yl}-rifamycin S, (R/S)-3-[4-{1-[1-(3-Carboxy-1-cyclopropyl-6-fluoro-8-methoxy-4-oxo-1,4-dihydro-quinoline-7-yl)-pyrrolidin-3-yl]-cyclopropylamino}-piperidin-1-yl]-rifamycin S, (R/S)-3-{4-({1-[1-(3-Carboxy-8-chloro-1-cyclopropyl-6-fluoro-4-oxo-1,4-dihydro-quinolin-7-yl)-pyrrolidin-3-yl]-cyclopropyl}-methyl-amino)-piperidin-1-yl]-rifamycin S, (R/S)-3-{3-[1-(3-Carboxy-8-chloro-1-cyclopropyl-6-fluoro-4-oxo-1,4-dihydroquinolin-7-yl)-pyrrolidin-3-ylcarbamoyl]-azetidin-1-yl}rifamycin S, (R/S)-3-{3-[1-(3-Carboxy-1-cyclopropyl-6-fluoro-8-methoxy-4-oxo-1,4-dihydroquinolin-7-yl)-pyrrolidin-3-ylcarbamoyl]-azetidin-1-yl}rifamycin S, 3-{3-[4-(3-Carboxy-1-cyclopropyl-6-fluoro-8-methoxy-4-oxo-1,4-dihydroquinolin-7-yl)-piperazin-1-yl-carbonyl]-azetidin-1-yl}rifamycin S, 3-{3-[1-(3-Carboxy-1-cyclopropyl-6-fluoro-8-methoxy-4-oxo-1,4-dihydroquinolin-7-yl)-piperidin-3-ylcarbamoyl]-azetidin-1-yl}rifamycin S, 3-{3-[1-(3-Carboxy-1-cyclopropyl-6-fluoro-8-methoxy-4-oxo-1,4-dihydroquinolin-7-yl)-azetidin-3-ylcarbamoyl]-azetidin-1-yl}rifamycin S, 3-{3-(4-[1-(5-methyl-acetamidyl-2-oxo-oxazolidin-3-yl)-5-fluoro-phen-4-yl]-piperazin-1-ylcarbonyl)-azetidin-1-yl}-rifamycin S, (R/S)-3-{4-[1-(3-Carboxy-8-chloro-1-cyclopropyl-6-fluoro-4-oxo-1,4-dihydroquinolin-7-yl)-pyrrolidin-3-ylcarbarnoyl]-piperidin-1-yl}rifamycin S, (R/S)-3-{4-[1-(3-Carboxy-1-cyclopropyl-6-fluoro-8-methoxy-4-oxo-1,4-dihydroquinolin-7-yl)-pyrrolidin-3-ylcarbamoyl]-piperidin-1-yl}rifamycin S, 3-{4-[4-(3-Carboxy-1-cyclopropyl-6-fluoro-8-methoxy-4-oxo-1,4-dihydroquinolin-7-yl)-piperazin-1-ylcarbonyl]-piperidin-1-yl}rifamycin S, (R/S)-3-{4-[1-(3-Carboxy-1-cyclopropyl-6-fluoro-8-methoxy-4-oxo-1,4-dihydroquinolin-7-yl)-piperidin-3-ylcarbamoyl]-piperidin-1-yl}rifamycin S, 3-{4-[1-(3-Carboxy-1-cyclopropyl-6-fluoro-8-methoxy-4-oxo-1,4-dihydroquinolin-7-yl)-azetidin-3-ylcarbamoyl]-piperidin-1-yl}rifamycin S, (R/S)-3-{4-[1-(3-Carboxy-1-(2,3-difluoro-phenyl)-6-fluoro-4-oxo-1,4-dihydro[1,8]naphthyridine-7-yl)-pyrrolidin-3-yl]-piperazin-1-yl}-rifamycin S, (R/S)-3-{4-(1-[1-(3-Carboxy-1-(2,3-difluorophenyl)-6-fluoro-4-oxo-1,4-dihydro-[1,8]naphthyridine-7-yl)-pyrrolidin-3-yl]-piperazin-1-yl]-piperidin-1-yl}-rifamycin S, 3-[1-(3-Carboxy-1-cyclopropyl-6-fluoro-4-oxo-1,4-dihydro-[1,8]naphthyridine-7-yl)-piperazin-4-yl]-rifamycin S, (R/S)-3-{4-[1-(3-Carboxy-1-cyclopropyl-6-fluoro-8-methoxy-4-oxo-1,4-dihydroquinoline-7-yl)-pyrrolidin-3-yl-cyclopropyl]-piperazin-1-yl}-rifamycin S, (R/S)-3-{4-[1-(3-Carboxy-8-chloro-1-cyclopropyl-6-fluoro-4-oxo-1,4-dihydroquinoline-7-yl)-pyrrolidin-3-yl-cyclopropyl]-piperazin-1-yl}-rifamycin S.

EXAMPLE 2

Administration to a Subject:

The pharmaceutical composition of the present invention comprises a therapeutically effective amount of a compound of the current invention formulated together with one or more pharmaceutically acceptable carriers. Injectable preparations can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a drug, it is often desirable to slow the absorption of the drug through subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and the following: 1) fillers or extenders such as starches, lactose, sucrose, glucose, mannitol, and silicic acid, 2) binders such as, carboxymethylcellulose, alginates, gelatin, polyvinylpyrrolidinone, sucrose, and acacia, 3) humectants such as glycerol, 4) disintegrating agents such as agar-agar, calcium carbonate, potato or tapioca starch, alginic acid, certain silicates, and sodium carbonate, 5) solution retarding agents such as paraffin, 6) absorption accelerators such as quaternary ammonium compounds, 7) wetting agents such as, cetyl alcohol and glycerol monostearate, 8) absorbents such as kaolin and bentonite clay, and 9) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient only, or preferentially, in a certain part of the intestinal tract, optionally, in a delayed manner. Examples of embedding compositions which can be used include polymeric substances and waxes. The active compounds can also be in microencapsulated form with one or more excipients as noted above.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required. Ophthalmic formulation, ear drops, eye ointments, powders and solutions are also contemplated as being within the scope of this invention. The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or animal by administering to the patient a therapeutically effective amount of a compound of the invention, in such amounts and for such time as is necessary to achieve the desired therapeutic effects. The term "therapeutically effective amount" of a compound of the invention is meant a sufficient amount of the compound to treat bacterial infections, at a reasonable benefit to risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or animals in single or in divided doses can be in amounts, for example, from 0.1 to 100 mg/kg body weight or preferably from 0.25 to 25 mg/kg body weight. Single dose compositions can contain such amounts or submultiples thereof to make up the daily dose. In general, treatment regimens according to the present invention comprise administration to an infected patient of such treatment from about 10 mg to about 2000 mg of the compounds of this invention per day in single or multiple doses. The compounds of current invention can be administrated orally, rectally, parenterally, intracisternally, intravaginally, intraperitoneally, topically, bucally, or as an oral or nasal spray.

Biological Activity:

Representative compounds were assayed for antimicrobial activity as follows: Minimum Inhibitory Concentrations ("MICs") were determined by the microbroth dilution method as per NCCLS guidelines (National Committee for Clinical Laboratory Standards. 2000. Methods for dilution antimicrobial susceptibility tests for bacteria that grow aerobically, 5th ed. M7-A5. National Committee for Clinical Laboratory Standards, Wayne, Pa.), except that all growth incubations were conducted at 37° C. Bacterial cultures were tested in the following bacteriological media: $S.$ $aureus$, $S.$ $epidermidis$, and $E.$ $coli$ in Cation-Adjusted Mueller-Hinton Broth, $S.$ $pneumoniae$ in THY Broth supplemented with 1 mg/mL catalase under 5% $CO_2$ atmosphere, $S.$ $pyogenes$ in THY Broth, $E.$ $faecalis$ in BHI Broth, $H.$ $influenzae$ in BHI Broth supplemented with 0.75 μL of 1 mg/mL NAD and 150 μL of 1 mg/ml hematin per 5 mL, and $M.$ $smegmatis$ in Middlebrook Broth plus ADC Enrichment. The antimicrobial activity of the example compounds of the current invention are shown in Table 1.

$S.$ $aureus$ ATCC 2213, $S.$ $epidermidis$ ATCC 12228, $S.$ $pneumoniae$ ATCC6303, $S.$ $pyogenes$ ATCC 19615 and $E.$ $faecalis$ ATCC 29212 are rifampin-susceptible Gram-positive strains. Rifampin exhibits excellent activity against these organisms with MICs between 0.008 and 1 μg/ml. Certain compounds of the current invention show improved activity against these strains with MICs as low as 0.004 μg/ml. $H.$ $influenzae$ ATCC 10211 and $E.$ $coli$ ATCC 25922 are Gram-negative bacteria. Rifampin has intrinsic weaker activity against these organisms with MICs between 0.24 and 16 μg/ml. Certain compounds of the current invention also demonstrate improved activity against these strains with MICs as low as 0.125 μg/ml. In addition, rifampin exhibits low activity against a mycobacterial strain $M$ $smegamatis$ ATCC 700084 with a MIC 64 μg/ml. While certain compounds of the current invention show potent activity against this strain with a MIC 0.5 μg/ml.

Most importantly, compounds of the current invention demonstrate excellent activity against rifampin-resistant organisms. $S.$ $aureus$ ATCC 29213 $RpoB^{H418Y}$ is a rifampin-resistant strain with a mutation in RNA polymerase, the biological target of rifamycin antibiotics. This mutation results in a significant increase in the MIC for rifampin to 8 μg/ml. Certain compounds of the current invention exhibit potent activity against this strain with a MIC as low as 0.06 μg/ml. $S.$ $aureus$ ATCC 29213 $RpoB^{D417Y}$ is a high level rifampin-resistant strain due to a RNA polymerase mutation with a MIC >64 μg/ml for rifampin. Certain compounds of the current invention are potent against this highly rifampin-resistant strain with MICs in the 0.06 μg/ml level. $S.$ $aureus$ EN1252a $gyrA^{S84L}$ $grlA^{S80F}$ is a quinolone-resistant strain due to double mutations to DNA gyrase and topoisomerase IV, the two biological targets for quinolone antibiotics. The MIC of ciprofloxacin against this strain is 8 μg/ml. Certain compounds of the current invention demonstrate potent activity against this strain with MICs between 0.004 and 0.5 μg/ml.

TABLE 1

Antimicrobial activity (range of MICs, mcg/ml) of selected compounds

| Organism | | rifampin | cipro | Example 4-60 |
|---|---|---|---|---|
| Staphylococcus aureus ATCC29213 | rifS | 0.008 | 0.25 | 0.004-0.5 |
| Staphylococcus aureus ATCC29213 rpoB$^{H418Y}$ | rifR | 8 | 0.25 | 0.06-16 |
| Staphylococcus aureus ATCC29213 rpoB$^{D417Y}$ | rifR | >64 | 0.25 | 0.06-32 |
| Staphylococcus aureus EN1252a$^a$ gyrA$^{S84L}$ grlA$^{S80F}$ | cipR | 0.004 | 8 | 0.004-0.5 |
| Staphylococcus epidermidis ATCC12228 | rifS | 0.03 | 0.125 | 0.008-0.063 |
| Streptococcus pneumoniae ATCC6303 | rifS | 0.061 | 1 | 0.008-0.125 |
| Streptococcus pyogenes ATCC19615 | rifS | 0.013 | 0.5 | 0.008-0.063 |
| Enterococcus faecalis ATCC29212 | rifS | 1 | 0.5 | 2-32 |
| Haemophilus influenzae ATCC10211 | rifS | 0.24 | 0.008 | 0.125-2 |
| Escherichia coli ATCC25922 | rifS | 16 | 0.03 | 0.125-8 |
| Mycobacterium smegmatis ATCC700084 | rifS | 64 | 0.125 | 0.5-64 |

$^a$For strain MT1222 see: Ince & Hooper, Antimicrobial Agents and Chemotherapy, 2000, 44, 3344-50.

EXAMPLE 3

Synthetic Methods:

The compounds of the current invention can be better understood in connection with the following general synthetic schemes. The synthetic procedures shown below in Schemes 1 to 10 are for illustration purposes and are not intended for limiting the scope of the invention. It will be apparent to one skilled in the art that the compounds of the current invention can be prepared by a variety of synthetic routes, including but not limited to substitution of appropriate reagents, solvents or catalysts, change of reaction sequence, and variation of protecting groups. The groups $R_1$, $R_2$, $R_3$, X, $X_1$, $X_2$, and A in Scheme 1 to 10 (FIGS. 7-14) are as defined above.

Figure 7:
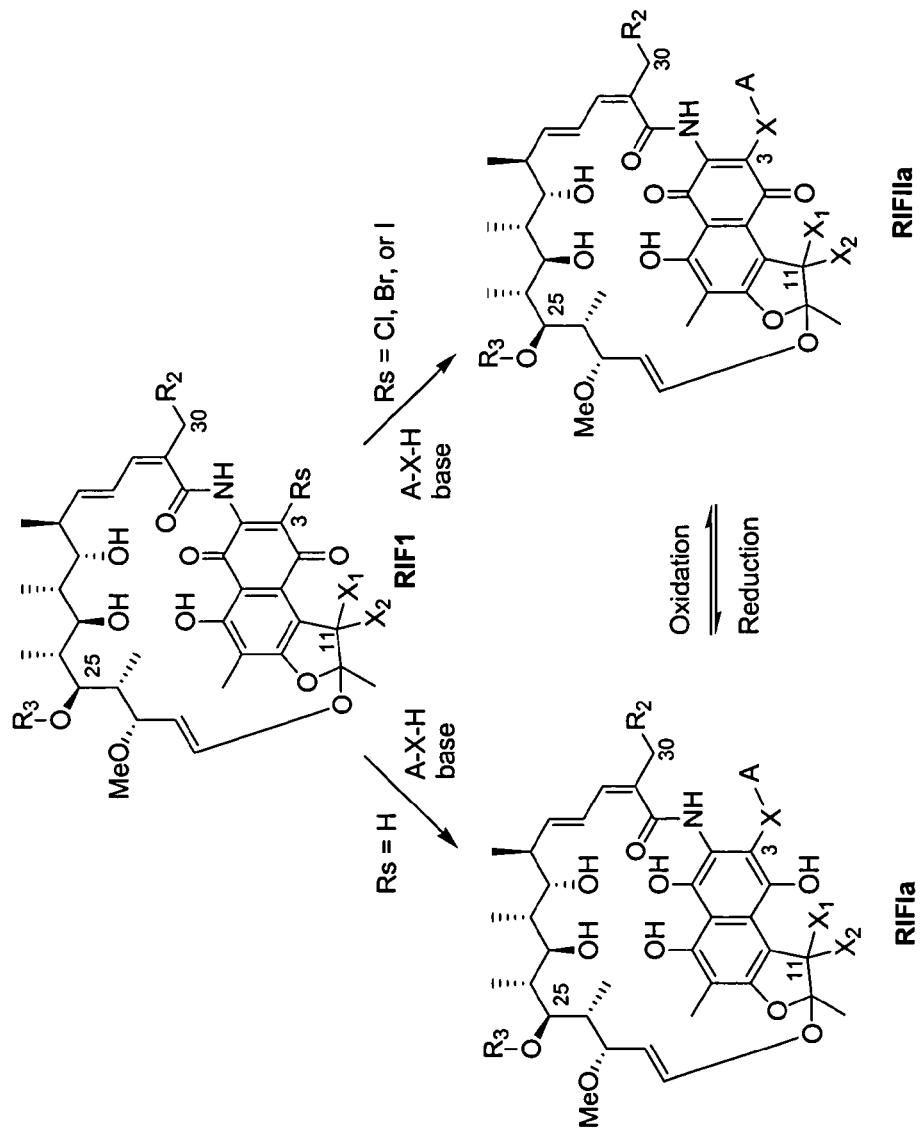
FIG. 7 shows Scheme I, wherein a rifamycin derivative reacts with a molecule of general formula A-X—H.

Scheme 1 in FIG. 7 illustrates that compounds RIFIa and RIFIIa of Formula I and II of this invention can be prepared by reacting rifamycin B or a 3-halorifamycin (RIF1), wherein $R_s$ represents hydrogen, chloro, bromo or iodo group, with a molecule of structure A-X—H, which contains a nucleophilic group in the molecule. The nucleophilic group can be an amino, a hydroxyl, a thio group, a phosphate or a carbon based nucleophilic group such as an enolate or a malonate. When A-X—H reacts directly with a C-3 unsubstituted rifamycin compounds ($R_s$=H) in the presence of a base, hydroquinone product RIFIa can be obtained. When A-X—H reacts with a 3-halorifamycin compound ($R_s$=Cl, Br, or I), quinone product RIFIIa can be obtained. Compounds (RIFIa, IIa) can be readily converted from one to another by an oxidation and reduction reaction using red-ox agents, such as ascorbic acid and potassium ferrocyanide.

Figure 8:
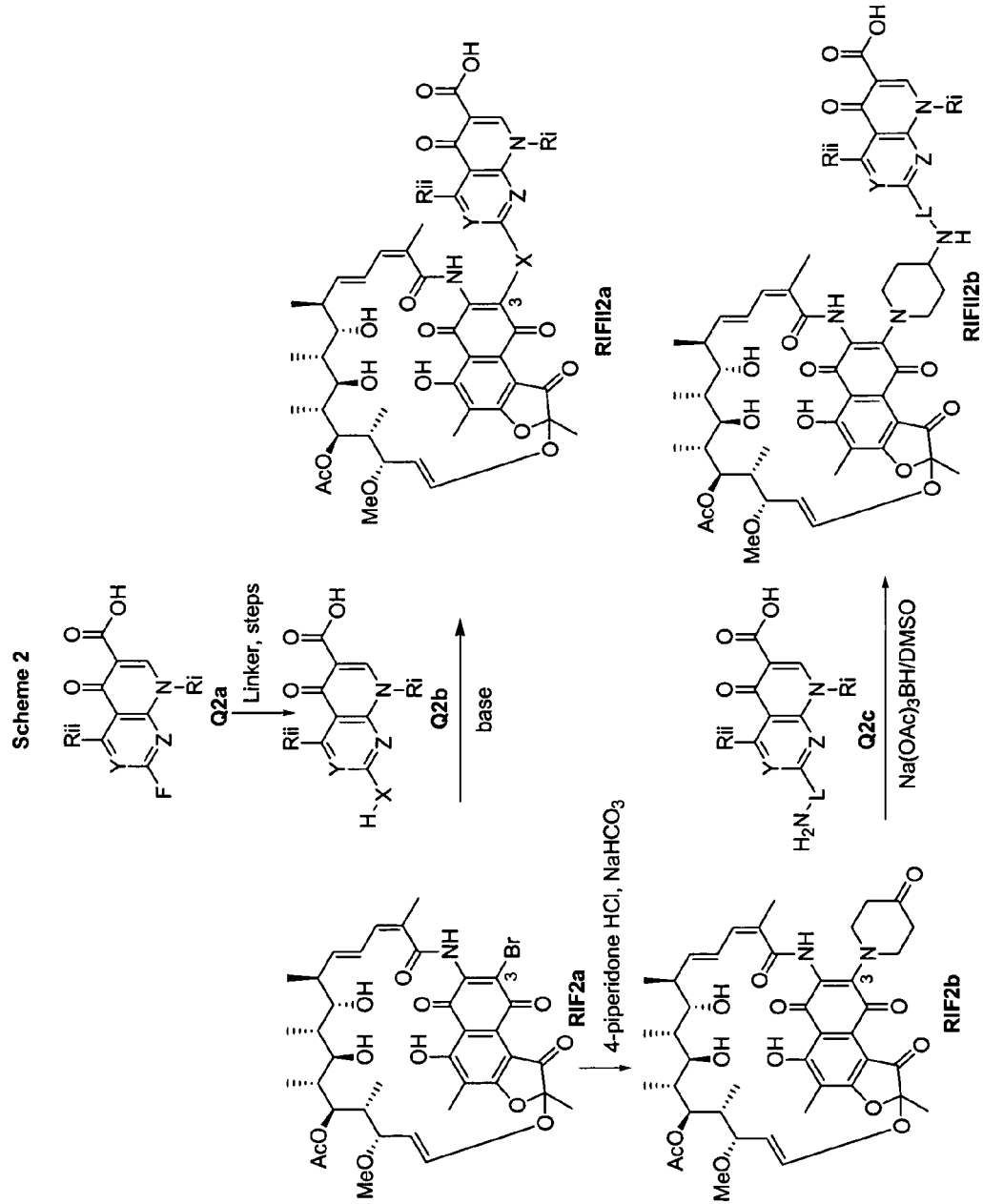
FIG. 8 shows Scheme 2, wherein rifamycin derivatives react with quinolone compounds, and the preparation of the pre-requisite quinolones.

Specific examples of the current invention are illustrated by Scheme 2 in FIG. 8, where 3-bromorifamycin S (RIF2a) reacts with a quinolone compound (Q2b) to give product (RIFIIa) of Formula II of this invention. The quinolones (Q2b) can be readily prepared starting from fluoroquinolone core (Q2a) and a nucleaphilic amine linker "X" by following the known literature procedures (such as, Domagala, J. M. et al: *J. Med. Chem.* 1991, 34, 1142-1154; Sanchez, J. P. et al: *J. Med. Chem.* 1988, 31, 983-991) to give quinolone (Q2b). The quinolone (Q2b) may also be commercially available from chemical vendors, like LKT Laboratories, Inc. St. Paul, Minn. 55114, USA. The starting quinolone core (Q2a) or a quinolone pharmacophore fragment is commercially available from Louston International Inc., Linwood, Pa. 19061, USA. The nucleophilic amine linkers can be purchased from chemical venders, like Aldrich Chemical Company, Milwaukee, Wis. 53201, USA or readily prepared starting from commercially available chemicals by following the known literature procedures practiced by someone who is skilled in the art. Alternatively, 3-bromorifamycin (RIF2a) can be transformed to 3-(4-piperidinone)-rifamycin (RIF2b) upon reaction with piperidinone hydrochloride in an alcoholic solvent or THF and water in the presence of an inorganic base, like sodium bicarbonate or an organic base, like TEA. Reductive amination of 3-(4-piperidinone)-rifamycin (RIF2b) with a quinolone (Q2c), wherein there is a basic reactive amine (like-$NH_2$ or >NH), using a reducing agent, like sodium triacetoxyborohydride, may be used to prepared the compound (RIFIIb) of Formula II of this invention. It will be apparent to one skilled in the art that 3-bromorifamycin S (RIF2a) can be replaced by other 3-halorifamycin analogs and the quinolone compounds can be replaced by other antibiotics within the gyrase/topoisomerase IV inhibitor family. The displacement reaction between a rifamycin (RIF2a) and a quinolone (Q2b) may be performed in a protic or aprotic solvent catalyzed by an organic or inorganic base. Examples of solvents suitable for this reaction are THF, DMSO, DMF, NMP, ethanol, isopropanol, methanol, dioxane, acetonitrile, water or any combination of the above. Examples of bases are $NaHCO_3$, $Na_2CO_3$, $KHCO_3$, $K_2CO_3$, $Cs_2CO_3$, NaOH, LiOH, TEA, Pyridine, DMAP, DBU, etc. Under certain circumstances, excess of quinolone compound (Q2b) may be used as base.

Figure 9:
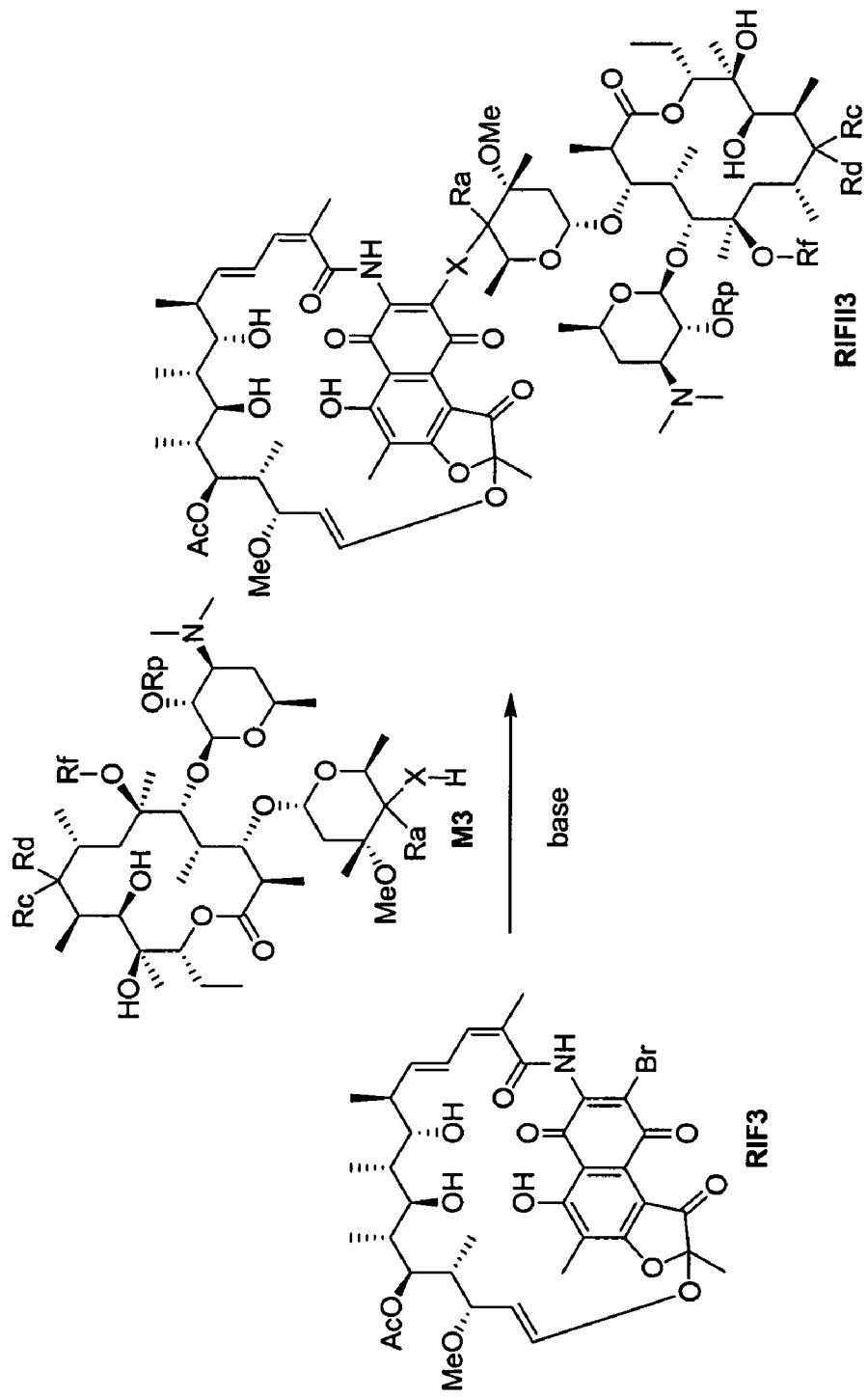
FIG. 9 shows Scheme 3, wherein a rifamycin derivative reacts with a macrolide compound.

Another specific example is illustrated by Scheme 3 in FIG. 9, where 3-bromorifamycin S (RIF3) reacts with a macrolide compound (M3), wherein $R_p$ is a hydrogen or a hydroxyl protecting group such as acetyl or benzoyl, to give product (RIFII3) of Formula II of this invention. It will be apparent to one skilled in the art that 3-bromorifamycin S (RIF3) can be replaced by other 3-halorifamycin analogs and the macrolide compound (M3) can be replaced by other structures within the macrolide family that include 14-membered ring, 15-membered ring and 16-membered ring macrolide structures. It will be also apparent to one skilled in the art that the macrolide structure can be linked at other positions such as the 6-position, the 9-position or the 11-position. The reaction is performed in a protic or aprotic solvent catalyzed by an organic or inorganic base. Examples of solvents suitable for this reaction are THF, DMSO, DMF, NMP, ethanol, isopropanol, methanol, dioxane, acetonitrile, water or any combination of the above. Examples of bases are $NaHCO_3$, $Na_2CO_3$, $KHCO_3$, $K_2CO_3$, $Cs_2CO_3$, NaOH, LiOH, TEA, Pyridine, DMAP, DBU, etc. Under certain circumstances, excess of the compound (M3) can be used as base.

Figure 10:
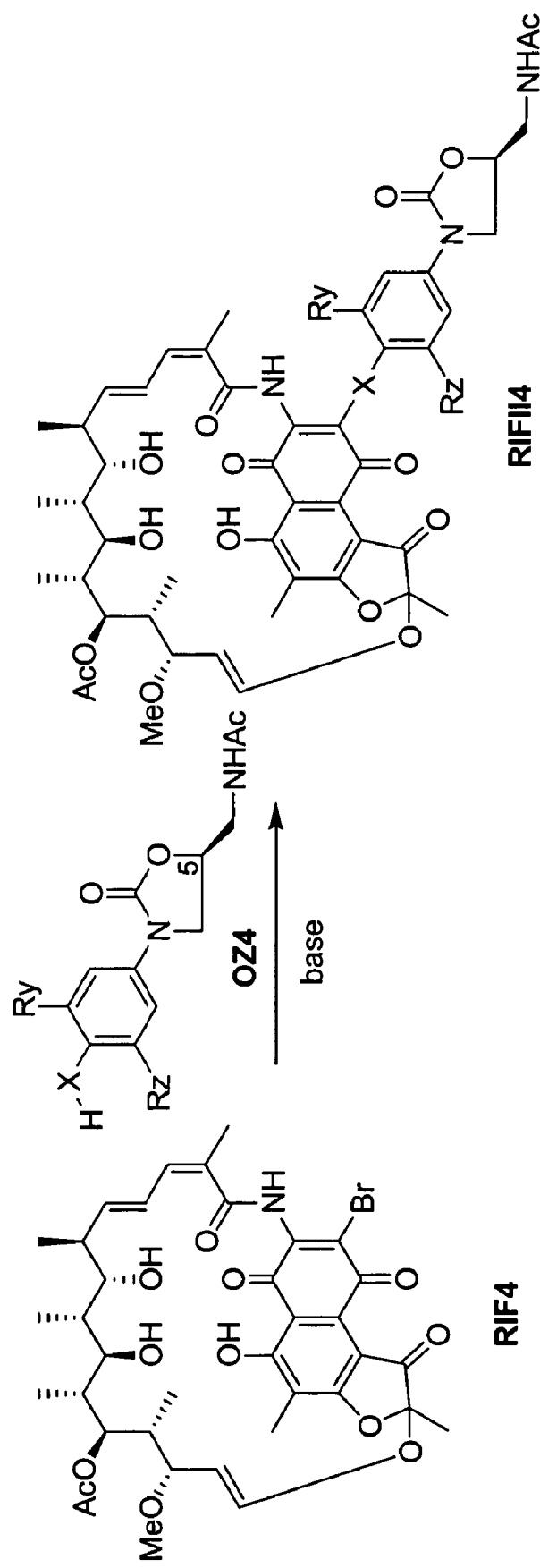
FIG. 10 shows Scheme 4, wherein a rifamycin derivative reacts with an oxazolidinone compound.

Yet another specific example of the current invention is illustrated by Scheme 4 in FIG. 10, where 3-bromorifamycin S (RIF4) reacts with an oxazolidinone compound (OZ4), wherein Ry and Rz are independently selected from H or F, to give product (RIFII4) of Formula II of this invention. It will be apparent to one skilled in the art that 3-bromorifamycin S (RIF4) can be replaced by other 3-halorifamycin analogs and the oxazolidinone compound (OZ4) can be replaced by other structures within the oxazolidinone family. Specific variations to the oxazolidinone structure can be made to the C-5 position as indicated on structure (OZ4). These variations are known to those having ordinary skill in the art (for example see: Hutchinson, D. K., *Current Topics in Medicinal Chemistry,* 2003, 3, 1021-1042, the entire content of which is hereby incorporated by reference). The reaction is performed in a protic or aprotic solvent catalyzed by an organic or inorganic base. Examples of solvents suitable for this reaction are THF, DMSO, DMF, NMP, ethanol, isopropanol, methanol, dioxane, acetonitrile, water or any combination of the above. Examples of bases are $NaHCO_3$, $Na_2CO_3$, $KHCO_3$, $K_2CO_3$, $Cs_2CO_3$, NaOH, LiOH, TEA, Pyridine, DMAP, DBU, etc. Under certain circumstances, excess of oxazolidinone (OZ4) can be used as base.

Figure 11:
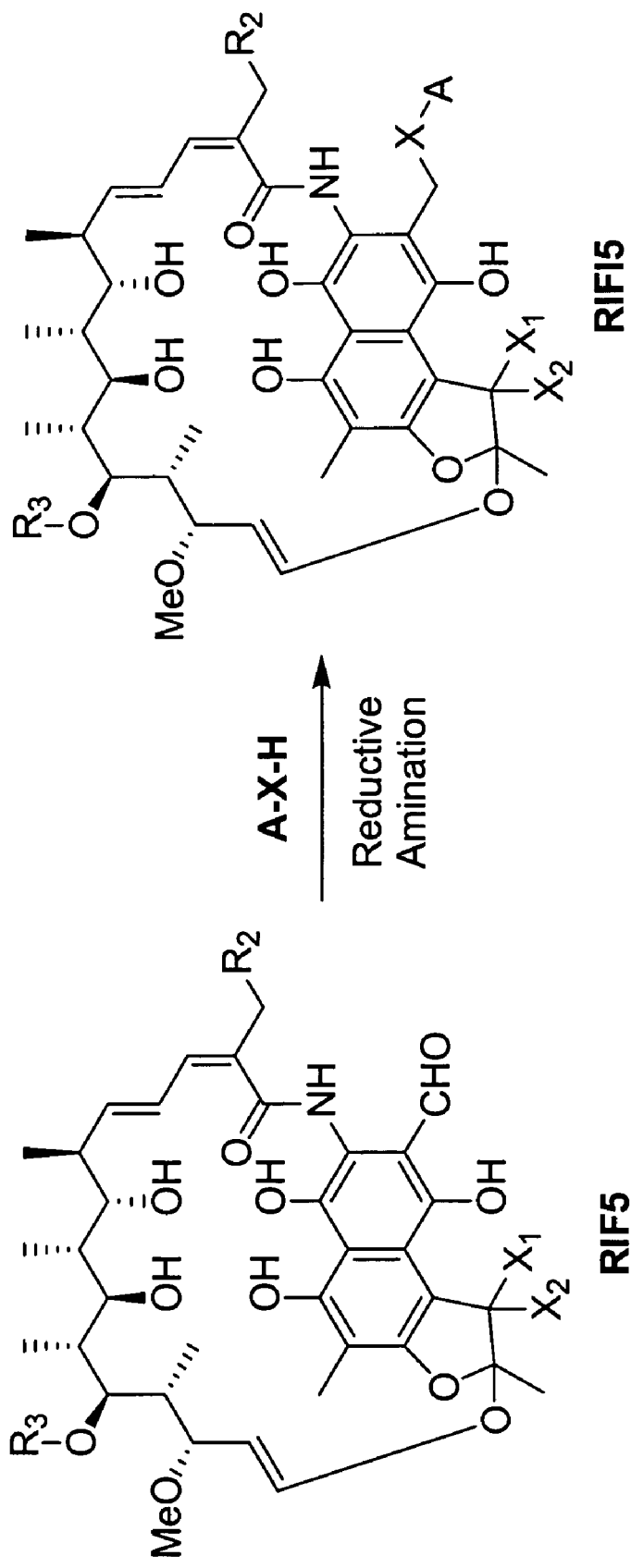
FIG. 11 shows Scheme 5, wherein a rifamycin derivative undergoes reductive amination with a molecule of general formula A-X—H.

Scheme 5 in FIG. 11 illustrates that compounds of Formula I of this invention can be prepared from 3-formylrifamycin (RIF5). In this particular case, the linker group must consist of a primary or secondary amino group. The reaction can be performed stepwise, where compound of the formula A-X—H reacts with 3-formylrifamycin compounds (RIF5) to produce an imine or iminium ion intermediate which can then be reduced by a reducing agent like sodium cyanoborohydride to give desired compound (RIFI5). Alternatively, compounds of the formula A-X—H, 3-formylrifamycin (RIF5) and a reducing agent can be mixed together in a single step to give the desired compound (RIFI5). The reaction is performed in a protic or aprotic solvent. Examples of solvents suitable for this reaction are THF, DMSO, DMF, NMP, ethanol, isopropanol, methanol, dioxane, acetonitrile, acetic acid, water, or any combination of the above. Examples of reducing agents are sodium borohydride, sodium triacetoxyborohydride, sodium cyanoborohydride, and hydrogen in presence of a palladium catalyst.

Figure 12:
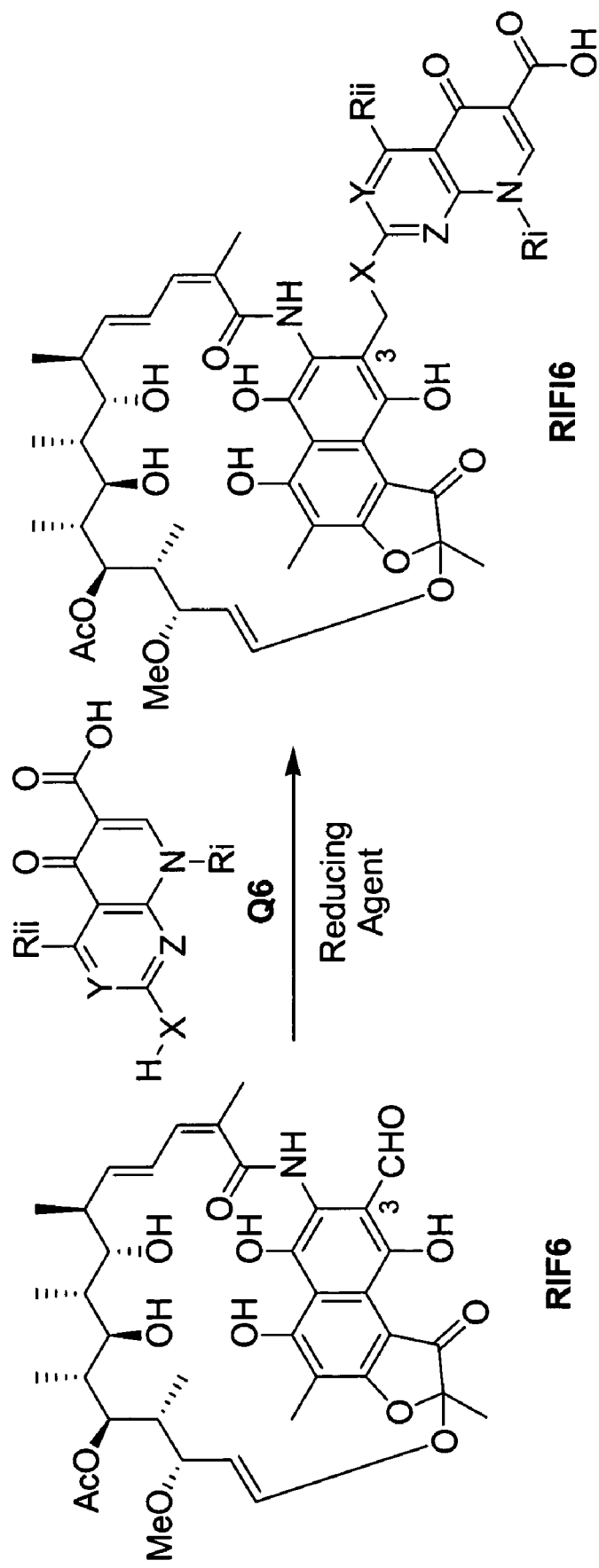
FIG. 12 shows Scheme 6, wherein a rifamycin derivative undergoes reductive amination with a quinolone compound.

One specific example for the synthesis of compounds of Formula I of this invention is illustrated by Scheme 6 in FIG. 12, wherein 3-formylrifamycin SV (RIF6) reacts with quinolone compounds (Q6) to give products (RIFI6) of the Formula I of this invention. It will be apparent to one skilled in the art that 3-formylrifamycin SV (RIF6) can be replaced by other rifamycin analogs of the Formula (RIF5) and the quinolone compound (Q6) can be replaced by other structures within the gyrase/topoisomerase IV inhibitor family. The reaction can be performed in a protic or aprotic solvent. Examples of solvents suitable for this reaction are THF, DMSO, DMF, NMP, ethanol, isopropanol, methanol, dioxane, acetonitrile, acetic acid, water, or any combination of the above. The most preferred solvent is methanol. Examples of reducing agents are sodium borohydride, sodium cyanoborohydride, and hydrogen in presence of a palladium catalyst. The most preferred reducing agent is sodium cyanoborohydride.

Figure 13:
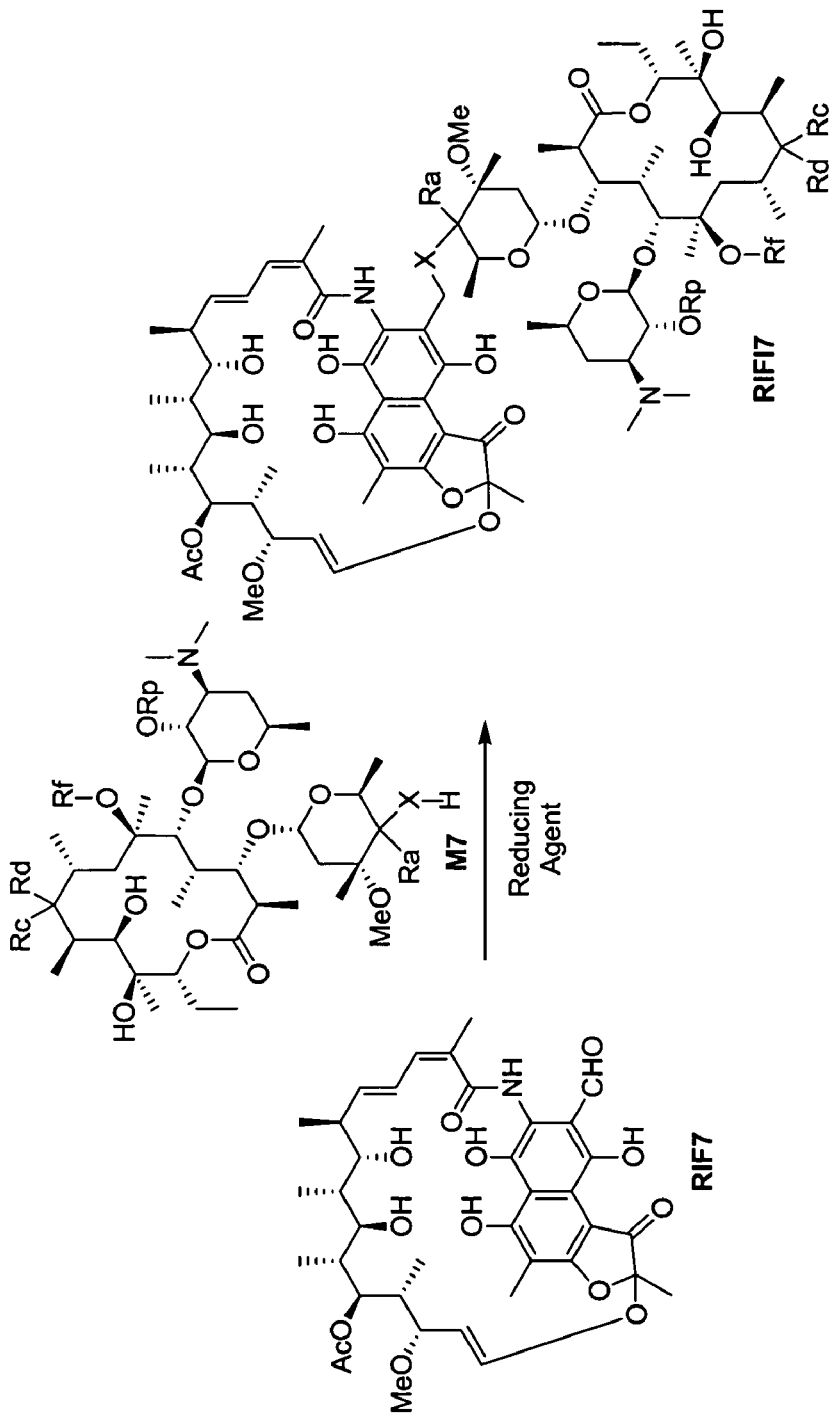
FIG. 13 shows Scheme 7, wherein a rifamycin derivative reacts with a macrolide compound.

Another specific example of compounds of Formula I of this invention is illustrated by Scheme 7 in FIG. 13, where 3-formylrifamycin SV (RIF7) reacts with a macrolide compound M7, wherein Rp is a hydrogen or a hydroxyl protecting group such as acetyl or benzoyl, to give product (RIFI7) of the Formula I of this invention. It will be apparent to one skilled in the art that 3-formylrifamycin SV (RIF7) can be replaced by other rifamycin analogs of the Formula RIF5 and the macrolide compound M7 can be replaced by other structures within the macrolide family that include 14-membered ring, 15-membered ring and 16-membered ring macrolide structures. It will be also apparent to one skilled in the art that the macrolide structure can be linked at other positions on macrolide such as the 6-position, the 9-position or the 11-position. The reaction is performed in a protic or aprotic solvent. Examples of solvents suitable for this reaction are THF, DMSO, DMF, NMP, ethanol, isopropanol, methanol, dioxane, acetonitrile, acetic acid, water, or any combination of the above. The most preferred solvent is methanol. Examples of reducing agents are sodium borohydride, sodium cyanoborohydride, and hydrogen in the presence of a palladium catalyst. The most preferred reducing agent is sodium cyanoborohydride.

Figure 14:
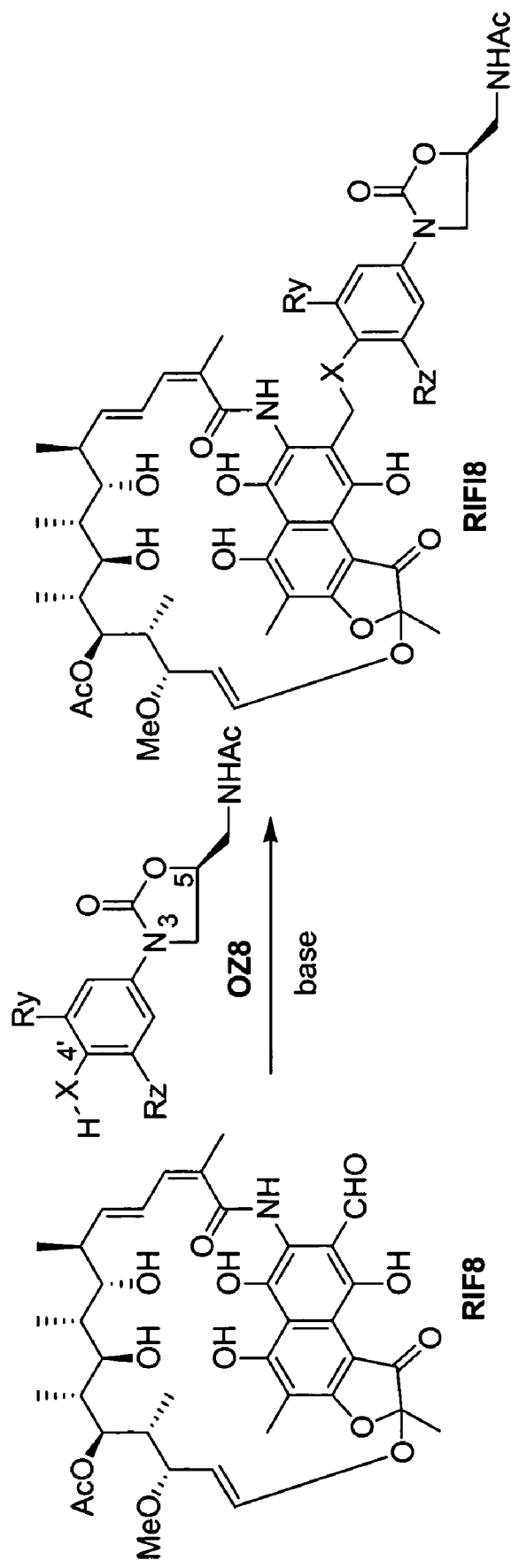
FIG. 14 shows Scheme 8, wherein a rifamycin derivative reacts with an oxazolidinone compound.

Yet another specific example of the current invention is illustrated by Scheme 8 in FIG. 14, where 3-formylrifamycin SV (RIF8) reacts with an oxazolidinone compound (OZ8), wherein $R_y$ and $R_z$ are independently selected from H or F, to give product (RIFI8) of the Formula I of this invention. It will be apparent to one skilled in the art that 3-formylrifamycin SV (RIF8) can be replaced by other rifamycin analogs of the Formula (RIF5) and the oxazolidinone compound (OZ8) can be replaced by other structures within the oxazolidinone class. Specific variations to the oxazolidinone structure can be made to the C-5 position as labeled on structure (OZ8). These variations have been described in detail by various authors (for example see: Hutchinson, D. K., *Current Topics in Medicinal Chemistry*, 2003, 3, 1021-1042, the entire content of which is hereby incorporated by reference). The reaction is performed in a protic or aprotic solvent catalyzed by an organic or inorganic base. Examples of solvents suitable for this reaction are THF, DMSO, DMF, NMP, ethanol, isopropanol, methanol, dioxane, acetonitrile, water, or any combination of the above. Examples of bases are $NaHCO_3$, $Na_2CO_3$, $KHCO_3$, $K_2CO_3$, $Cs_2CO_3$, NaOH, LiOH, TEA, Pyridine, DMAP, DBU, etc. Under certain circumstances, excess quinolones can be used as base.

Specific Compositions

The compounds of the current invention may be better understood with reference to the following specific examples, which are representative of some of the embodiments of the invention, and are not intended to limit the invention.

All starting material used in these specific examples were either purchased from commercial sources or prepared according to published procedures. Operations involving moisture and/or oxygen sensitive materials are conducted under an atmosphere of nitrogen. Flash chromatography is performed using silica gel 60 as normal phase adsorbent or C18 silica gel as reverse phase adsorbent. Thin layer chromatography ("TLC") and preparative thin layer chromatography ("PTLC") are performed using pre-coated plates purchased from E. Merck and spots are visualized with ultraviolet light followed by an appropriate staining reagent. Nuclear magnetic resonance ("NMR") spectra were recorded on a Varian 400 MHz magnetic resonance spectrometer. $^1H$ NMR chemical shift are given in parts-per million ($\delta$) downfield from TMS using the residual solvent signal ($CHCl_3=\delta$ 7.27, $CH_3OH=\delta$ 3.31) as internal standard. $^1H$ NMR information is tabulated in the following format: number of protons, multiplicity (s, singlet; d, doublet; t, triplet; q, quartet; m, multiplet; td, triplet of doublet; dt, doublet of triplet), coupling constant (s) (J) in hertz. The prefix app is occasionally applied in cases where the true signal multiplicity is unresolved and prefix br indicates a broad signal. Electro spray ionization mass spectra are recorded on a Finnegan LCQ advantage spectrometer.

EXAMPLE 4

3-[4-(3-Carboxy-1-cyclopropyl-6-fluoro-4-oxo-1,4-dihydroquinolin-7-yl)piperazin-1-yl]rifamycin S

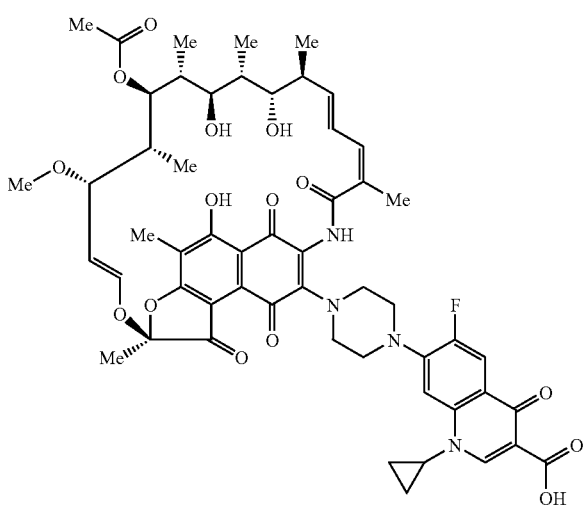

3-[4-(3-Carboxy-1-cyclopropyl-6-fluoro-4-oxo-1,4-dihydroquinolin-7-yl)piperazin-1-yl]rifamycin S was synthesized as follows: Step 1. 3-Bromorifamycin S: To a stirred solution of bromine (165 μL, 2.15 mmol) in EtOH (1 mL) at −40° C. was added pyridine (525 μL, 6.47 mmol). This was allowed to stir for 5 min at temperature between −40° and −5° C. To this was added rifamycin S (1.5 g. 2.15 mmol) in EtOH (32 mL) slowly and the resultant mixture was stirred at the same temperature for 30 min. It was diluted with EtOAc (100 mL), followed by addition of 0.1 N sodium thiosulfate (same volume). The aqueous layer was extracted with EtOAc (3×100 mL). The combined organic extracts were washed with 1 N HCl (100 mL), followed by water (100 mL), dried over anhydrous sodium sulfate and evaporated in vacuo to dryness to yield the title compound as an orange solid (1.6 g) (Reference: Egidio Marchi, Lauretta Montecchi, U.S. Pat. No. 4,179,438). ESI MS m/z 775 $(M+H)^+$; $^1H$ NMR (400 MHz, $CDCl_3$) δ 12.48 (s, 1H, OH), 8.15 (s, 1H, NH), 6.62 (dd, J=11.0 Hz, 15.6 Hz, 1H), 6.30 (d, J=10.9 Hz, 1H), 6.00 (dd, J=7.0 Hz, 15.6 Hz, 1H), 5.89 (d, J=13.2 Hz, 1H), 4.99-4.95 (m, 2H), 3.67 (d, J=10.4 Hz, 1H), 3.37 (m, 1H), 3.03 (s, 3H), 2.96 (d, J=8.8 Hz, 1H), 2.22 (s, 3H), 2.22 (m, 2H), 2.01 (s, 3H), 2.00 (s, 3H), 1.97 (s, 3H), 2.00 (m, 1H), 1.74-1.64 (m, 1H), 1.60-1.55 (m, 1H), 0.93 (d, J=7.0 Hz, 3H), 0.77 (d, J=6.9 Hz, 3H), 0.63 (d, J=7.1 Hz, 3H), 0.14 (d, J=7.1 Hz, 3H).

Step 2. Sodium 1-cyclopropyl-6-fluoro-4-oxo-7-(piperazin-1-yl)-1,4-dihydroquinoline-3-carboxylate (ciprofloxacin sodium): 1-Cyclopropyl-6-fluoro-4-oxo-7-(piperazin-1-yl)-1,4-dihydroquinoline-3-carboxylic acid (171 mg, 0.52 mmol) was dissolved completely in 5 mL of 1:1 mixture of MeOH and 0.2 N NaOH (1 equiv) with the aid of sonication. The solution was concentrated in vacuo to dryness and further dried under vacuum at 40° C. for 0.5 h to give product as a white powder.

Step 3. A solution of 3-bromorifamycin S (200 mg, 0.26 mmol) in DMSO (1 mL) was added to a stirred solution of ciprofloxacin sodium prepared as described in step 2 (0.52 mmol, 2.0 equiv) in DMSO (4 mL) at room temperature. The resulting black mixture was allowed to stir overnight, then concentrated in vacuo. The crude product was purified on a Biotage C18HS reverse phase column (3:1 mixture of acetonitrile and $H_2O$). The purple fractions were combined and concentrated in vacuo to afford a black amorphous solid (25 mg, 10%) after drying several hours under vacuum at 40° C. ESI MS m/z 1025 $(M+H)^+$; $^1H$ NMR (400 MHz, $CDCl_3$) δ 8.78 (s, 1H, quinolone), 8.03 (d, J=12.5 Hz, 1H, quinolone), 7.39 (d, J=6.6 Hz, 1H, quinolone), 7.15 (dd, J=16.1, 11.0 Hz, 1H), 6.39 (d, J=11.0, 1H), 6.21 (dd, J=16.1, 6.6 Hz, 1H), 6.06 (dd, J=12.5, 1.5 Hz, 1H), 5.12 (d, J=10.3 Hz, 1H), 5.11 (dd, J=12.5, 5.1, 1H), 3.99 (d, J=4.4, 1H), 3.93 (d, J=9.5 Hz, 1H), 3.78-3.64 (m, 4H), 3.61-3.48 (m, 5H), 3.27 (m, 2H), 3.11 (s, 3H, MeO), 3.05 (m, 1H), 2.34 (m, 1H), 2.28 (s, 3H, Me), 2.16 (s, 3H, Me), 2.09 (s+m, Me+2H), 2.04 (s, 3H, Me), 1.89-1.76 (br m, 2H), 1.75 (s, 3H, Me), 1.74-1.66 (br m, 3H), 1.44 (d, 2H, J=7.3 Hz), 1.22 (dt, 2H, J=11.7, 3.7 Hz), 0.98-0.88 (d, J=0.73, 3H, Me), 0.71 (d, J=6.6 Hz, 3H, Me), 0.20 (d, J=6.6 Hz, 3H, Me).

EXAMPLE 5

3-[4-(3-Carboxy-1-(2,4-difluorophenyl)-6-fluoro-4-oxo-1,4-dihydronaphthyridin-7-yl)piperazin-1-yl]rifamycin S

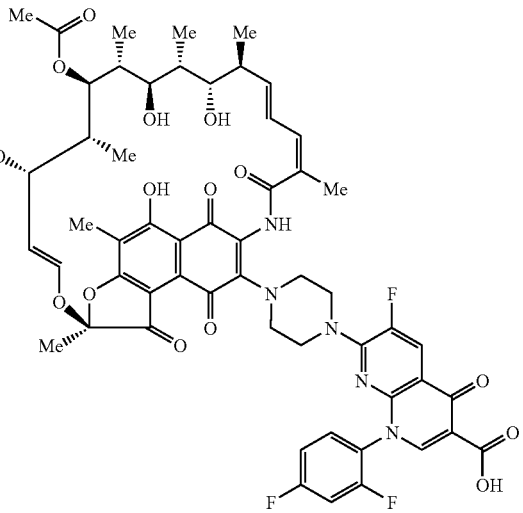

3-[4-(3-Carboxy-1-(2,4-difluorophenyl)-6-fluoro-4-oxo-1,4-dihydronaphthyridin-7-yl)piperazin-1-yl]rifamycin S was synthesized as follows: Step 1. Ethyl 1-(2,4-difluorophenyl)-6-fluoro-4-oxo-7-(piperazin-1-yl)-1,4-dihydronaphthyridine-3-carboxylate: Ethyl 7-chloro-1-(2,4-difluorophenyl)-6-fluoro-4-oxo-1,4-dihydronaphthyridine-3-carboxylate (766 mg, 2.0 mmol) and piperazine (430 mg, 5.0 mmol, 2.5 equiv) were dissolved in 20 mL of pyridine and allowed to stir at room temperature for 24 h. The solvent was removed in vacuo, and the crude product was taken up in $CH_2Cl_2$, washed with 5% aq $Na_2CO_3$, then water. The organic layer was dried ($Na_2SO_4$), evaporated in vacuo, and the resulting white solid was purified on silica gel column using a linear gradient (100% $CH_2Cl_2$ to 10% MeOH in $CH_2Cl_2$) to give a white solid. ESI MS m/z 433 $(M+H^+)$, 887 $(2M+Na^+)$; $^1H$ NMR (400 MHz, $CDCl_3$): δ 8.94 (s, 1H, quinolone), 8.12 (d, J=12.5 Hz, 1H, quinolone), 7.39 (app dd, J=13.3 Hz, 7.04 Hz, 1H, Ph), 7.26 (s, 1H, Ph), 7.04 (app q, J=15.7, 8.6 Hz, 1H, Ph), 4.36 (q, J=7.0, 2H, Et), 3.50 (app t, J=4.7 Hz, 4H, piperazine), 2.87 (app t, J=4.7 Hz, 4H, piperazine), 1.38 (t, J=7.0 Hz, 3H, Et).

Step 2. 1-(2,4-Difluorophenyl)-6-fluoro-4-oxo-7-(piperazin-1-yl)-1,4-dihydronaphthyridine-3-carboxylic Acid: The product from step 1 (230 mg, 0.52 mmol) was added to 4 mL of 4:1 MeOH and 0.8 N NaOH (~1.5 equiv) and heated at 65° C. for 5 h. The mixture was cooled, concentrated in vacuo, and partitioned between $CH_2Cl_2$ and water. The two-phase mixture was acidified with 5% citric acid to pH ~3, and the organic layer was separated. The aqueous was extracted with $CH_2Cl_2$ (3×10 mL), and the combined organic phases were dried ($MgSO_4$) and concentrated in vacuo to afford an off-white solid. The product was used for next step without further purification. ESI MS m/z 405 $(M+H^+)$, 831 $(2M+Na)$; $^1H$ NMR (400 MHz, DMSO-$d_6$): δ 6.82 (s, 1H), 8.27 (d, J=12.5 Hz, 1H), 7.83 (br m, 1H, Ph), 7.62 (br m, 1H, Ph), 7.36 (br s, 1H, Ph), 3.74 (br m, 4H, piperazine), 3.11 (br m, 4H, piperazine).

Step 3. 3-[4-(3-Carboxy-1-(2,4-difluorophenyl)-6-fluoro-4-oxo-1,4-dihydronaphthyridin-7-yl)piperazin-1-yl]rifamycin S: The title compound was prepared by using a similar procedure as described for the preparation of Example 4 except 1-(2,4-difluorophenyl)-6-fluoro-4-oxo-7-(piperazin-1-yl)-1,4-dihydronaphthyridine-3-carboxylic acid, prepared as described in step 2, was used instead of 1-cyclopropyl-6-fluoro-4-oxo-7-piperazin-1-yl-1,4-dihydro-quinoline-3-carboxylic acid (ciprofloxacin). The title compound was obtained as a black amorphous solid in 5% yield. ESI MS m/z 1098 (M+H$^+$).

EXAMPLE 6

3-[4-[3-[1-[3-Carboxy-1-(2,4-difluorophenyl)-6-fluoro-4-oxo-1,4-dihydronaphthyridin-7-yl]piperidin-4-yl]propyl]piperidin-1-yl]rifamycin S

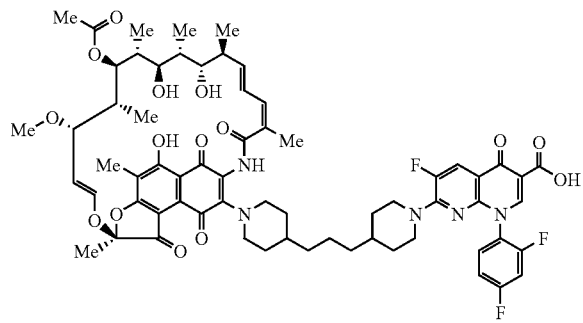

3-[4-[3-[1-[3-Carboxy-1-(2,4-difluorophenyl)-6-fluoro-4-oxo-1,4-dihydronaphthyridin-7-yl]piperidin-4-yl]propyl]piperidin-1-yl]rifamycin S was synthesized as follows: Step 1. 1-(2,4-Difluorophenyl)-6-fluoro-4-oxo-7-[4-[3-(piperidin-4-yl)propyl]piperidin-1-yl]-1,4-dihydronaphthyridine-3-carboxylic Acid: The title compound was prepared by using a similar procedure as described for the preparation of 1-(2,4-difluorophenyl)-6-fluoro-4-oxo-7-(piperazin-1-yl)-1,4-dihydronaphthyridine-3-carboxylic acid in Example 2 except 4,4'-trimethylenedipiperidine was used instead of piperazine. The title compound was obtained as an off-white solid, which was used without further purification.

Step 2. 3-[4-[3-[1-[3-Carboxy-1-(2,4-difluorophenyl)-6-fluoro-4-oxo-1,4-dihydronaphthyridin-7-yl]piperidin-4-yl]propyl]piperidin-1-yl]rifamycin S: The title compound was prepared by using a similar procedure as described for the preparation of Example 4 except 1-(2,4-difluorophenyl)-6-fluoro-4-oxo-7-[4-[3-(piperidin-4-yl)propyl]piperidin-1-yl]-1,4-dihydronaphthyridine-3-carboxylic acid was used in place of 1-cyclopropyl-6-fluoro-4-oxo-7-piperazin-1-yl-1,4-dihydro-quinoline-3-carboxylic acid (ciprofloxacin). The title compound was obtained as a black amorphous solid in 12% yield. ESI MS m/z 1090 (M$^+$–CH$_3$O).

EXAMPLE 7

(R/S)-3-[1-(3-Carboxy-8-chloro-1-cyclopropyl-6-fluoro-4-oxo-1,4-dihydroquinolin-7-yl)-pyrrolidin-3-ylamino]rifamycin S

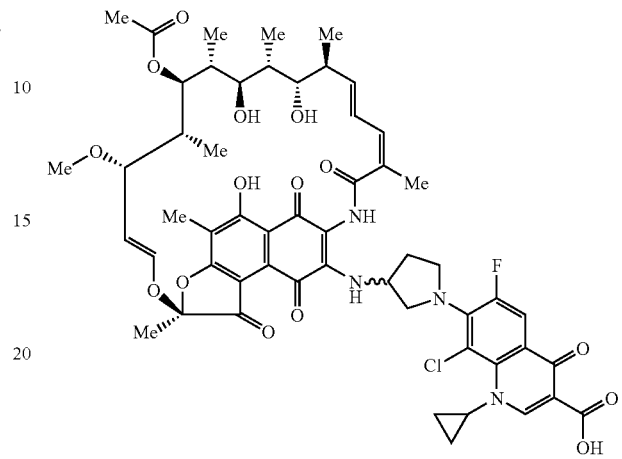

The title compound was prepared by using a similar procedure as the preparation of Example 4 except (R/S)-7-[3-aminopyrrolidin-1-yl]-8-chloro-1-cyclopropyl-6-fluoro-4-oxo-1,4-dihydro-quinoline-3-carboxylic acid hydrochloride (clinafloxacin hydrochloride) was used in the place of 1-cyclopropyl-6-fluoro-4-oxo-7-piperazin-1-yl-1,4-dihydro-quinoline-3-carboxylic acid (ciprofloxacin). The title compound was obtained as a black amorphous solid in 24% yield. ESI MS m/z 1059 (M+H$^+$), 1027 (M$^+$–MeO); $^1$H NMR 400 MHz, CDCl$_3$) δ 8.88 (d, J=8.1 Hz, 1 H), 7.94 (dd, J=19.8, 12.5 Hz, 1H), 7.74 (br s, 1H), 6.86 (br s, 1H), 6.35-6.29 (m, 1H), 6.20-6.10 (m, 1H), 6.05 (dd, J=11.0, 2.9 Hz, 1H), 5.10 (ddd, J=12.5, 5.9, 3.7 Hz, 1H), 5.00 (d, J=10.3 Hz, 1H), 4.52 (br s, 1H), 4.36-4.24 (m, 1H), 4.11-4.00 (m, 1H), 3.95 (app t, J=8.8 Hz, 1H), 3.85 (app t, J=18.8 Hz, 1H), 3.69-3.49 (m, 2H), 3.48-3.36 (m, 1H), 3.08 (s, 3H), 3.08-8.02 (m, 1H), 2.40-2.28 (m, 1H), 2.27 (d, J=5.1 Hz, 3H), 2.08 (d, J=8.1 Hz, 3H), 2.05 (s, 3H), 1.82-1.73 (m, 1H), 1.73 (s, 3H), 1.32-1.25 (m, 4H), 1.24 (s, 3H), 1.02 (dd, J=5.5, 6.6 Hz, 3H), 0.99-0.89 (m, 4H), 0.84 (d, J=6.6 Hz, 3H), 0.75 (br d, J=6.6 Hz, 3H), 0.67 (dd, J=6.6, 4.4 Hz, 3H), 0.08 (dd, J=6.6, 2.2 Hz, 3H).

EXAMPLE 8

(R)-3-[1-(3-Carboxy-1-cyclopropyl-6-fluoro-4-oxo-1,4-dihydroquinolin-7-yl)-pyrrolidin-3-ylamino]rifamycin S

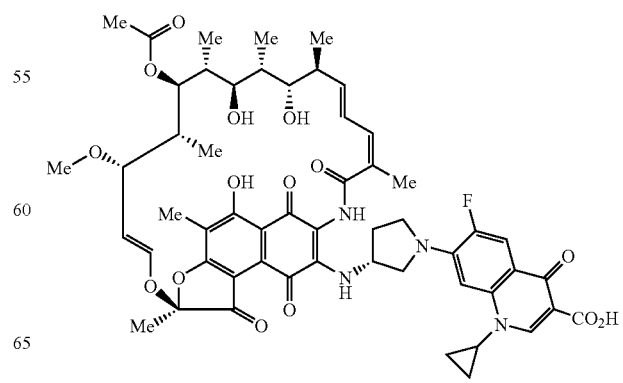

Step 1. (R)-7-(3-tert-Butoxycarbonylamino-pyrrolidin-1-yl)-1-cyclopropyl-6-fluoro-4-oxo-1,4-dihydro-quinoline-3-carboxylic acid: To a stirred solution of 7-chloro-1-cyclopropyl-6-fluoro-1,4-dihydro-4-oxoquinoline-3-carboxylic acid (756 mg, 2.68 mmol) in pyridine (30 ml) was added (R)-pyrrolidin-3-yl-carbamic acid tert-butyl ester (1.0 g, 5.36 mmol). This was heated at reflux for 48 hours. The reaction mixture was cooled to room temperature, MeOH (30 ml) was added to precipitate the title product as a white solid in 48% yield. ESI MS m/z 432 (M+H$^+$); $^1$H NMR (400 MHz, DMSO-d$_6$) δ 8.58 (s, 1H), 7.84 (d, J=14.8 Hz, 1H), 7.08 (d, J=7.8 Hz, 1H), 3.94-3.44 (m, 5H), 2.31 (m, 1H), 2.15 (m, 2H), 1.37 (s, 9H) 1.28 (n, 2H), 1.14 (m, 2H).

Step 2. (R)-7-(3-Amino-pyrrolidin-1-yl)-1-cyclopropyl-6-fluoro-4-oxo-1,4-dihydro-quinoline-3-carboxylic acid: To a stirred solution of the product from step 1 (300 mg, 0.69 mmol) in dioxane (10 mL), was added a solution of HCl in dioxane (4 M, 10 ml). After stirring for 2 hours, the solvent was evaporated in vacuo and the resultant product was used for next step without further purification. ESI MS m/z 332 (M+H$^+$); $^1$H NMR (400 MHz, DMSO-d$_6$) δ 8.58 (s, 1H), 8.47 (br s, 2H) 7.84 (d, J=14.0 Hz, 1H), 7.08 (d, J=7.8 Hz, 1H), 3.94-3.66 (m, 5H), 2.31 (m, 1H), 2.15 (m, 2H), 1.28 (m, 2H), 1.13 (m, 2H).

Step 3. (R)-3-[7-(3-Aminopyrrolidin-1-yl)-3-carboxy-1-cyclopropyl-6-fluoro-4-oxo-1,4-dihydroquinoline]rifamycin S: The title compound was prepared by using a similar procedure as described for the preparation of Example 4 except (R)-7-(3-aminopyrrolidin-1-yl)-1-cyclopropyl-6-fluoro-4-oxo-1,4-dihydroquinoline-3-carboxylic acid was used instead of 1-cyclopropyl-6-fluoro-4-oxo-7-piperazin-1-yl-1,4-dihydroquinoline-3-carboxylic acid (ciprofloxacin). The title compound was obtained as a black solid in 32% yield. ESI MS m/z 1025 (M+H$^+$); $^1$H NMR (400 MHz, DMSO-d$_6$) δ 8.49 (s, 1H), 7.74 (m, 1H), 6.89 (m, 1H), 6.20 (m, 1H), 5.89 (m, 2H), 5.84 (d, J=10.9 Hz, 1H), 5.76 (m, 1H), 5.66 (m, 1H), 5.16 (m, 1H), 4.72 (m, 1H), 4.03 (m, 1H), 3.93 (m, 1H), 3.74 (m, 1H), 3.62 (m, 1H), 3.07 (m, 4H), 2.95 (m, 2H), 2.89 (m, 3H), 2.84 (m, 6H), 2.08 (m, 2H), 1.85 (m, 8H), 1.57-1.03 (m, 4H), 0.78-0.51 (m, 13H), 0.00 (m, 3H).

EXAMPLE 9

(S)-3-[1-(3-Carboxy-1-cyclopropyl-6-fluoro-4-oxo-1,4-dihydroquinolin-7-yl)-pyrrolidin-3-ylamino]rifamycin S

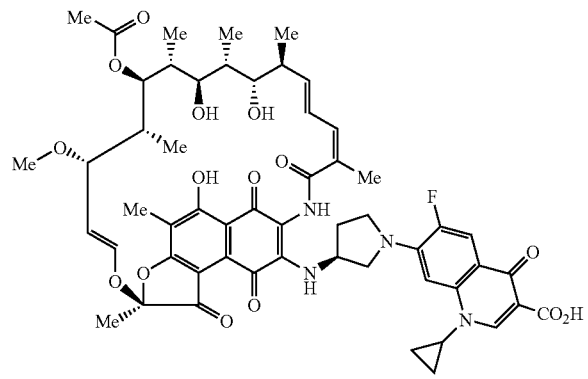

The title compound was prepared by using the same procedure as described for the preparation of Example 8 except (S)-pyrrolidin-3-yl-carbamic acid tert-butyl ester was used in place of (R)-pyrrolidin-3-yl-carbamic acid tert-butyl ester. ESI MS m/z 1041 (M+H$^+$); $^1$H NMR (400 MHz, DMSO-d$_6$) δ 13.23 (s, 1 H), 9.77 (s, 1 H), 8.93 (s, 1 H) 8.19 (d, J=14.0 Hz, 1 H), 7.42 (s, 1 H), 6.64 (m, 3 H), 5.41 (m, 1 H), 5.25 (m, 2 H), 4.45-3.88 (m, 10 H), 3.58 (m, 1 H), 3.28-2.90 (m, 4 H), 3.22 (s, 3 H), 3.09 (s, 3 H), 3.06 (s, 3 H) 2.99 (s, 3 H), 2.76-2.60 (m, 4 H), 2.53-2.14 (m, 5 H), 1.69-1.40 (m, 6 H), 1.28-1.03 (m, 4 H), 0.85 (m, 3 H), 0.00 (m, 3 H).

EXAMPLE 10

(R,S)-3-[4-(3-Carboxy-1-cyclopropyl-6-fluoro-8-methoxy-4-oxo-1,4-dihydroquinolin-7-yl)-2-methylpiperazin-1-yl]rifamycin S

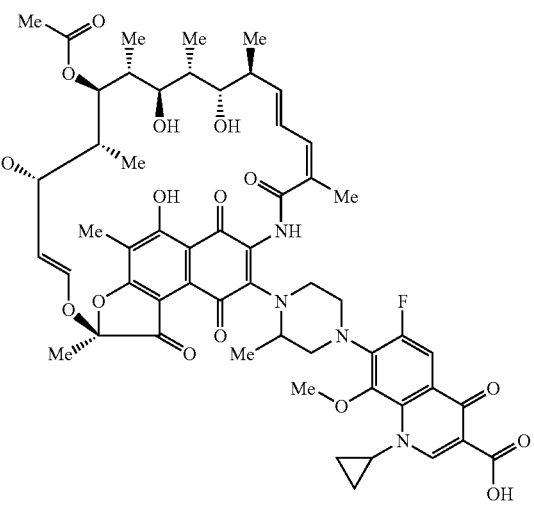

(R/S)-1-Cyclopropyl-6-fluoro-8-methoxy-7-(3-methyl-piperazin-1-yl)-4-oxo-1,4-dihydro-quinoline-3-carboxylic acid (gatifloxacin, 32 mg, 0.089 mmol) was suspended in 1.5 mL ethanol and 0.3 mL water at room temperature. To this suspension was added sodium bicarbonate (22 mg, 0.26 mmol), followed by addition of 3-bromorifamycin S (20 mg, 0.026 mmol). The mixture was allowed to stir at room temperature for 80 hours, and partitioned between dichloromethane and 10% citric acid. The separated organic layer was washed with 10% citric acid, dried over sodium sulfate, concentrated in vacuo to afford a dark brown solid, which was purified by preparative thin layer chromatography (100% ethyl acetate) to give the title compound as a purple black solid (2.7 mg, 10%). ESI MS m/z 1069 (M+H$^+$); $^1$HNMR (400 MHz, CDCl$_3$) δ 13.21 (2s, 1 H), 8.82 (s, 1H), 7.88 (2d, 1H), 7.51 (s, 1H), 7.30 (m, 1 H), 6.40 (m, 1H), 6.16 (m, 1H), 6.08 (m, 1H), 5.12 (m 2H), 3.97 (m, 3H), 3.69 (2s, 3H), 3.64-3.28 (complex pattern, 6H), 3.15 (2s, 3H), 3.05 (m, 1H), 2.37 (m, 3H), 2.28 (s, 3H), 2.13 (2s, 3H), 2.08 (s, 3H), 1.81 (m, 2H), 1.75 (s, 3H), 1.68 (m, 1H), 1.49 (m, 3H), 1,20 (m, 2H), 1.04 (2d, 3H), 0.98 (m, 2H), 0.84 (2d, 3H), 0.71 (2d, 3H), 0.20 (2d, 3H).

EXAMPLE 11

(R,S)-3-[4-(3-Carboxy-1-ethyl-6,8-difluoro-4-oxo-1,4-dihydroquinolin-7-yl)-2-methyl-piperazinyl]rifamycin SV

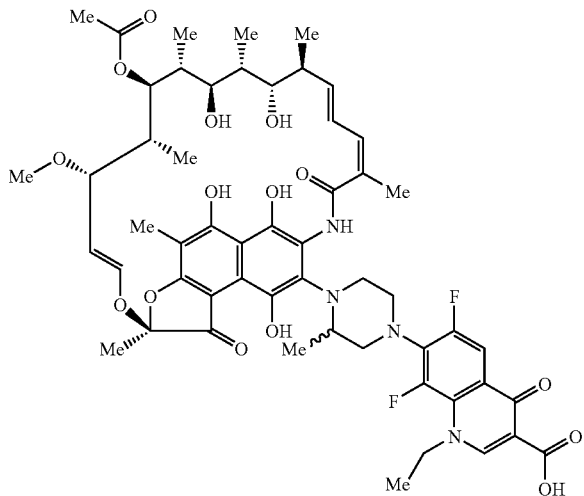

The title compound was prepared by using the same procedure as described for the preparation of Example 10 except (R/S)-1-ethyl-6,8-difluoro-7-(3-methylpiperazin-1-yl)-4-oxo-1,4-dihydroquinoline-3-carboxylic acid hydrochloride (lomefloxacin hydrochloride) was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a purple black solid in 14% yield. ESI MS m/z 1045 (M+H$^+$); $^1$H NMR (400 MHz, CDCl$_3$) δ 13.19 (s, 1H), 8.61 (s, 1H), 7.98 (d, J=11.1 Hz, 1H), 7.51 (s, 1H), 7.18 (m, 1H), 6.40 (d, J=10.7 Hz, 1H), 6.16 (dd, J=15.5 Hz and 6.2 Hz, 1H), 6.08 (d, J=11.0 Hz, 1H), 5.10 (m, 2H), 4.46 (m, 2H), 4.10 (br s, 1H), 3.96 (m, 2H), 3.72-3.32 (complex pattern, 6H), 3.10 (s, 1H), 3.06 (m, 1H), 2.36 (m, 1H), 2.28 (s, 3H), 2.10 (m, 6H), 1.89-1.42 (complex pattern, 10H), 1.04 (d, J=6.2 Hz, 3H), 0.87 (d, J=6.3 Hz, 3H), 0.71 (d, J=6.0 Hz, 3H), 0.19 (d, J=7.1 Hz, 3H).

EXAMPLE 12

3-[4-[3-Carboxy-1-cyclopropyl-6-fluoro-4-oxo-(1,4-dihydroquinolin-7-yl)]-piperazin-1-ylmethyl]rifamycin SV

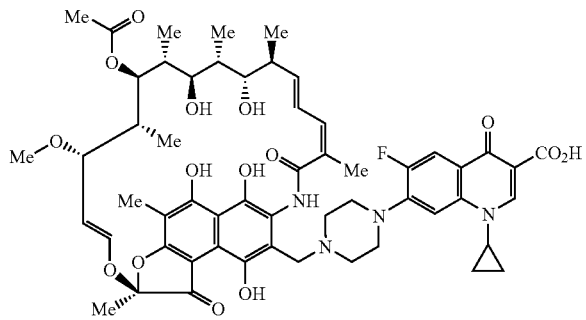

To a stirred solution of 3-formylrifamycin (350 mg, 0.48 mmol) in methanol (25 mL) at room temperature was added 1-cyclopropyl-6-fluoro-4-oxo-7-(piperazin-1-yl)-1,4-dihydro-quinoline-3-carboxylic acid (ciprofloxacin) (200 mg, 0.60 mmol), followed by acetic acid (0.2 mL). The suspension was allowed to stir at room temperature for 30 min, sodium cyanoborohydride (200 mg, 3.1 mmol) was added and stirring was maintained at room temperature for 18 h. The resultant solution was partitioned between dichloromethane and 5% citric acid solution. This was shaken and organic layer was separated, dried over sodium sulfate, concentrated in vacuo to dryness. The crude product was purified by preparative thin layer chromatography (1% acetic acid in ethyl acetate) to give the title compound as an orange solid (100 mg, 22%). ESI MS m/z 1041.4 (M+H$^+$); $^1$H NMR (400 MHz, CDCl$_3$) δ 13.7 (bs 1 H), 13.0 (bs, 1 H), 12.5 (bs, 1 H), 12.1 (bs, 1 H), 9.0 (s, 1 H), 8.25 (d, 1 H), 7.65 (bs, 1 H), 6.80 (m, 1 H), 6.60 (m, 2 H), 6.30 (m, 1 H), 5.40 (m, 1 H), 5.25 (m, 1 H), 4.60 (bs, 1 H), 3.4-4.2 (complex m.), 3.40 (s, 3 H), 2.45 (s, 3 H), 2.10 (s, 3 H), 1.40 (d, 3 H), 1.20 (d, 2 H), 1.0 (bd, 3 H), 0.05 (bd, 3 H).

EXAMPLE 13

(R/S)-3-[1-(8-Chloro-3-carboxy-1-cyclopropyl-6-fluoro-4-oxo-1,4-dihydroquinolin-7-yl)-pyrrolidinyl-3-aminomethyl]rifamycin SV

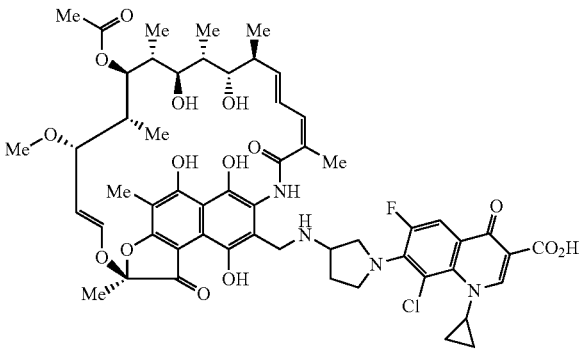

The title compound was prepared by using the same procedure as described for the preparation of Example 12 except (R/S)-7-(3-aminopyrrolidin-1-yl)-8-chloro-1-cyclopropyl-6-fluoro-4-oxo-1,4-dihydroquinoline-3-carboxylic acid hydrochloride (clinafloxacin hydrochloride) was used in place of 1-cyclopropyl-6-fluoro-4-oxo-7-piperazin-1-yl-1,4-dihydro-quinoline-3-carboxylic acid (ciprofloxacin). The title compound was obtained as an orange solid in 54% yield. ESI MS m/z 1075.3 (M+H$^+$); $^1$H NMR (CD$_3$OD) δ 9.20 (s, 1 H), 8.10 (m, 1 H), 6.95 (m, 1 H), 6.60 (m, 1 H), 6.45 (m, 1 H), 4.40 (m, 1 H), 4.30 (m, 1 H), 4.91 (d, 1 H), 4.65 (bs, 1 H), 4.50 (bs, 1 H), 3.90-4.30 (complex pattern), 3.30 (s, 3 H), 2.30 (m, 6 H), 1.25 (m, 6 H), 0.90 (m, 3 H), 0.00 (m, 3 H).

EXAMPLE 14

3-[4-[3-carboxy-1-(2,4-Difluoro-phenyl)-6-fluoro-4-oxo-1,4-dihydro-[1,8]naphthyridin-7-yl]piperazin-1-ylmethyl]rifamycin SV

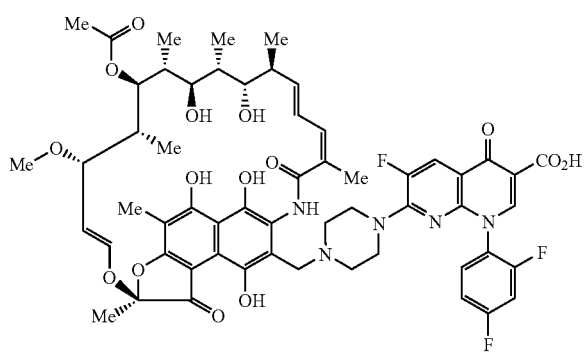

The title compound was prepared by using the same procedure as described for the preparation of Example 12 except 1-(2,4-difluorophenyl)-6-fluoro-7-(piperazin-1-yl)-4-oxo-1,4-dihydro-[1,8]naphthyridine-3-carboxylic acid was used in place of 1-cyclopropyl-6-fluoro-4-oxo-7-(piperazin-1-yl)-1,4-dihydro-quinoline-3-carboxylic acid (ciprofloxacin). The title compound was obtained as an orange solid in 2% yield. ESI MS m/z 1114.4 (M+H$^+$).

EXAMPLE 15

(R)-3-[1-(3-carboxy-1-cyclopropyl-6-fluoro-4-oxo-1,4-dihydroquinolin-7-yl)-pyrrolidinyl-3-aminomethyl]rifamycin SV

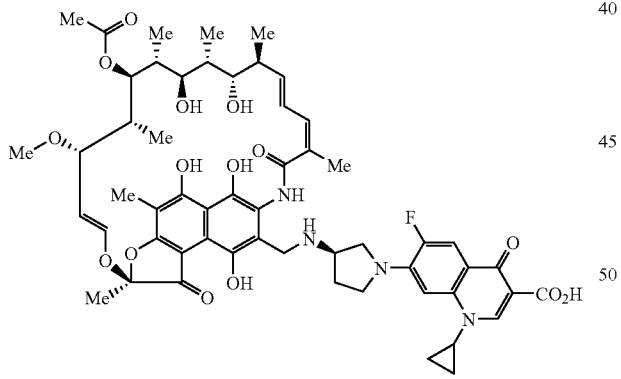

The title compound was prepared by using the same procedure as described for the preparation of Example 12 except (R)-7-(3-amino-pyrrolidin-1-yl)-1-cyclopropyl-6-fluoro-4-oxo-1,4-dihydro-quinoline-3-carboxylic acid was used in place of 1-cyclopropyl-6-fluoro-4-oxo-7-piperazin-1-yl-1,4-dihydro-quinoline-3-carboxylic acid (ciprofloxacin). The title compound was obtained as an orange solid in 10% yield. ESI MS m/z 1041 (M+H$^+$); $^1$H NMR (400 MHz, DMSO-d$_6$) δ 13.23 (s, 1H), 9.77 (s, 1H), 8.93 (s, 1H) 8.19 (d, J=14.0 Hz, 1H), 7.42 (s, 1H), 6.64 (m, 3H), 5.41 (m, 1H), 5.25 (m, 2H), 4.45-3.88 (m, 10H), 3.58 (m, 1H), 3.28-2.90 (m, 4H), 3.22 (s, 3H), 3.09 (s, 3H), 3.06 (s, 3H) 2.99 (s, 3H), 2.76-2.60 (m, 4H), 2.53-2.14 (m, 5H), 1.69-1.40 (m, 6H), 1.28-1.03 (m, 4H), 0.85 (m, 3H), 0.00 (m, 3H)

EXAMPLE 16

(S)-3-[1-(3-carboxy-1-cyclopropyl-6-fluoro-4-oxo-1,4-dihydroquinolin-7-yl)-pyrrolidinyl-3-aminomethyl]rifamycin SV

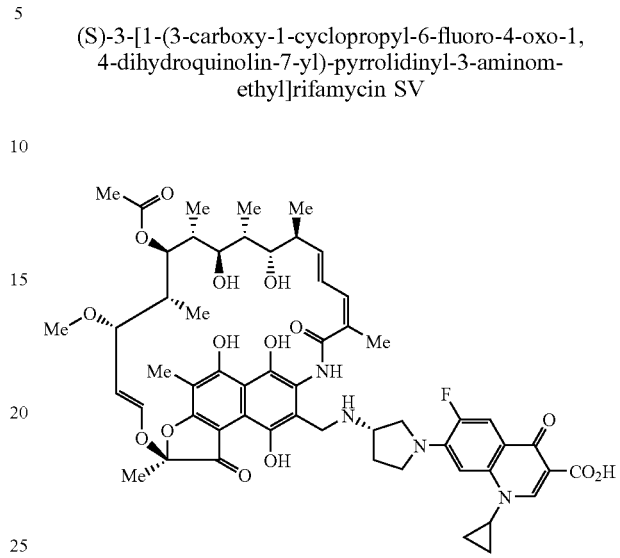

The title compound was prepared by using the same procedure as the preparation of Example 12 except (S)-7-(3-aminopyrrolidin-1-yl)-1-cyclopropyl-6-fluoro-4-oxo-1,4-dihydro-quinoline-3-carboxylic acid was used instead of 1-cyclopropyl-6-fluoro-4-oxo-7-piperazin-1-yl-1,4-dihydro-quinoline-3-carboxylic acid (ciprofloxacin). The title compound was obtained as an orange solid in 10% yield. ESI MS m/z 1041 (M+H$^+$); $^1$H NMR (400 MHz DMSO-d$_6$) δ 13.29 (s, 1H), 8.95 (s, 1H) 8.17 (d, J=14.0 Hz, 1H), 7.41 (s, 1H), 6.60 (m, 2H), 6.46 (m, 1H), 5.44-5.39 (m, 2H), 4.31 (d, J=8.6 Hz, 1H), 4.15-3.92 (m, 7H), 3.58 (d, J=8.6 Hz, 1H), 3.23 (s, 3H), 3.17 (m, 2H), 1.98 (s, 3H), 1.90 (s, 4H), 1.70 (m, 8H), 1.64 (s, 3H), 1.25 (m, 2H), 1.11 (m, 4H), 0.87 (m, 10H), 0.52 (m, 3H), 0.00 (m, 3H).

EXAMPLE 17

3-(Clarithromycin-4″-ylcarbamylethylamino)rifamycin S

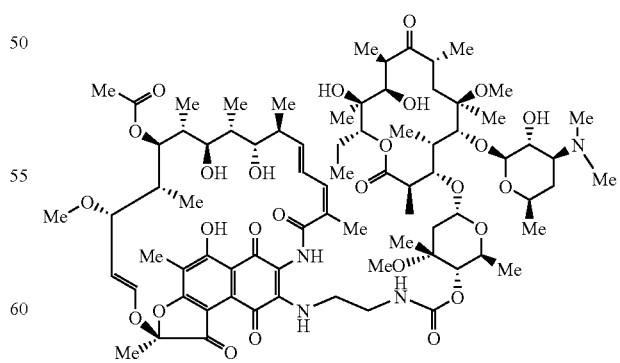

Step 1. 2′-Acetoxyclarithromycin: To a stirred solution of clarithromycin (417 mg, 0.56 mmol) in CH$_2$Cl$_2$ (8.0 mL) was added triethylamine (0.2 mL, 1.47 mmol) and acetic anhydride (75 μL, 0.74 mmol). The resultant solution was allowed to stir at room temperature for two days, and partitioned between ethyl acetate and water. The separated organic layer was washed with brine, dried over Na$_2$SO$_4$, and concentrated in vacuo to afford product as a white solid (440 mg, 99%). ESI MS m/z 790.4 (M+H$^+$); $^1$H NMR (400 MHz, CDCl$_3$): δ (ppm) 5.06 (dd, J=2.0, 10.8 Hz, 1H), 4.94 (d, J=4.8 Hz, 1H), 4.75 (dd, J=7.2, 10.8 Hz, 1H), 4.67 (d, J=7.6 Hz, 1H), 3.99 (s, 1H), 3.95-4.01 (m, 1H), 3.76 (d, J=8.8 Hz, 1H), 3.75 (s, 1H), 3.61 (d, J=8.0 Hz, 1H), 3.45-3.50 (m, 1H), 3.37 (s, 3H), 3.21 (s, 1H), 3.06 (d, J=9.6 Hz, 1H), 3.02 (s, 3H), 2.97 (app q, J=6.8 Hz, 1H), 2.83-2.88 (m, 1H), 2.55-2.63 (m, 2H), 2.36 (d, J=15.2 Hz, 1H), 2.26 (s, 6H), 2.17 (d, J=10.0 Hz, 1H), 2.06 (s, 3H), 1.84-1.96 (m, 2H), 1.58-1.74 (m, 5H), 1.44-1.50 (m, 1H), 1.38 (s, 3H), 1.30 (d, J=6.0 Hz, 3H), 1.23 (d, J=6.4 Hz, 3H), 1.28 (s, 3H), 1.21 (d, J=8.0 Hz, 3H), 1.14 (d, J=6.4 Hz, 3H), 1.13 (s, 3H), 1.12 (d, J=6.0 Hz, 3H), 0.93 (d, J=7.6 Hz, 3H), 0.84 (t, J=7.2 Hz, 3H).

Step 2. 2'-Acetoxy-4''-aminoethylaminocarbonyl-clarithromycin: To a stirred solution of the product from step 1 (440 mg, 0.56 mmol) in toluene (10.0 mL) and dichloroethane (1.5 mL) was added sequentially potassium carbonate (235 mg, 1.70 mmol) and 1,1'-carbonyldiimidazole (135 mg, 0.83 mmol). The mixture was allowed to stir at 37° C. overnight, and ethylenediamine (2.0 mL, 30 mmol) was added. The resultant mixture was allowed to stir at 40° C. for 1 h and partitioned between ethyl acetate and water. The separated organic layer was washed with brine and dried over Na$_2$SO$_4$ to afford product as a white solid (440 mg, 90%), which was used for next step without further purification. ESI MS m/z 876.4 (M+H$^+$); $^1$H NMR (400 MHz, CDCl$_3$) δ (ppm) 7.18 (dd, J=2.8, 7.6 Hz, 1H), 5.17 (app t, J=5.2 Hz, 1H), 5.07 (dd, J=2.0, 11.2 Hz, 1H), 4.98 (d, J=4.8 Hz, 1H), 4.76 (dd, J=7.2, 11.2 Hz, 1H), 4.66 (d, J=7.2 Hz, 1H), 4.54 (d, J=10.0 Hz, 1H), 4.25-4.29 (m, 1H), 3.99 (s, 1H), 3.76 (d, J=8.8 Hz, 1H), 3.74 (s, 1H), 3.66-3.71 (m, 1H), 3.61 (d, J=7.6 Hz, 1H), 3.36 (s, 3H), 3.26 (app q, J=6.0 Hz, 2H), 3.21 (br s, 1H), 3.02 (s, 3H), 2.99 (app q, J=6.8 Hz, 1H), 2.81-2.89 (m, 3H), 2.73 (dt, J=4.0, 11.2 Hz, 1H), 2.54-2.58 (m, 1H), 2.41 (d, J=15.2 Hz, 1H), 2.29 (s, 6H), 2.27 (d, J=8.0 Hz, 1H), 2.05 (s, 3H), 1.86-1.96 (m, 2H), 1.58-1.73 (m, 4H), 1.46-1.52 (m, 1H), 1.36 (s, 3H), 1.27-1.32 (m, 1H), 1.18-1.22 (m, 12H), 1.11-1.14 (m, 9H), 0.94 (d, J=7.2 Hz, 3H), 0.84 (t, J=7.6 Hz, 3H).

Step 3. 3-(Clarithromycin-4''-ylcarbamylethylamino)rifamycin S: To a stirred solution of the product from step 2 (181 mg, 0.21 mmol) in EtOH (2.3 mL) and dichloroethane (1.1 mL) was added triethylamine (0.17 mL, 1.23 mmol) followed by 3-bromorifamycin (257 mg, 0.33 mmol). The resultant mixture was allowed to stir at room temperature for 1 hour, and partitioned between ethyl acetate and water. The separated organic layer was washed with brine, dried over Na$_2$SO$_4$ and concentrated in vacuo. The residue was purified by silica gel chromatography (5%-10% MeOH/CH$_2$Cl$_2$) to afford a dark purple solid (250 mg). This was dissolved in MeOH and heated at 45° C. overnight. Evaporation of the solvent in vacuo gave the product as a dark purple solid (220 mg, 70%). ESI MS m/z 1527.9 (M+H$^+$); $^1$H NMR (400 MHz, CDCl$_3$) δ (ppm) 13.30 (br s, 1H), 7.66 (s, 1H), 6.84 (t, J=12.8 Hz, 1H), 6.48 (s, 1H), 6.32 (d, J=10.8 Hz, 1H), 6.14 (dd, J=6.8, 11.6 Hz,1H), 6.06 (dd, J=1.2, 12.4 Hz, 1H), 5.19 (br s, 1H), 5.10 (dd, J=5.6, 12.4 Hz, 1H), 5.05 (dd, J=1.6, 10.8 Hz, 1H), 5.01 (d, J=12.0 Hz, 1H), 4.94 (d, J=4.8 Hz, 1H), 4.49 (d, J=9.2 Hz, 2H), 4.30-4.24 (m, 1H), 3.98 (s, 1H), 3.93 (d, J=5.2 Hz, 1H), 3.85 (d, J=9.6 Hz, 1H), 3.75 (d, J=7.2 Hz, 1H), 3.74 (s, 1H), 3.64-3.56 (m, 5H), 3.47 (s, 3H), 3.47-3.43 (m, 2H), 3.41-3.36 (m, 1H), 3.32 (d, J=2.0 Hz, 1H), 3.28 (s, 3H), 3.18 (s, 3H), 3.08 (s, 3H), 3.04-2.96 (m, 3H), 3.02 (s, 3H), 2.92-2.84 (m, 1H), 2.58-2.54 (m, 2H), 2.41-2.26 (m, 2H), 2.30 (s, 3H), 2.28 (s, 3H), 2.07 (s, 3H), 2.06 (s, 3H), 1.93-1.88 (m, 2H), 1.84-1.78 (m, 1H), 1.73 (s, 3H), 1.72-1.59 (m, 5H), 1.50-1.44 (m, 1H), 1.37 (s, 3H), 1.21-1.10 (m, 24H), 1.03 (d, J=6.8 Hz, 3H), 0.85 (d, J=7.2 Hz, 3H), 0.83 (t, J=7.2 Hz, 3H), 0.67 (d, J=6.8 Hz, 3H), 0.07 (d, J=7.2 Hz, 3H).

EXAMPLE 18

(R)-3-[3-(Clarithromycin-4''-ylcarbamylamino)-pyrrolidin-1-yl]-rifamycin S

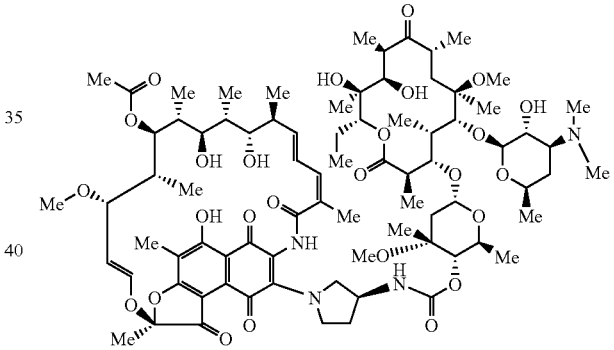

The title compound was prepared by following the same procedure as described for the preparation of Example 17 except (R)-(+)-3-aminopyrrolidine was used in place of ethylene diamine. The title product was obtained as a dark purple solid in 38% yield. ESI MS m/z 1553.9 (M+H$^+$); $^1$H NMR (400 MHz, CDCl$_3$) δ (ppm) 13.37 (br s, 1H), 7.92 (br s, 1H), 7.76 (s, 1H), 6.80-6.60 (m, 2H), 6.32 (d, J=10.0 Hz, 1H), 6.17-6.07 (m, 2H), 5.16-5.11 (m, 1H), 5.07 (dd, J=1.6, 10.8 Hz, 1H), 4.99 (d, J=4.0 Hz, 2H), 4.50 (br s, 1H), 4.36-4.32 (m, 2H), 3.98 (s, 1H), 3.92-3.80 (m, 2H), 3.77-3.62 (m, 5H), 3.53-3.45 (m, 5H), 3.35 (d, J=8.4 Hz, 1H), 3.32 (s, 3H), 3.22-3.18 (m, 2H), 3.19 (s, 1H), 3.10 (s, 3H), 3.07-2.99 (m, 3H), 3.04 (s, 3H), 2.91 (t, J=8.4 Hz, 1H), 2.60-2.42 (m, 2H), 2.38-2.18 (m, 4H), 2.30 (s, 3H), 2.07 (s, 6H), 1.97-1.60 (m, 10H), 1.74 (s, 3H), 1.52-1.46 (m, 1H), 1.38 (s, 3H), 1.25-1.12 (m, 27H), 1.05 (d, J=7.2 Hz, 3H), 0.86 (d, J=7.2 Hz, 3H), 0.84 (t, J=7.2 Hz, 3H), 0.69 (d, J=6.8 Hz, 3H), 0.09 (d, J=7.2 Hz, 3H).

EXAMPLE 19

(S)-3-[3-(Clarithromycin-4''-ylcarbamylamino)-pyrrolidin-1-yl]rifamycin S

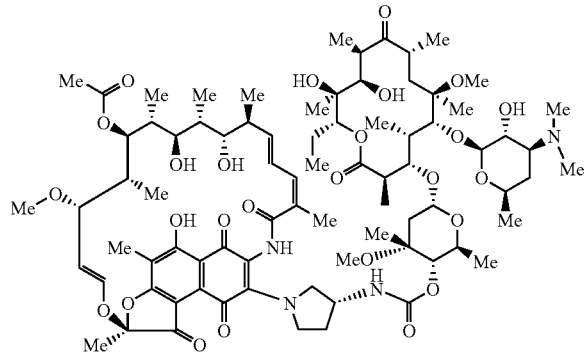

The title compound was prepared by following the same procedure as described for the preparation of Example 17 except (S)-(−)-3-aminopyrrolidine was used in place of ethylene diamine. The title product was obtained as a dark purple solid in 47% yield. ESI MS m/z 1553.9 (M+H⁺); $^1$H NMR (400 MHz, CDCl$_3$) δ (ppm) 13.49 (s, 1H), 7.90 (br s, 1H), 7.68 (br s, 1H), 6.85 (br s, 1H), 6.46 (br s, 1H), 6.33 (d, J=7.2 Hz, 1H), 6.16 (dd, J=6.4, 15.6 Hz, 1H), 6.08 (d, J=12.4 Hz, 1H), 5.10 (dd, J=2.8, 12.4 Hz, 1H), 5.06 (dd, J=2.0, 10.8 Hz, 1H), 5.01 (d, J=10.4 Hz, 1H), 4.96 (d, J=4.8 Hz, 1H), 4.61 (d, J=7.2 Hz, 1H), 4.60-4.55 (m, 1H), 4.50 (d, J=5.6 Hz, 1H), 4.37-4.31 (m, 2H), 3.97 (s, 1H), 3.93 (d, J=5.6 Hz, 1H), 3.86 (d, J=9.6 Hz, 1H), 3.76 (s, 1H), 3.73 (d, J=9.2 Hz, 1H), 3.66-3.48 (m, 5H), 3.35-3.30 (m, 2H), 3.30 (s, 3H), 3.22-3.17 (m, 2H), 3.09 (s, 3H), 3.05-2.98 (m, 3H), 3.02 (s, 3H), 2.93-2.87 (m, 1H), 2.60-2.50 (m, 2H), 2.38-2.28 (m, 4H), 2.29 (s, 6H), 2.06 (s, 6H), 1.95-1.89 (m, 2H), 1.82-1.58 (m, 6H), 1.74 (s, 3H), 1.52-1.42 (m, 1H), 1.38 (s, 3H), 1.35-1.32 (m, 1H), 1.21-1.09 (m, 24H), 1.05 (s, 3H), 1.03 (d, J=7.2 Hz, 3H), 0.87 (d, J=7.2 Hz, 3H), 0.83 (t, J=7.2 Hz, 3H), 0.69 (d, J=6.8 Hz, 3H), 0.08 (d, J=7.2 Hz, 3H).

EXAMPLE 20

3-[4-(Clarithromycin-41'-ylcarbonyl)-piperazin-1-yl]rifamycin S

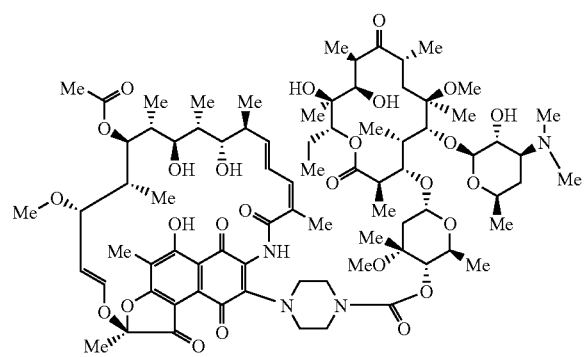

The title compound was prepared by following similar procedure as described for the preparation of Example 17 except piperazine was used in place of ethylene diamine. The title product was obtained as a dark purple solid in 23% yield. ESI MS m/z 1553.8 (M+H⁺); $^1$HNMR (400 MHz, CDCl$_3$) δ (ppm) 13.10 (br s, 1H), 7.61 (s, 1H), 6.38 (d, J=10.2 Hz, 1H), 6.18 (dd, J=6.4, 16.4 Hz, 1H), 6.06 (dd, J=1.2, 12.4 Hz, 1H), 5.12-5.04 (m, 3H), 4.98 (d, J=5.2 Hz, 1H), 4.62 (d, J=7.2 Hz, 1H), 4.56 (d, J=9.6 Hz, 1H), 4.35-4.30 (m, 1H), 3.96 (s, 2H), 3.90 (d, J=10.0 Hz, 1H), 3.76-3.70 (m, 4H), 3.66-3.64 (m, 2H), 3.54-3.41 (m, 8H), 3.33 (s, 3H), 3.33-3.18 (m, 4H), 3.10 (s, 3H), 3.08-2.98 (m, 2H), 3.03 (s, 3H), 2.93-2.88 (m, 1H), 2.59-2.50 (m, 4H), 2.41-2.32 (m, 5H), 2.27 (s, 3H), 2.11 (s, 3H), 2.08 (s, 3H), 1.96-1.89 (m, 2H), 1.87-1.78 (m, 3H), 1.74 (s, 3H), 1.68-1.57 (m, 6H), 1.52-1.44 (m, 1H), 1.36 (s, 3H), 1.21 (d, J=8.0 Hz, 3H), 1.70 (d, J=6.0 Hz, 3H), 1.15-1.11 (m, 18H), 1.03 (d, J=7.2 Hz, 3H), 0.85 (d, J=7.2 Hz, 3H), 0.84 (t, J=7.2 Hz, 3H), 0.70 (d, J=7.6 Hz, 3H), 0.18 (d, J=6.8 Hz, 3H).

EXAMPLE 21

3-(Azithromycin-4''-ylcarbamylethylamino)-rifamycin S

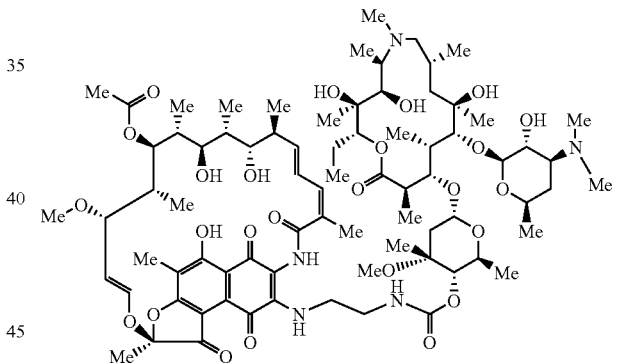

The title compound was prepared by following the same procedure as described for the preparation of Example 17 except azithromycin was used in place of clarithromycin. The title product was obtained as a dark purple solid in 15% yield. ESI MS m/z 1528.7 (M+H⁺); $^1$H NMR (400 MHz, CDCl$_3$) δ (ppm) 13.62 (br s, 1H), 7.64 (s, 1H), 6.89-6.83 (m, 1H), 6.51 (s, 1H), 6.31 (d, J=10.8 Hz, 1H), 6.12 (dd, J=6.0, 12.0 Hz, 1H), 6.06 (dd, J=0.8, 12.4 Hz, 1H), 5.29 (br s, 1H), 5.13-5.09 (m, 2H), 5.02 (d, J=10.0 Hz, 1H), 4.82 (br s, 1H), 4.69 (d, J=9.2 Hz, 1H), 4.53 (d, J=6.8 Hz, 2H), 4.49 (d, J=9.6 Hz, 1H), 4.34-4.28 (m, 1H), 4.23-4.21 (m, 1H), 3.92 (d, J=4.8 Hz, 1H), 3.86 (d, J=9.6 Hz, 1H), 3.76-3.72 (m, 1H), 3.66 (s, 1H), 3.61-3.56 (m, 4H), 3.47 (s, 3H), 3.46-3.31 (m, 4H), 3.28 (s, 3H), 3.18 (s, 3H), 3.08 (s, 3H), 3.05-3.01 (m, 1H), 2.94 (br s, 1H), 2.77-2.68 (m, 3H), 2.53 (d, J=10.0 Hz, 1H), 2.45-2.31 (m, 7H), 2.31 (s, 3H), 2.28 (s, 3H), 2.07 (s, 3H), 2.05 (s, 3H), 2.04-1.96 (m, 2H), 1.92-1.86 (m, 1H), 1.80-1.57 (m, 6H), 1.73 (s, 3H), 1.47-1.43 (m, 1H), 1.50-1.44 (m, 1H), 1.28 (s, 3H), 1.19-1.01 (m, 24H), 0.91-0.86 (m, 9H), 0.67 (d, J=6.8 Hz, 3H), 0.07 (d, J=7.2 Hz, 3H).

EXAMPLE 22

3-(Clarithromycin-4"-ylcarbamylethylaminomethyl) rifamycin S V

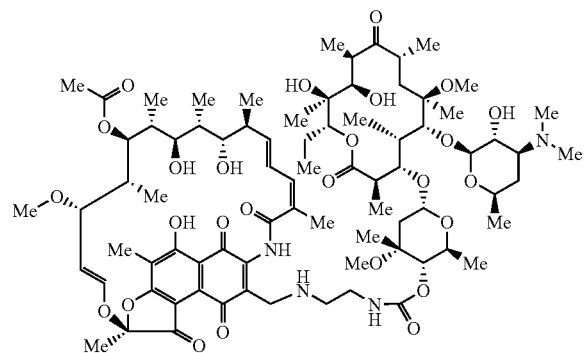

To a stirred solution of 2'-acetoxy-4"-aminoethylaminocarbonylclarithromycin prepared as described in Example 17 (14.6 mg, 0.017 mmol) and 3-formylrifamycin (17.8 mg, 0.024 mmol) in MeOH (0.5 mL) was added acetic acid (1 µL, 0.017 mmol). The resultant mixture was allowed to stir at room temperature for 1 hour, NaCNBH$_3$ (4.5 mg, 0.072 mmol) was added and the stirring was maintained for 40 min. The reaction mixture was partitioned between ethyl acetate and water. The organic layer was washed with brine, dried over Na$_2$SO$_4$ and concentrated in vacuo. The residue was purified by PTLC (10% MeOH/CH$_2$Cl$_2$) to afford a dark purple solid, which was dissolved in MeOH and heated at 48° C. overnight. Evaporation of the solvent in vacuo gave product as a dark purple solid (220 mg, 57%). ESI MS m/z 1543.7 (M+H$^+$); $^1$H NMR (400 MHz, CDCl$_3$) δ (ppm) 12.46 (br s, 1H), 8.33 (s, 1H), 6.62 (s, 1H), 6.60-6.48 (m, 1H), 6.33 (d, J=10.8 Hz, 1H), 6.16-6.12 (m, 2H), 6.06 (dd, J=1.2, 12.4 Hz, 1H), 5.08 (d, J=9.6 Hz, 1H), 4.97 (br s, 1H), 4.93-4.85 (m, 1H), 4.48 (br s, 1H), 4.24-4.13 (m, 2H), 3.99-3.82 (m, 2H), 3.97 (s, 1H), 3.74 (s, 3H), 3.74-3.62 (m, 5H), 3.46 (s, 3H), 3.41 (d, J=5.2 Hz, 1H), 3.33-3.15 (m, 2H), 3.29 (s, 3H), 3.19 (s, 3H), 3.02 (s, 6H), 3.02-2.94 (m, 3H), 2.88 (t, J=7.2 Hz, 1H), 2.56 (app s, 4H), 2.35-2.20 (m, 4H), 2.07 (s, 3H), 2.04 (s, 3H), 2.00-1.90 (m, 3H), 1.76 (m, 3H), 1.68-1.58 (m, 2H), 1.49-1.30 (m, 5H), 1.35 (s, 3H), 1.28-1.12 (m, 21H), 1.05 (d, J=7.2 Hz, 3H), 1.02 (d, J=6.8 Hz, 3H), 0.87 (t, J=9.2 Hz, 3H), 0.84 (t, J=7.6 Hz, 3H), 0.60 (d, J=6.0 Hz, 3H), −0.25 (app s, 3H).

EXAMPLE 23

(S)-3-[4-[4-(5-Acetylaminomethyl-2-oxo-oxazolidin-3-yl)-2-fluoro-phenyl]-piperazin-1-yl]rifamycin S

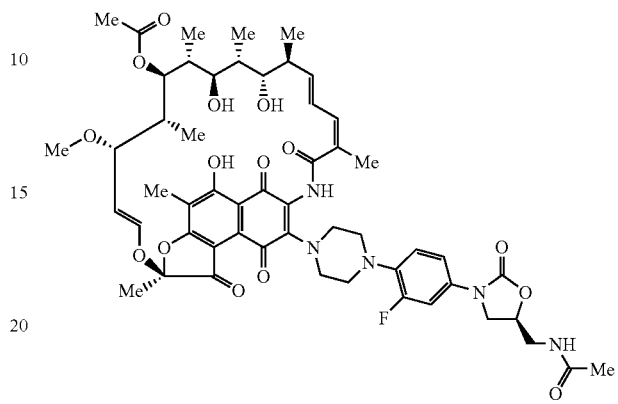

To a stirred solution of 3-(3-fluoro-4-piperazinyl-phenyl)-2-oxo-oxazolidin-5-ylmethyl-acetamide (5.0 mg, 0.015 mmol) in THF/EtOH (0.20 mL/0.60 mL) was added NaHCO$_3$ (1.8 mg, 0.021 mmol) and 3-bromorifamycin (12.0 mg, 0.015 mmol). The resultant solution was stirred at room temperature for 5.5 h and concentrated in vacuo to dryness. The crude product was purified by preparative thin layer chromatography (10% MeOH/CH$_2$Cl$_2$) to yield the title product as a purple-black solid (9.0 mg, 59%). ESI MS m/z 1030.3 (M+H$^+$); $^1$H NMR (400 MHz, CDCl$_3$) δ 13.27 (s, 1H), 7.54 (s, 1H), 7.45 (dd, J=2.4, 14.0 Hz, 1H), 7.18 (app t, J=12.8 Hz, 1H), 7.06 (dd, J=2.0, 8.8 Hz, 1H), 6.93 (t, J=8.8 Hz, 1H), 6.38 (d, J=10.8 Hz, 1H), 6.19-6.09 (m, 2H), 6.07 (dd, J=1.6, 10.8 Hz, 1H), 5.13 (d, J=9.2 Hz, 1H), 5.11 (dd, J=4.8, 12.4 Hz, 1H), 4.79-4.76 (m, 1H), 4.02 (t, J=9.2 Hz, 1H), 4.00-3.94 (m, 2H), 3.76-3.67 (m, 5H), 3.64-3.56 (m, 2H), 3.52-3.48 (m, 4H), 3.34-3.31 (m, 2H), 3.11 (s, 3H), 3.09-3.05 (m, 2H), 2.38-2.32 (m, 1H), 2.27 (s, 3H), 2.14 (s, 3H), 2.09 (s, 3H), 2.03 (s, 3H), 1.88-1.80 (m, 2H), 1.75 (s, 3H), 1.04 (d, J=6.8 Hz, 3H), 0.89 (d, J=7.2 HZ, 3H), 0.73 (d, J=6.4 Hz, 3H), 0.21 (d, J=6.8 Hz, 3H).

EXAMPLE 24

(S)-3-[4-[4-(5-Acetylaminomethyl-2-oxo-oxazolidin-3-yl)-2-fluoro-phenyl]-piperazin-1-ylethylamino]-rifamycin S

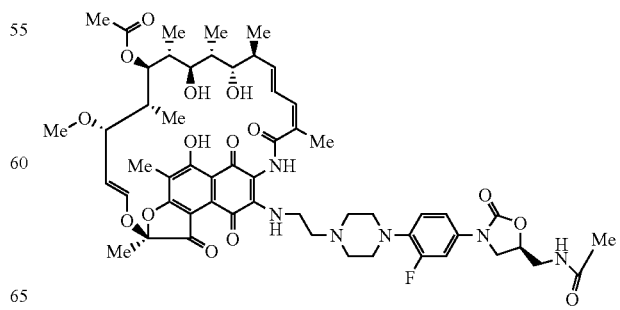

Step 1. N-[3-(4-{4-[2-(1,3-Dioxo-1,3-dihydro-isoindol-2-yl)-ethyl]-piperazin-1-yl}-3-fluoro-phenyl)-2-oxo-oxazolidin-5S-ylmethyl]-acetamide: To a stirred solution of 3-(3-fluoro-4-piperazinyl-phenyl)-2-oxo-oxazolidin-5S-ylmethyl-acetamide (17 mg, 0.05 mmol) in DMSO (0.5 mL) was added $K_2CO_3$ (10.0 mg, 0.07 mmol) and N-(2-bromo-ethyl) phthalimide (18.6 mg, 0.07 mmol). The resultant mixture was allowed to stir overnight at room temperature and partitioned between ethyl acetate and DI water. The separated organic layer was washed with brine, dried over $Na_2SO_4$ and concentrated in vacuo to dryness. The crude product was purified by preparative thin layer chromatography (10% MeOH/$CH_2Cl_2$) to give the title compound as a white solid (5.0 mg, 20%). ESI MS m/z 510.3 (M+H)$^+$; $^1$H NMR (400 MHz, CDCl$_3$) δ 7.88-7.85 (m, 2H), 7.75-7.72 (m, 2H), 7.43 (td, J=2.4, 13.2 Hz, 1H), 7.06 (m, 1H), 6.90 (td, J=2.4, 9.6 Hz, 1H), 6.04 (t, J=6.0 Hz, 1H), 4.78-4.75 (m, 1H), 4.35 (t, J=4.8 Hz, 1H), 4.05-3.99 (m, 2H), 3.87 (t, J=6.4 HZ, 1H), 3.77-3.68 (m, 2H), 3.64-3.55 (m, 2H), 3.02-2.97 (m, 4H), 2.72 (m, 4H), 2.02 (s, 3H).

Step 2. N-(3-{4-[4-(2-Amino-ethyl)-piperazin-1-yl]-3-fluoro-phenyl}-2-oxo-oxazolidin-5S-ylmethyl)-acetamide: To a stirred solution of the product from step 1 (5.0 mg, 0.01 mmol) in methanol (0.3 mL) was added hydrazine (1 μL, 0.03 mmol). The resultant solution was allowed to stir for 40 min at 65° C. and concentrated in vacuo to dryness. The crude product was purified by preparative thin layer chromatography (10% MeOH/$CH_2Cl_2$) to give product as a white solid (1.2 mg, 35%): $^1$H NMR (400 MHz, CD$_3$OD) δ 7.49 (dd, J=2.4, 14.8 Hz, 1H), 7.11-7.08 (m, 1H), 7.06 (t, J=9.2 Hz, 1H), 4.79-4.76 (m, 1H), 4.12 (t, J=9.2 Hz, 1H), 3.79 (dd, J=6.4, 9.2 Hz, 1H), 3.55 (d, J=4.8 Hz, 2H), 3.12-3.08 (app s, 4H), 2.83 (t, J=6.4 Hz, 2H), 2.67 (app s, 4H), 2.54 (t, J=6.4 Hz, 2H), 1.96 (s, 3H).

Step 3. (S)-3-[4-[4-(5-Acetylaminomethyl-2-oxo-oxazolidin-3-yl)-2-fluoro-phenyl]-piperazin-1-ylethylamino]rifamycin S: To a stirred solution of the product from step 2 (1.0 mg, 0.0026 mmol) in EtOH (0.25 mL) was added NaHCO$_3$ (2.4 mg, 0.028 mmol) and 3-bromorifamycin (3.0 mg, 0.0038 mmol). The reaction mixture was allowed to stir overnight at room temperature, concentrated in vacuo, and the crude product was purified by PTLC (10% MeOH/CH$_2$Cl$_2$) to afford product as a purple solid (0.3 mg, 10%). ESI MS m/z 1073.5 (M+H)$^+$; $^1$H NMR (400 MHz, CDCl$_3$) δ 13.94 (br s, 1H), 7.53 (s, 1H), 7.46 (d, J=12.0 Hz, 1H), 7.10-7.07 (m, 1H), 7.01 (s, 1H), 6.94 (t, J=9.2 Hz, 1H), 6.35-6.31 (m, 1H), 6.18-6.12 (m, 1H), 6.07 (d, J=12.4 Hz, 1H), 5.98-5.94 (m, 1H), 5.15-5.10 (m, 1H), 5.07 (d, J=11.6 Hz, 1H), 4.72-4.65 (m, 1H), 4.04 (t, J=8.8 Hz, 1H), 3.98-3.94 (m, 1H), 3.91-3.86 (m, 1H), 3.77-3.48 (m, 12H), 3.10 (s, 3H), 3.10-3.04 (m, 4H), 2.69-2.58 (m, 4H), 2.40-2.33 (m, 1H), 2.29 (s, 3H), 2.27-2.21 (m, 1H), 2.18 (s, 3H), 2.08 (s, 3H), 2.04 (s, 3H), 1.82-1.76 (m, 1H), 1.75 (s, 3H), 1.05 (d, J=7.2 Hz, 3H), 0.86 (d, J=7.2 HZ, 3H), 0.69 (d, J=6.4 Hz, 3H), 0.10 (d, J=7.2 Hz, 3H).

EXAMPLE 25

3-[1-(3-Carboxy-1-cyclopropyl-6-fluoro-4-oxo-1,4-dihydroquinolin-7-yl)azetidin-3-methylamino)rifamycin S

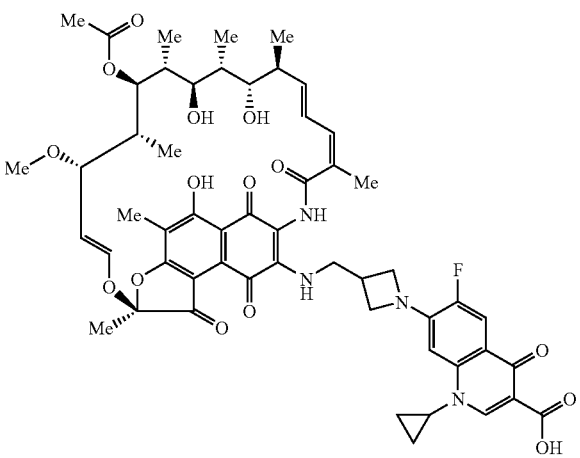

Step 1. 7-(3-aminomethyl-azetidin-1-yl)-1-cyclopropyl-6-fluoro-4-oxo-1,4-dihydro-quinoline-3-carboxylic acid: The title compound was prepared by using the same procedure as described for the preparation of Example 8 step 1 except azetidin-3-ylmethyl-carbamic acid tert-butyl ester was used in place of (R)-pyrrolidin-3-yl-carbamic acid tert-butyl ester. ESI MS m/z 332 (M+H)$^+$; $^1$H NMR (400 MHz, DMSO-d$_6$) δ 8.56 (s, 1H), 8.02 (br s, 2H) 7.79 (d, J=12.52 Hz, 1H), 6.84 (d, J=7.04 Hz, 1H), 4.30 (m, 2H), 4.03 (m, 2H), 3.71 (m, 1H), 3.17 (d, J=7.82 Hz, 2H) 3.04 (m, 1H), 1.24 (m, 2H), 1.13 (m, 2H).

Step 2. 3-[1-(3-Carboxy-1-cyclopropyl-6-fluoro-4-oxo-1,4-dihydroquinolin-7-yl)azetidin-3-methylamino)rifamycin S: The title compound was prepared by using similar procedure as described for the preparation of Example 10 except 7-(3-aminomethyl-azetidin-1-yl)-1-cyclopropyl-6-fluoro-4-oxo-1,4-dihydro-quinoline-3-carboxylic acid was used in place of (R/S)-1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated a purple black solid in 61% yield. ESI MS m/z 1025 (M+H)$^+$; $^1$H NMR (400 MHz, CDCl$_3$): δ 13.81 (s, 1H), 8.97 (s, 1H), 8.19 (d, J=12.50 Hz, 1H), 6.95 (d, J=7.04 Hz, 1H), 6.65 (m, 1H), 6.44 (m, 1H), 6.34 (m, 1H), 5.38 (dd, J=5.47, 11.73 Hz, 1H), 5.27 (d, J=10.95 Hz, 1H), 4.60 (m, 1H), 4.24 (m, 2H), 4.13 (m, 1H), 3.73 (m, 2H), 3.36 (s, 3H), 3.33 (m, 1H), 2.63 (m, 1H), 2.56 (s, 3H), 2.51 (m, 1H), 2.33 (m, 1H), 2.36 (s, 3H), 2.33 (s, 3H), 2.01 (s, 3H), 2.08-1.74 (m, 5H), 1.62 (m, 2H), 1.43 (m, 2H), 1.31 (d, J=7.04 Hz, 3H), 1.12 (d, J=7.04 Hz, 3H), 0.95 (d, J=6.20 Hz, 3H), 0.36 (d, J=7.04 Hz, 3H).

EXAMPLE 26

3-[4-(3-Carboxy-1-cyclopropyl-6-fluoro-8-methoxy-4-oxo-1,4-dihydroquinolin-7-yl)-piperazin-1-yl]rifamycin S

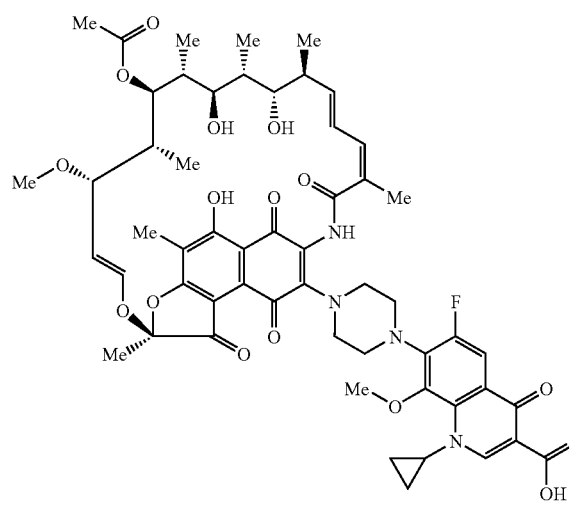

The title compound was prepared by using the same procedure as described for the preparation of Example 10 except 1-cyclopropyl-6-fluoro-8-methoxy-4-oxo-7-piperazin-1-yl-1,4-dihydro-quinoline-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a black solid (48% yield). MS: (M+H$^+$) 1055.

EXAMPLE 27

(R/S)-3-[4-(3-Carboxy-1-cyclopropyl-6-fluoro-8-methoxy-4-oxo-1,4-dihydroquinolin-7-yl)-piperazin-1-yl]rifamycin S

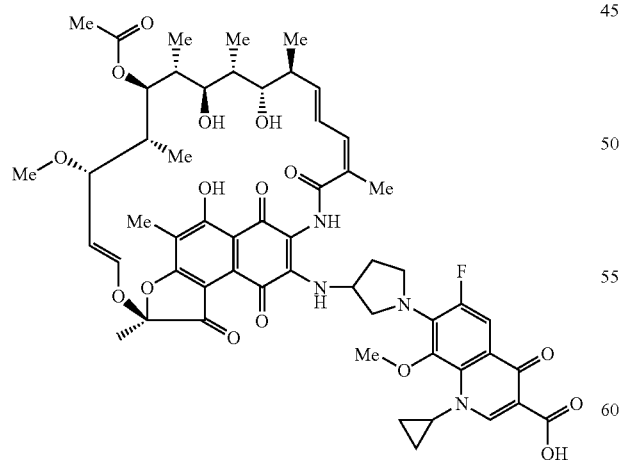

The title compound was prepared by using the same procedure as described for the preparation of Example 10 except 7-(3-amino-pyrrolidin-1-yl)-1-cyclopropyl-6-fluoro-8-methoxy-4-oxo-1,4-dihydro-quinoline-3-carboxylic acid (prepared similarly by using the procedure as described for the preparation of (R)-7-(3-tert-Butoxycarbonylamino-pyrrolidin-1-yl)-1-cyclopropyl-6-fluoro-4-oxo-1,4-dihydroquinoline-3-carboxylic acid) was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a mixture of diastereomers as a black solid (40% yield). MS: (M+H$^+$) 1055.

EXAMPLE 28

(R/S)-3-[1-(3-Carboxy-1-cyclopropyl-6-fluoro-8-methoxy-4-oxo-1,4-dihydroquinolin-7-yl)-pyrrolidin-3-ylamino-methyl]rifamycin S

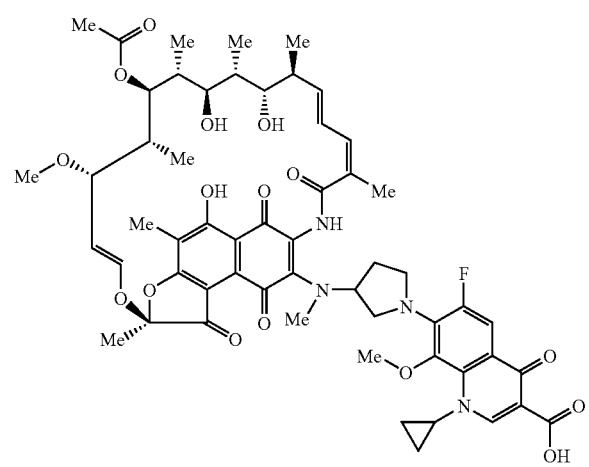

The title compound was prepared by using the same procedure as described for the preparation of Example 10 except 1-cyclopropyl-6-fluoro-8-methoxy-7-(3-methylamino-pyrrolidin-1-yl)-4-oxo-1,4-dihydro-quinoline-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a mixture of diastereomers as a black solid (5% yield). MS: (M+H$^+$) 1069.

EXAMPLE 29

(R/S)-3-{4-[1-(3-Carboxy-8-chloro-1-cyclopropyl-6-fluoro-4-oxo-1,4-dihydroquinolin-7-yl)-pyrrolidin-3-ylamino]-piperidin-1-yl}rifamycin S

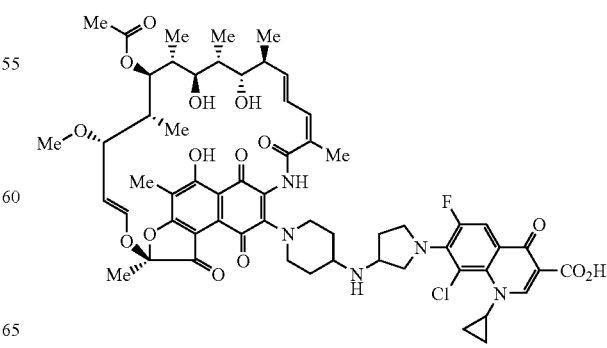

Step 1. 3-(4-Piperidone)-rifamycin S: 4-Piperidone HCl (700 mg) was dissolved in THF/water (2:1, 5 mL) at room temperature, to this was added 3-bromorifamycin S, followed by sodium bicarbonate (1 g). The solution was allowed to stir at room temperature for 18 h, and partitioned between 5% citric acid and dichloromethane. The organic layer was separated, dried, concentrated in vacuo, and the residue was purified by preparative TLC to give the title product (500 mg) as a gray solid.

Step 2. (R/S)-7-[3-Aminopyrrolidin-1-yl]-8-chloro-1-cyclopropyl-6-fluoro-4-oxo-1,4-dihydro-quinoline-3-carboxylic acid hydrochloride (clinafloxacin hydrochloride) (90 mg, 0.23 mmol) was dissolved in warm DMSO (2 mL), this was diluted in dichloromethane (4 mL). To this clear yellow solution was added, sodium acetate and cooled to room temperature. To this was added, 3-piperidone-rifamycin S (160 mg, 0.2 mmol), followed by acetic acid (60 uL). This was allowed to stir at room temperature for 2 h, sodium triacetoxyborohydride (110 mg, 0.44 mmol) was added, and stirring was kept for 18 h under nitrogen. The reaction mixture was partitioned between ethyl acetate (50 mL) and PBS buffer (pH 7.4, 20 mL). To the resulting suspension was added K3Fe(CN)6 (250 mg), and stirred for 4 h. The organic phase was separated, the clear aqueous phase was extracted with ethyl acetate. The combined organics were washed with 5% citric acid (2×), and dried over sodium sulfate and concentrated in vacuo. The residue was purified by preparative TLC, eluated twice with 10% MeOH/DCM/1% HOAc, followed by 1% HOAc/ethyl acetate. The desired band was collected, and extracted with 10% MeOH in dichloromethane. The organic extract was filtered, and washed with 5% citric acid solution, dried over sodium sulfate and concentrated in vacuo to give a black solid (40 mg), LCMS: 1142 (M+H).

EXAMPLE 30

(R/S)-3-{4-[1-(3-Carboxy-1-cyclopropyl-6-fluoro-8-methoxy-4-oxo-1,4-dihydroquinolin-7-yl)-pyrrolidin-3-ylamino]-piperidin-1-yl}rifamycin S

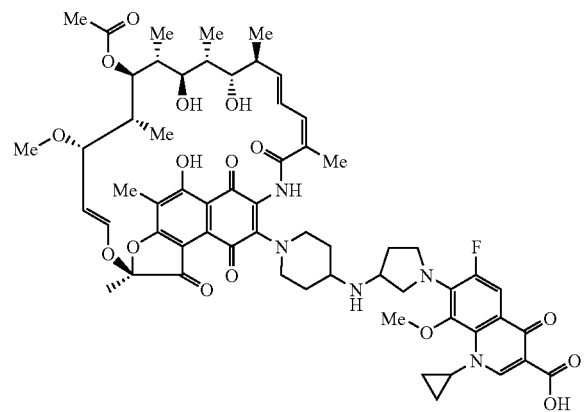

The title compound was prepared by using the same procedure as described for the preparation of Example 29 except (R/S)-1-cyclopropyl-6-fluoro-8-methoxy-4-oxo-7-[3-(piperidin-4-ylamino)-pyrrolidin-1-yl]-1,4-dihydro-quinoline-3-carboxylic acid was used instead of (R/S)-7-[3-Aminopyrrolidin-1-yl]-8-chloro-1-cyclopropyl-6-fluoro-4-oxo-1,4-dihydro-quinoline-3-carboxylic acid. The title compound was isolated as a mixture of diastereomers as a black solid (27% yield). MS: (M+H$^+$) 1138.

EXAMPLE 31

3-{4-[1-(3-Carboxy-1-cyclopropyl-6-fluoro-8-methoxy-4-oxo-1,4-dihydroquinolin-7-yl)-piperazin-4-yl]-piperidin-1-yl}rifamycin S

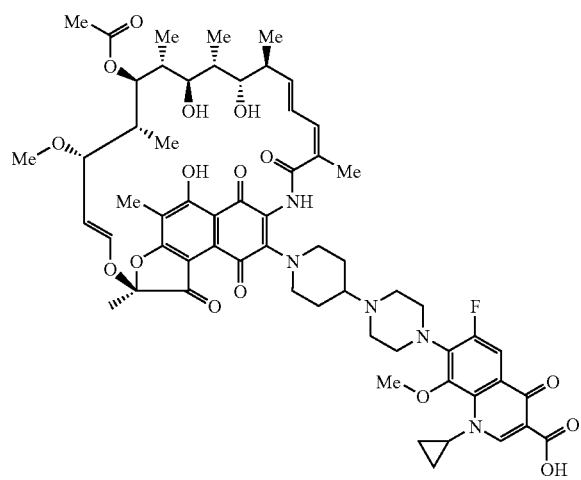

The title compound was prepared by using the same procedure as described for the preparation of Example 29 except 1-cyclopropyl-6-fluoro-8-methoxy-4-oxo-7-piperazin-1-yl-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (52% yield). MS: (M+H$^+$) 1138.

EXAMPLE 32

(R/S)-3-{4-[1-(3-Carboxy-1-cyclopropyl-6-fluoro-8-methoxy-4-oxo-1,4-dihydroquinolin-7-yl)-piperidin-3-ylamino]-piperidin-1-yl}rifamycin S

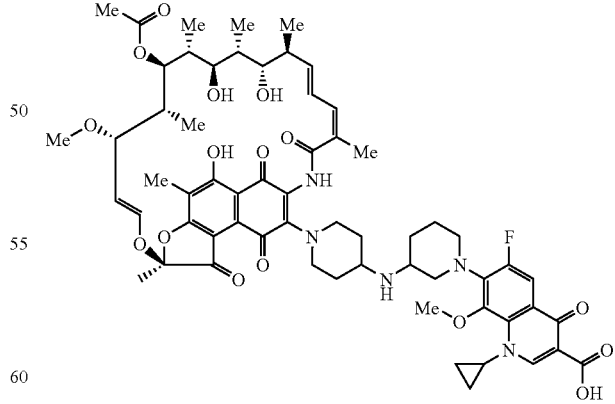

The title compound was prepared by using the same procedure as described for the preparation of Example 29 except 7-(3-amino-piperidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1- cyclopropyl-6-fluoro-4-oxo-1,4-dihydro-quinoline-3-carboxylic acid hydrochloride (clinafloxacin HCl). The title compound was isolated as a mixture of diastereomers as a black solid (44% yield). MS: (M+H$^+$) 1152.

EXAMPLE 33

3-{4-[1-(3-Carboxy-1-cyclopropyl-6-fluoro-8-methoxy-4-oxo-1,4-dihydroquinolin-7-yl)-azetidin-3-ylamino]-piperidin-1-yl}rifamycin S

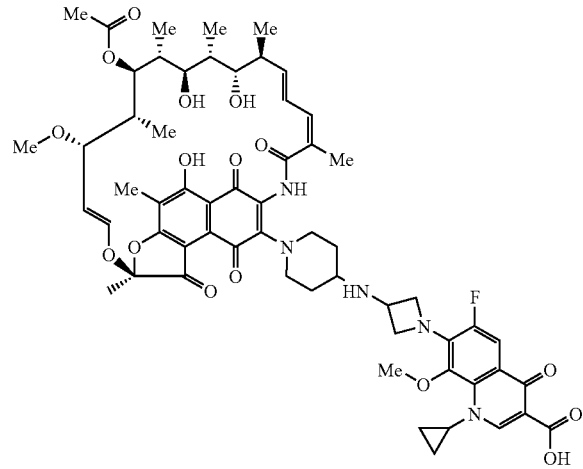

The title compound was prepared by using the same procedure as described for the preparation of Example 29 except 7-(3-amino-azetidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxain HCl). The title compound was isolated as a black solid (38% yield). MS: (M+H$^+$) 1124.

EXAMPLE 34

(R/S)-3-{4-[1-(3-Carboxy-1-cyclopropyl-6-fluoro-8 methoxy-4-oxo-1,4-dihydroquinolin-7-yl)-pyrrolidin-3-ylamino-methyl]-piperidin-1-yl}rifamycin S

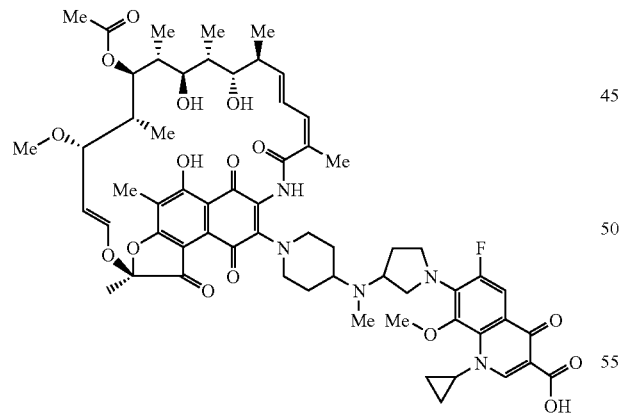

The title compound was prepared by using the same procedure as described for the preparation of Example 29 except 1-cyclopropyl-6-fluoro-8-methoxy-7-(3-methylamino-pyrrolidin-1-yl)-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (17% yield). MS: (M+H$^+$) 1152.

EXAMPLE 35

3-{4-[6-(3-Carboxy-1-cyclopropyl-6-fluoro-8-methoxy-4-oxo-1,4-dihydroquinolin-7-yl)-octahydropyrrolo[3,4-b]-pyrridin-1-yl]-piperidin-1-yl}rifamycin S

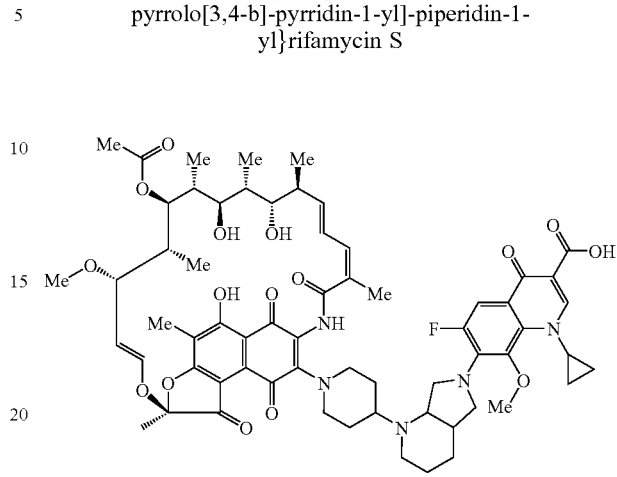

The title compound was prepared by using the same procedure as described for the preparation of Example 29 except 1-cyclopropyl-6-fluoro-8-methoxy-7-(octahydropyrrolo[3,4-b]pyridin-6-yl)-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (6% yield). MS: (M+H$^+$) 1178.

EXAMPLE 36

(R/S)-3-{4-[1-(3-Carboxy-8-chloro-1-cyclopropyl-6-fluoro-4-oxo-1,4-dihydroquinolin-7-yl)-(pyrrolidin-3-ylmethyl)-amino]-piperidin-1-yl}rifamycin S

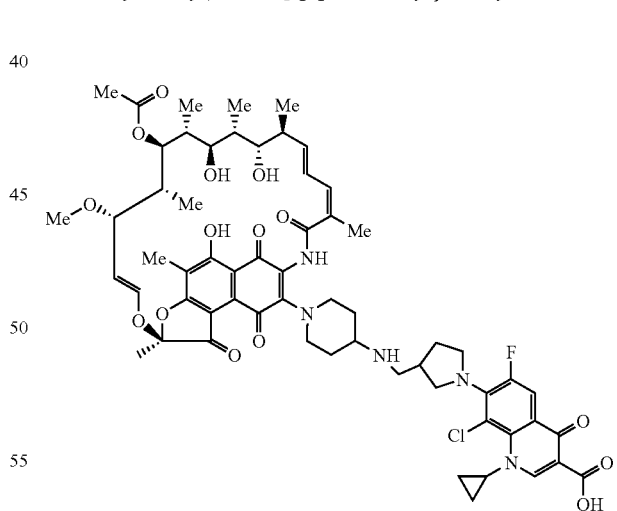

The title compound was prepared by using the same procedure as described for the preparation of Example 29 except 7-(3-aminomethyl-pyrrolidin-1-yl)-8-chloro-1-cyclopropyl-6-fluoro-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (13% yield). MS: (M+H$^+$) 1156.

EXAMPLE 37

(R/S)-3-{4-[1-(3-Carboxy-1-(2,3-difluoro-phenyl)-6-fluoro-4-oxo-1,4-dihydro[1,8]naphthyridine-7-yl)-(pyrrolidin-3-ylmethyl)-amino]-piperidin-1-yl}rifamycin S

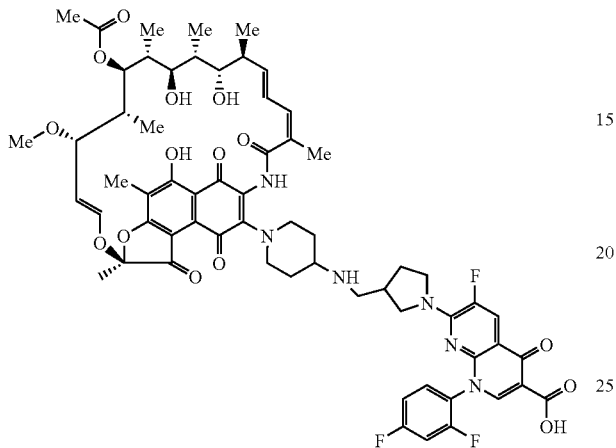

The title compound was prepared by using the same procedure as described for the preparation of Example 29 except 7-(3-aminomethyl-pyrrolidin-1-yl)-1-(2,4-difluoro-phenyl)-6-fluoro-4-oxo-1,4-dihydro-[1,8]naphthyridine-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (10% yield). MS: (M+H$^+$) 1195.

EXAMPLE 38

3-{4-[1-(3-Carboxy-8-chloro-1-cyclopropyl-6-fluoro-4-oxo-1,4-dihydroquinolin-7-yl)-piperazin-4-yl]-piperidin-1-yl}rifamycin S

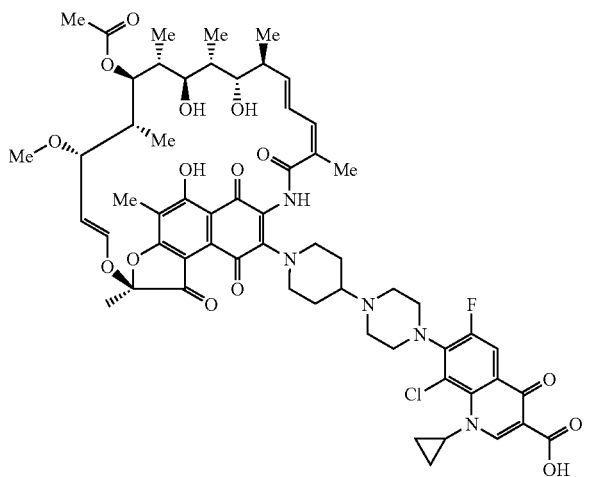

The title compound was prepared by using the same procedure as described for the preparation of Example 29 except 8-chloro-1-cyclopropyl-6-fluoro-4-oxo-7-piperazin-1-yl-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (10% yield). MS: (M+H$^+$) 1142.

EXAMPLE 39

3-{4-[1-(3-Carboxy-1-cyclopropyl-6-fluoro-8-methoxy-4-oxo-1,4-dihydroquinolin-7-yl)-pyrrolidin-3-ylethylamino]-piperidin-1-yl}rifamycin S

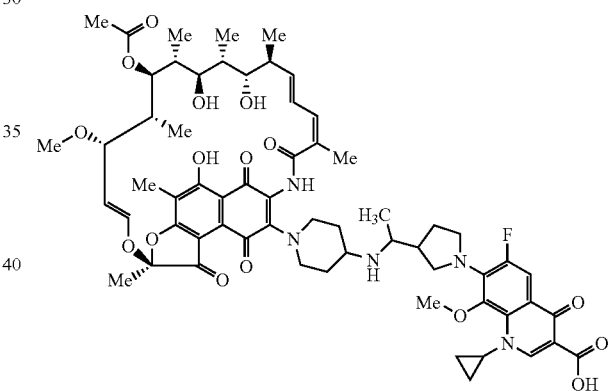

The title compound was prepared by using the same procedure as described for the preparation of Example 29 except 1-cyclopropyl-6-fluoro-8-methoxy-4-oxo-7-{3-[1-(piperidin-4-ylamino)-ethyl]-pyrrolidin-1-yl}-1,4-dihydro-quinoline-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a black solid (35% yield). MS: (M+H$^+$) 1166; $^1$H NMR (400 MHz, CDCl$_3$) δ 8.74 (s, 1 H), 7.79 (d, J=8.8 Hz, 1 H), 7.54 (s, 1 H), 7.07 (m, 1 H), 6.33 (d, J=11.2 Hz, 1 H), 6.20 (m, 1 H), 6.05 (d, J=11.6 Hz, 1 H), 5.06 (m, 2 H), 4.12-3.19 (complex pattern), 3.07 (s, 3 H), 3.04 (d, J=11.5 Hz, 1 H), 2.82 (br s, 2 H), 2.34 (m, 1 H), 2.24 (s, 3 H), 2.15 (m, 2 H), 2.05 (s, 3 H), 1.79 (m, 3 H), 1.72 (s, 3 H), 1.66 (m, 4 H), 1.22 (m, 1 H), 1.10 (m, 2 H), 1.02 (d, J=7.2 Hz, 3 H), 0.86 (d, J=7.1 Hz, 3 H), 0.69 (d, J=7.3 Hz, 3 H), 0.16 (d, J=6.1 Hz, 3 H).

EXAMPLE 40

(R/S)-3-{4-(1-[1-(3-Carboxy-1-(2,3-difluoro-phenyl)-6-fluoro-4-oxo-1,4-dihydro-[1,8]naphthyridine-7-yl)-pyrrolidin-3-yl]-piperazin-1-yl)-piperidin-1-yl}-rifamycin S

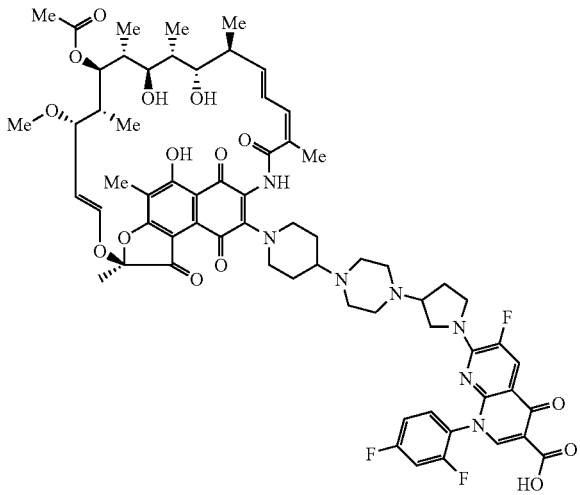

The title compound was prepared by using the same procedure as described for the preparation of Example 29 except 1-(2,4-difluoro-phenyl)-6-fluoro-4-oxo-7-(3-piperazin-1-yl-pyrrolidin-1-yl)-1,4-dihydro-[1,8]naphthyridine-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (29% yield). MS: (M+H$^+$) 1250; $^1$H NMR (400 MHz, CDCl$_3$) δ 13.26 (s, 1 H), 8.61 (s, 1 H), 7.99 (s, 1 H), 7.52 (s, 1 H), 7.35 (m, 1 H), 7.05 (m, 3 H), 6.34 (d, J=11.0 Hz, 1 H), 6.16 (dd, J=16.4 and 6.2 Hz, 1 H), 6.05 (d, J=12.3 Hz, 1 H), 5.06 (m, 2 H), 3.95 (m, 2 H), 3.44 (m, 2 H), 3.29 (m, 1 H), 3.07 (s, 1 H), 3.04 (m, 1 H), 2.93 (s, 23 H), 2.85 (s, 3 H), 2.60 (br s, 4 H), 2.33 (m, 1 H), 2.24 (s, 1H), 2.05 (s, 3 H), 1.79 (m, 3 H), 1.71 (s, 3 H), 1.01 (d, J=6.4 Hz, 3 H), 0.86 (d, J=7.0 Hz, 3 H), 0.68 (d, J=6.3 Hz, 3 H), 0.15 (d, J=6.0 Hz, 3 H).

EXAMPLE 41

(R/S)-3-[4-{1-[1-(3-Carboxy-1-cyclopropyl-6-fluoro-8-methoxy-4-oxo-1,4-dihydro-quinoline-7-yl)-pyrrolidin-3-yl]-cyclopropylamino}-piperidin-1-yl]-rifamycin S

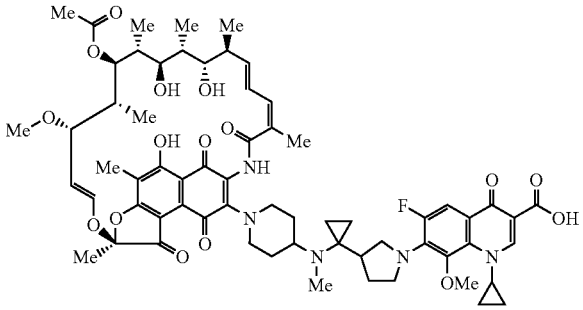

Step 1. 4-Methylamino-piperidine-1-carboxylic acid tert-butyl ester: To a solution of 4-oxo-piperidine-1-carboxylic acid tert-butyl ester (2.0 g, 10 mmol) and methyl amine (2.0 M in MeOH, 20 mL, 40 mmol) in methanol (7.0 mL) was added MgSO$_4$ (1.0 g) and stirred at room temperature for 2 h. NaBH$_3$CN (304 mg, 4.8 mmol) was added in two portions. The resulting solution was stirred at room temperature for 30 minutes and then partitioned between ethyl acetate and water. The separated organic layer was washed with brine, dried over sodium sulfate and concentrated in vacuo to give colorless oil (1.6 g).

Step 2. 4-(Acryloyl-ethyl-amino)-piperidine-1-carboxylic acid tert-butyl ester: To a solution of 4-methylamino-piperidine-1-carboxylic acid tert-butyl ester (1.6 g, 7.5 mmol) in dichloromethane (15 mL) was added NaHCO$_3$ (1.5 g, 17.9 mmol), followed by acryloyl chloride (0.66 mL, 8.1 mmol) at 0° C. After stirred at room temperature for 30 min, the solution was partitioned between ethyl acetate and water. The separated organic layer was washed with brine, dried over sodium sulfate and concentrated in vacuo to give colorless oil (2.0 g).

Step 3. 4-[(1-Benzyl-pyrrolidine-3-carbonyl)-methyl-amino]-piperidine-1-carboxylic acid tert-butyl ester: To a solution of 4-(acryloyl-ethyl-amino)-piperidine-1-carboxylic acid tert-butyl ester (2.0 g, 7.5 mmol) and N-(methoxymethyl)-N-(trimethylsilylmethyl)benzylamine (1.92 mL, 7.5 mmol) in dichloromethane (20 mL) was added trifluoroacetic acid (50 μL, 0.44 mmol) at room temperature. The resulting solution was stirred overnight and concentrated in vacuo to give colorless oil, which was purified by flash chromatography on silica gel with gradient eluation of 2-10% methanol in dichloromethane to give oil (2.0 g, 66%). ESI MS m/z 402.3 (M+H$^+$).

Step 4: 4-{[1-(1-Benzyl-pyrrolidin-3-yl)-cyclopropyl]-methyl-amino}-piperidine-1-carboxylic acid tert-butyl ester: The solution of ethylmagnesium bromide (3.0 M in ethyl ether, 2.1 mL, 6.3 mmol) in THF (17.0 mL) was cooled to −78° C. To this solution was added the solution of titanium (IV) isopropoxide (0.76 mL, 2.6 mmol) in THF (1.7 mL) dropwise with the temperature below −70° C. After stirred for three minutes, the solution of 4-[(1-benzyl-pyrrolidine-3-carbonyl)-methyl-amino]-piperidine-1-carboxylic acid tert-butyl ester (1.0 g, 2.5 mmol) in THF (1.7 mL) was added. The resulting solution was warmed to room temperature, heated at reflux for one hour and then cooled to 8° C. Ethylmagnesium bromide (3.0M in ethyl ether, 1.8 mL, 5.4 mmol) was added followed by the solution of titanium (IV) isopropoxide (0.66 mL, 2.2 mmol) in THF (1.0 mL) rapidly. The reaction mixture was stirred at room temperature for one hour and partitioned between ethyl acetate and water. The separated organic layer was washed with brine, dried over sodium sulfate and concentrated in vacuo. The residue was purified by preparative thin layer chromatography (60% ethyl acetate in hexane with 0.5% triethylamine) to give pale yellow oil (390 mg, 38%). ESI MS m/z 414.3 (M+H$^+$).

Step 5. 4-[Methyl-(1-pyrrolidin-3-yl-cyclopropyl)-amino]-piperidine-1-carboxylic acid tert-butyl ester: To a solution of 4-{[1-(1-benzyl-pyrrolidin-3-yl)-cyclopropyl]-methyl-amino}-piperidine-1-carboxylic acid tert-butyl ester (390 mg, 0.39 mmol) in acetic acid (12.0 mL) was added 30% Pd/C (150 mg). The resulting mixture was hydrogenated using a parr shaker under 50 Psi for 25 hours. The catalyst was filtered and solvent removed, residue was basified with 20% NaOH solution and extracted with ethyl acetate. The combined organic extracts were dried, concentrated in vacuo to a pale yellow oil (~300 mg) which could be used in next step directly. ESI MS m/z 324.3 (M+H$^+$).

Step 6: 7-(3-{1-[(1-tert-Butoxycarbonyl-piperidin-4-yl)-methyl-amino]-cyclopropyl}-pyrrolidin-1-yl)-1-cyclopropyl-6-fluoro-8-methoxy-4-oxo-1,4-dihydro-quinoline-3-carboxylic acid: A solution of 4-[methyl-(1-pyrrolidin-3-yl-cyclopropyl)-amino]-piperidine-1-carboxylic acid tert-butyl ester (100 mg, 0.31 mmol) in acetonitrile (30.0 mL) was added 7-fluoro-1-cyclopropyl-6-fluoro-8-methyl-4-oxo-1,4-dihydro-quinoline-3-carboxylic acid (98 mg, 0.33 mmol) and DBU (0.23 mL, 1.53 mmol). The suspension was heated to 75° C. overnight. The reaction mixture was partitioned between ethyl acetate and 5% citric acid. The separated organic layer was washed with brine, dried over sodium sulfate and concentrated in vacuo. The residue was purified by preparative thin layer chromatography (10% methanol in dichloromethane) to give the title compound as a yellow solid (102 mg, 62%). ESI MS m/z 599.3 (M+H$^+$).

Step 7: 1-Cyclopropyl-6-fluoro-8-methoxy-7-{3-[1-(methyl-piperidin-4-yl-amino)-cyclopropyl]-pyrrolidin-1-yl}-4-oxo-1,4-dihydro-quinoline-3-carboxylic acid: To a stirred solution of 7-(3-{1-[(1-tert-butoxycarbonyl-piperidin-4-yl)-methyl-amino]-cyclopropyl}-pyrrolidin-1-yl)-1-cyclopropyl-6-fluoro-8-methoxy-4-oxo-1,4-dihydro-quinoline-3-carboxylic acid in dichloroethane (2.0 mL) was added trifluoroacetic acid (1.0 mL, ~13 mmol) at 0° C. during a period of 5-6 minutes. The resulting solution was stirred at room temperature for one hour. The solvent was removed to yield yellow oil, which was partitioned between $CH_2Cl_2$ and sat. aq $NaHCO_3$. The separated aqueous phase was extracted with $CH_2Cl_2$. The combined organic layer was with brine, dried over sodium sulfate and concentrated in vacuo. Title compound was achieved as a yellow solid (85 mg, 100%). ESI MS m/z 499.4 (M+H$^+$).

Step 8: (R/S)-3-[4-{1-[1-(3-Carboxy-1-cyclopropyl-7-fluoro-9-methyl-4-oxo-4H-quinolizine-8-yl)-pyrrolidin-3-yl]-cyclopropylamino}-piperidin-1-yl]-rifamycin S: The title compound was prepared by following the same procedure described for the preparation of Example 10 except 1-cyclopropyl-6-fluoro-8-methoxy-7-{3-[1-(methyl-piperidin-4-yl-amino)-cyclopropyl]-pyrrolidin-1-yl}-4-oxo-1,4-dihydro-quinoline-3-carboxylic acid was used. ESI MS m/z 1160.6 (M–MeO)$^+$, 1192.3 (M+H)$^+$. $^1$H NMR (400 MHz, CDCl$_3$) δ (~1:1 two diastereomers) 13.22 (s, 1H), 8.74 (s 1H), 8.03 (br s, 1H), 7.76, 7.72 (two singlets, 1H), 7.55, 7.54 (two singlets, 1H), 7.00-6.95 (m, 1H), 6.32-6.29 (m, 1H), 5.13-6.09 (m, 1H), 6.01 (dd, J=2.4, 12.4 Hz, 1H), 5.07-5.00 (m, 2H), 4.02-3.79 (m, ~5H), 3.52 (s, 3H), 3.50-3.25 (m, ~6H), 3.05 (s, 3H), 3.02-2.88 (m, 2H), 2.68-2.64 (m, 1H), 2.50-2.49 (two singlets, 3H), 2.34-2.30 (m, 1H), 2.22 (s, 3H), 2.09-2.08 (two singlets, 3H), 2.04 (s, 3H), 2.02-1.89 (m, 2H), 1.80-1.70 (m, ~7H), 1.41-1.36 (m, 1H), 1.27-1.21 (m, 1H), 1.11-0.90 (m, 7H), 0.83-0.79 (m, 5H), 0.69-0.60 (m, 5H), 0.13-0.11 (m, 3H).

EXAMPLE 42

(R/S)-3-{4-({1-[1-(3-Carboxy-8-chloro-1-cyclopropyl-6-fluoro-4-oxo-1,4-dihydro-quinolin-7-yl)-pyrrolidin-3-yl]-cyclopropyl}-methyl-amino)-piperidin-1-yl]-rifamycin S

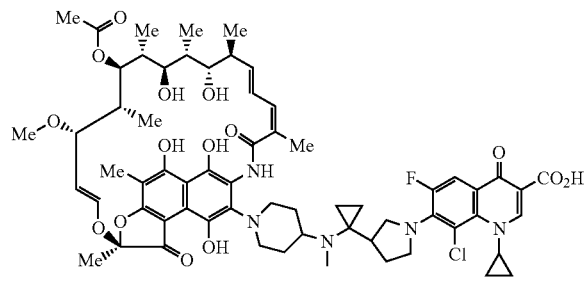

The title compound was prepared by using the same procedure as described for the preparation of Example 41 except 8-chloro-1-cyclopropyl-6-fluoro-7-{3-[1-(methyl-piperidin-4-yl-amino)-cyclopropyl]-pyrrolidin-1-yl}-4-oxo-1,4-dihydro-quinoline-3-carboxylic acid, which was prepared similarly as its 8-methoxy analog, was used in place of 1-cyclopropyl-6-fluoro-8-methoxy-7-{3-[1-(methyl-piperidin-4-yl-amino)-cyclopropyl]-pyrrolidin-1-yl}-4-oxo-1,4-dihydro-quinoline-3-carboxylic acid. The product was isolated as an orange solid in 17% yield. ESI MS m/z 1164 (M–CH$_3$O$^+$); $^1$H NMR (400 MHz, CDCl$_3$) δ 14.71 (s, 1H), 13.34 (s, 1H), 8.87 (s, 1H), 7.92 (d, J=13.2 Hz, 1H), 7.54 (s, 1H), 7.07 (m, 1H), 6.35 (d, J=10.4 Hz, 1H), 5.12-5.07 (m, 2H), 4.29 (m, 1 h), 3.99 (m, 4H), 3.61-3.33 (m, 8H), 3.10 (s, 3H), 3.10-2.66 (m, 2H), 2.80 (m, 1H), 2.66 (m, 1H), 2.37-1.20 (m, 14H), 2.37 (s, 3H), 2.26 (s, 3H), 2.12 (s, 3H), 2.10 (s, 3H), 2.08 (s, 3H), 1.74 (s, 3H), 1.04 (d, J=7.2 Hz, 3H), 0.87 (d, J=6.8 Hz, 3H), 0.71 (d, J=6.8 Hz, 3H), 0.17 (m, 3H).

EXAMPLE 43

(R/S)-3-{3-[1-(3-Carboxy-8-chloro-1-cyclopropyl-6-fluoro-4-oxo-1,4-dihydroquinolin-7-yl)-pyrrolidin-3-ylcarbamoyl]-azetidin-1-yl}rifamycin S

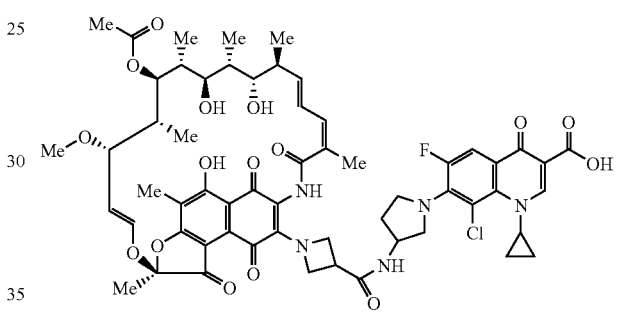

Step 1. 3-[(3-Carboxy)-azetidine-1-yl]-rifamycin S: The title compound was prepared by using the same procedure as described for the preparation of Example 10 except 3-azetidine carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The product was isolated as black solid (92% yield). MS: (M+H$^+$) 795.

Step 2. 3-[(3-Carboxy-2,5-dioxo-pyrrolidin-1-yl-ester)-azetidine-1-yl]-rifamycin S: To a solution of 3-[(3-carboxy)-azetidine-1-yl]-rifamycin S (318 mg, 0.4 mmol) in THF was added EDC (192 mg, 1.0 mmol), N-hydroxy succinimide (162 mg, 1.4 mmol) and DMAP (8 mg, 0.08 mmol). The resulting mixture was heated in a 35° C. oil bath for 18 hours before adding large amount of ethyl acetate and water. The separated organic phase was further washed with water (2×), brine (1×), dried over Na$_2$SO$_4$, concentrated in vacuo to give a black solid. It was used in next step without further purification. MS: (M+H$^+$) 892.

Step 3. 3-{3-[1-(3-Carboxy-8-chloro-1-cyclopropyl-6-fluoro-4-oxo-1,4-dihydroquinolin-7-yl)-pyrrolidin-3-ylcarbamoyl]-azetidin-1-yl}rifamycin S: To a solution of 3-[(3-carboxy-2,5-dioxo-pyrrolidin-1-yl-ester)-azetidine-1-yl]-rifamycin S (0.1 mmol) in DMF was added 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl) (62 mg, 0.15 mmol) and triethylamine (100 μL). The resulting mixture was heated in a 35° C. oil bath for 18 hours before the addition of dichloromethane and water. The aqueous layer was adjusted to pH 4 using 0.5 N HCl. The separated aqueous layer was further extracted with dichloromethane (3×). The combines organic phase was wash with brine (1×), dried over Na$_2$SO$_4$, concentrated in vacuo to give black solid, which was purified by preparative thin layer chromatography (10% methanol in dichloromethane) to give the title compound as a black solid. MS: (M+H$^+$) 1142.

EXAMPLE 44

(R/S)-3-{3-[1-(3-Carboxy-1-cyclopropyl-6-fluoro-8-methoxy-4-oxo-1,4-dihydroquinolin-7-yl)-pyrrolidin-3-ylcarbamoyl]-azetidin-1-yl}rifamycin S

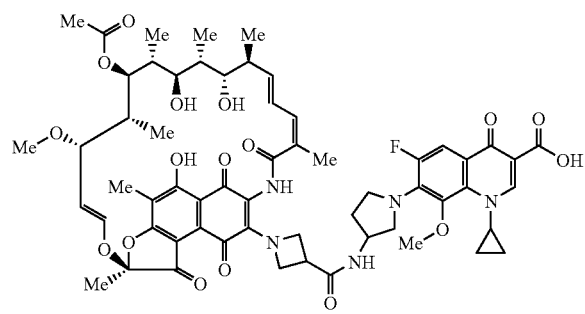

The title compound was prepared by using the same procedure as described for the preparation of Example 43 except 7-(3-amino-pyrrolidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (10% yield). MS: (M+H$^+$) 1138.

EXAMPLE 45

3-{3-[4-(3-Carboxy-1-cyclopropyl-6-fluoro-8-methoxy-4-oxo-1,4-dihydroquinolin-7-yl)-piperazin-1-ylcarbonyl]-azetidin-1-yl}rifamycin S

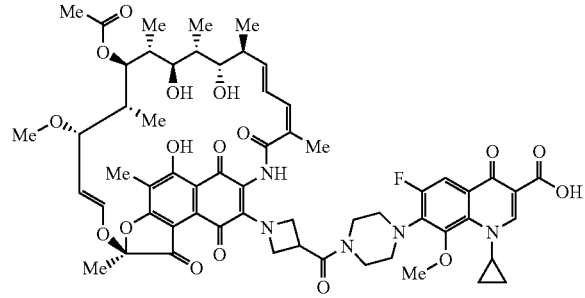

The title compound was prepared by using the same procedure as described for the preparation of Example 43 except 1-cyclopropyl-6-fluoro-8-methoxy-4-oxo-7-piperazin-1-yl-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (5% yield). MS: (M+H$^+$) 1138.

EXAMPLE 46

3-{3-[1-(3-Carboxy-1-cyclopropyl-6-fluoro-8-methoxy-4-oxo-1,4-dihydroquinolin-7-yl)-piperidin-3-ylcarbamoyl]-azetidin-1-yl}rifamycin S

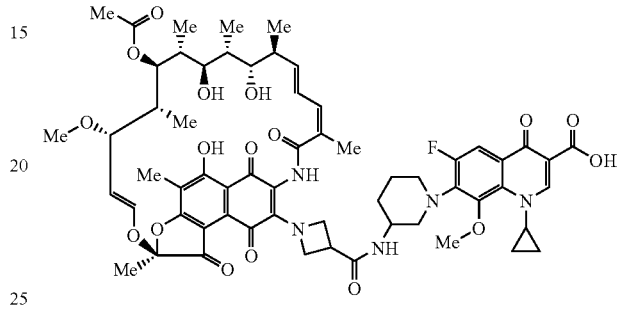

The title compound was prepared by using the same procedure as described for the preparation of Example 43 except 7-(3-amino-piperidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (16% yield). MS: (M+H$^+$) 1152.

EXAMPLE 47

3-{3-[1-(3-Carboxy-1-cyclopropyl-6-fluoro-8-methoxy-4-oxo-1,4-dihydroquinolin-7-yl)-azetidin-3-ylcarbamoyl]-azetidin-1-yl}rifamycin S

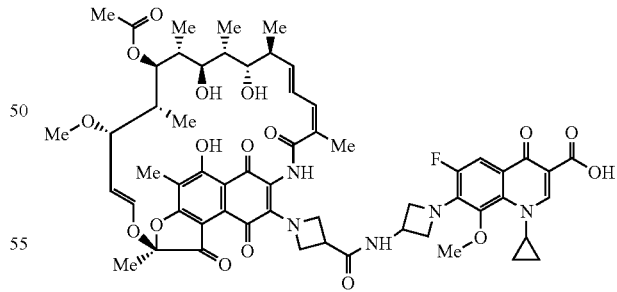

The title compound was prepared by using the same procedure as described for the preparation of Example 43 except 7-(3-amino-azetidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (7% yield). MS: (M+H$^+$) 1124.

EXAMPLE 48

3-{3-(4-[1-(5-methyl-acetamidyl-2-oxo-oxazolidin-3-yl)-5-fluoro-phen-4-yl]-piperazin-1-ylcarbonyl)-azetidin-1-yl}-rifamycin S

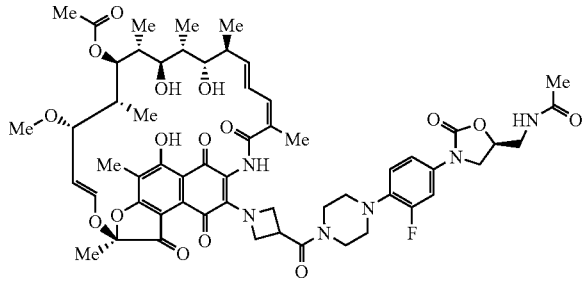

The title compound was prepared by using the same procedure as described for the preparation of Example 43 except N-[3-(3-fluoro-4-piperazin-1-yl-phenyl)-2-oxo-oxazolidin-5-ylmethyl]-acetamide was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (5% yield). MS: (M+H$^+$) 1113.

EXAMPLE 49

(R/S)-3-{4-[1-(3-Carboxy-8-chloro-1-cyclopropyl-6-fluoro-4-oxo-1,4-dihydroquinolin-7-yl)-pyrrolidin-3-ylcarbamoyl]-piperidin-1-yl}rifamycin S

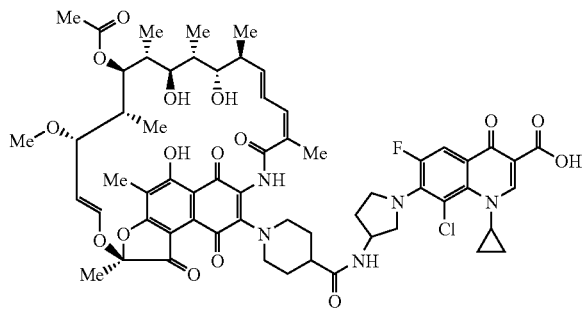

Step 1. 3-[(4-Carboxy)-piperidin-1-yl]-rifamycin S: The title compound was prepared by using the same procedure as described for the preparation of Example 10 except isonipecotic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The product was isolated as a black solid (95% yield). MS: (M+H$^+$) 723.

Step 2. 3-[(4-Carboxy-2,5-dioxo-pyrrolidin-1-yl-ester)-piperidin-1-yl]-rifamycin S: To a solution of 3-[(3-carboxy)-piperidin-1-yl]-rifamycin S (329 mg, 0.4 mmol) in THF was added EDC (192 mg, 1.0 mmol), N-hydroxy succinimide (162 mg, 1.4 mmol) and DMAP (8 mg, 0.08 mmol). The resulting mixture was heated in a 35° C. oil bath for 18 hours before adding large amount of ethyl acetate and water. The separated organic phase was further washed with water (2×), brine (1×), dried over Na$_2$SO$_4$, concentrated in vacuo to give a black solid. It was used for the next step without further purification. MS: (M+H$^+$) 920.

Step 3. 3-{4-[1-(3-Carboxy-8-chloro-1-cyclopropyl-6-fluoro-4-oxo-1,4-dihydroquinolin-7-yl)-pyrrolidin-3-ylcarbamoyl]-piperidin-1-yl}rifamycin S: To a solution of 3-[(4-carboxy-2,5-dioxo-pyrrolidin-1-yl-ester)-piperidin-1-yl]-rifamycin S (0.1 mmol) in DMF was added 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl) (62 mg, 0.15 mmol) and triethylamine (100 μL). The resulting mixture was heated in a 35° C. oil bath for 18 hours before addition of dichloromethane and water. The aqueous layer was adjusted to pH 4 using 0.5 N HCl. The separated aqueous layer was further extracted with dichloromethane (3×). The combines organic phase was wash with brine (1×), dried over Na$_2$SO$_4$, concentrated in vacuo to give a black solid, which was purified by preparative thin layer chromatography (10% methanol in dichloromethane) to give the title compound as a mixture of diastereomers as a black solid (13% yield). MS: (M+H$^+$) 1170.

EXAMPLE 50

(R/S)-3-{4-[1-(3-Carboxy-1-cyclopropyl-6-fluoro-8-methoxy-4-oxo-1,4-dihydroquinolin-7-yl)-pyrrolidin-3-ylcarbamoyl]-piperidin-1-yl}rifamycin S

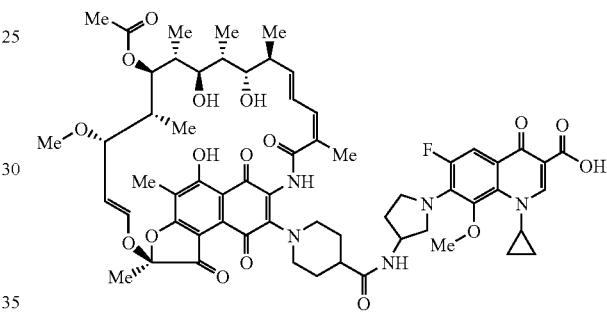

The title compound was prepared by using the same procedure as described for the preparation of Example 49 except 7-(3-amino-pyrrolidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (24% yield). MS: (M+H$^+$) 1166.

EXAMPLE 51

3-{4-[4-(3-Carboxy-1-cyclopropyl-6-fluoro-8-methoxy-4-oxo-1,4-dihydroquinolin-7-yl)-piperazin-1-ylcarbonyl]-piperidin-1-yl}rifamycin S

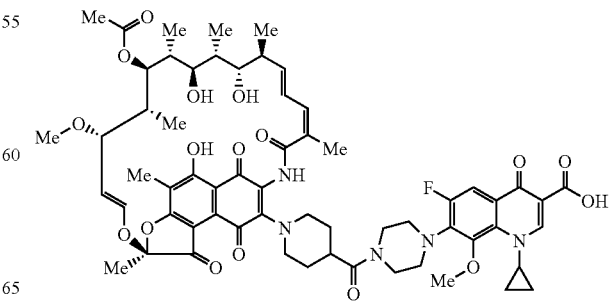

The title compound was prepared by using the same procedure as described for the preparation of Example 49 except 1-cyclopropyl-6-fluoro-8-methoxy-4-oxo-7-piperazin-1-yl-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (23% yield). MS: (M+H$^+$) 1166; $^1$H NMR (400 MHz, CDCl$_3$) δ13.26 (s, 1 H), 8.80 (s, 1 H), 7.89 (d, J=12.6 Hz, 1 H), 7.58 (s, 1 H), 7.11 (m, 1 H), 6.35 (d, J=10.7 Hz, 1 H), 6.17 (dd, J=15.6 and 6.3 Hz, 1 H), 6.05 (d, J=12.6 Hz, 1 H), 5.08 (m, 2 H), 4.09-3.27 (complex pattern), 3.07 (s, 3 H), 3.03 (m, 2 H), 2.74 (m, 1 H), 2.34 (m, 1 H), 2.24 (s, 3 H), 2.11 (s, 3 H), 2.05 (s, 3 H), 1.95 (m, 1 H), 1.78 (m, 4 H), 1.72 (s, 3 H), 1.66 (m 1 H), 1.22 (d, J=7.9 Hz, 2 H), 1.02 (d, J=7.0 Hz, 3 H), 1.00 (m, 2 H), 0.86 (d, J=6.9 Hz, 3 H), 0.69 (d, J=6.9 Hz, 3 H), 0.16 (d, J=7.2 Hz, 3 H).

EXAMPLE 52

(R/S)-3-}(4-[1-(3-Carboxy-1-cyclopropyl-6-fluoro-8-methoxy-4-oxo-1,4-dihydroquinolin-7-yl)-piperidin-3-ylcarbamoyl]-piperidin-1-yl}rifamycin S

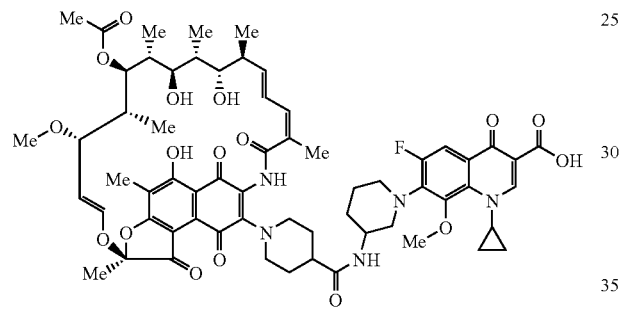

The title compound was prepared by using the same procedure as described for the preparation of Example 49 except (R/S)-7-(3-amino-piperidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a mixture of diastereomers as a black solid (22% yield). MS: (M+H$^+$) 1180.

EXAMPLE 53

3-{4-[1-(3-Carboxy-1-cyclopropyl-6-fluoro-8-methoxy-4-oxo-1,4-dihydroquinolin-7-yl)-azetidin-3-ylcarbamoyl]-piperidin-1-yl}rifamycin S

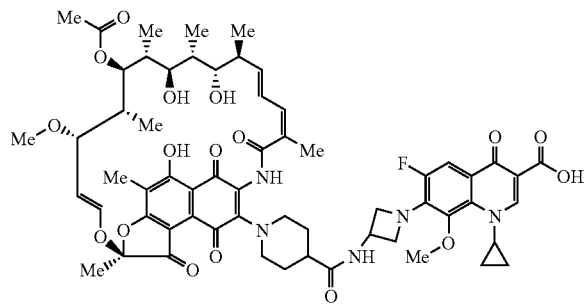

The title compound was prepared by using the same procedure as described for the preparation of Example 49 except 7-(3-amino-azetidin-1-yl)-1-cyclopropyl-6-fluoro-8-methoxy-4-oxo-1,4-dihydro-quinoline-3-carboxylic acid was used instead of 7-(3-amino-pyrrolidin-1-yl)-8-chloro-1-cyclopropyl-6-fluoro-4-oxo-1,4-dihydro-quinoline-3-carboxylic acid hydrochloride (clinafloxacin HCl). The title compound was isolated as a black solid (13% yield). MS: (M+H$^+$) 1152; $^1$H NMR (400 MHz, CDCl$_3$) δ 13.26 (s, 1 H), 8.64 (s, 1 H), 7.99 (s, 1 H), 7.54 (s, 1 H), 7.51 (s, 1 H), 6.97 (m, 1 H), 6.57 (d, J=7.6 Hz, 1 H), 6.32 (d, J=10.1 Hz, 1 H), 6.14 (dd, J=15.8 and 6.4 Hz, 1 H), 6.05 (d, J=12.5 Hz, 1 H), 5.07 (m, 2 H), 4.86 (m, 1 H), 2.66 (m, 2 H), 6.15 (m, 2 H), 3.89 (m, 4 H), 3.55 (s, 3 H), 3.44 (d, J=4.5 Hz, 1 H), 3.31 (m, 1 H), 3.07 (s, 3 H), 3.00 (m, 2 H), 2.39 (m, 1 H), 2.22 (s, 3 H), 2.05 (s, 3 H), 1.95 (m, 3 H), 1.78 (m, 2 H), 1.71 (s, 3 H), 1.66 (m, 4 H), 1.22 (m, 2 H), 1.01 (d, J=7.1 Hz, 3 H), 0.85 (d, J=7.1 Hz, 3 H), 0.68 (d, J=6.1 Hz, 3 H), 0.14 (d, J=6.2 Hz, 3 H).

EXAMPLE 54

(R/S)-3-{4-[1-(3-Crboxy-1-(2,3-difluoro-phenyl)-6-fluoro-4-oxo-1,4-dihydro[1,8]naphthyridine-7-yl)-pyrrolidin-3-yl]-piperazin-1-yl}-rifamycin S

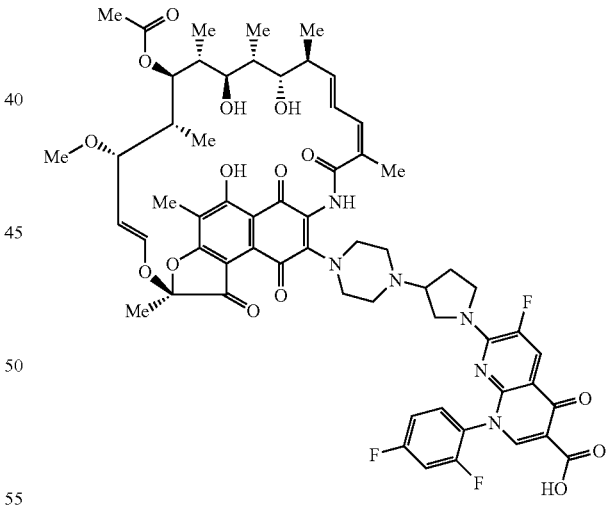

The title compound was prepared by using the same procedure as described for the preparation of Example 10 except 1-(2,4-difluoro-phenyl)-6-fluoro-4-oxo-7-(3-piperazin-1-yl-pyrrolidin-1-yl)-1,4-dihydro-[1,8]naphthyridine-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a mixture of diastereomers as a black solid (58% yield). MS: (M+H$^+$) 1167.

EXAMPLE 55

3-[1-(3-Carboxy-1-cyclopropyl-6-fluoro-4-oxo-1,4-dihydro-[1,8]naphthyridine-7-yl)-piperazin-4-yl]-rifamycin S

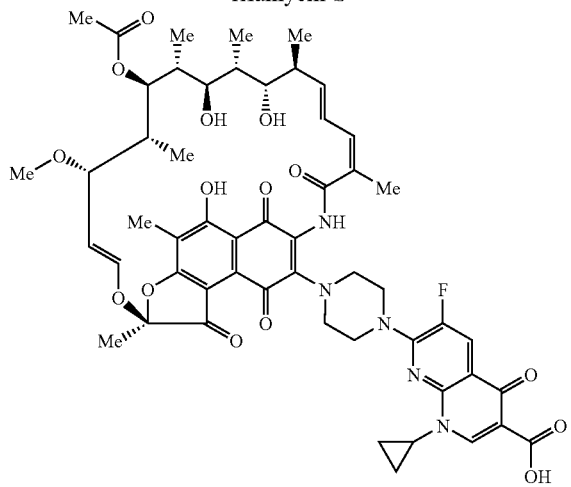

The title compound was prepared by using the same procedure as described for the preparation of Example 10 except 1-cyclopropyl-6-fluoro-4-oxo-7-piperazin-1-yl-1,4-dihydro-[1,8]naphthyridine-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a black solid (53% yield). MS: (M+H$^+$) 1026; $^1$H NMR (400 MHz, CDCl$_3$) δ 13.10 (s, 1 H), 8.27 (s, 1 H), 8.09 (d, J=13.4 Hz, 1 H), 7.61 (s, 1 H), 7.09 (dd, J=15.9 and 11.0 Hz, 1 H), 6.36 (d, J=15.8 Hz, 1 H), 6.19 (dd, J=16.4 and 7.1 Hz, 1 H), 6.06 (d, J=13.5 Hz, 1 H), 5.09 (m, 2H), 4.17-3.40 (complex pattern), 3.08 (s, 3 H), 3.03 (d, J=10.3 Hz, 1 H), 2.33 (m, 1 H), 2.26 (s, 3 H), 2.11 (s, 3 H), 2.06 (s, 3 H), 1.77 (m, 3 H), 1.73 (s, 3 H), 1.66 (m, 3 H), 1.26 (d, J=7.0 Hz, 2 H), 1.05 (m, 2 H), 1.01 (d, J=7.0 Hz, 3 H), 0.82 (d, J=7.1 Hz, 3 H), 0.69 (d, J=7.3 Hz, 3 H), 0.17 (d, J=7.1 Hz, 1 H).

EXAMPLE 56

(R/S)-3-{4-[1-(3-Carboxy-1-cyclopropyl-6-fluoro-8-methoxy-4-oxo-1,4-dihydroquinoline-7-yl)-pyrrolidin-3-yl-cyclopropyl]-piperazin-1-yl}-rifamycin S

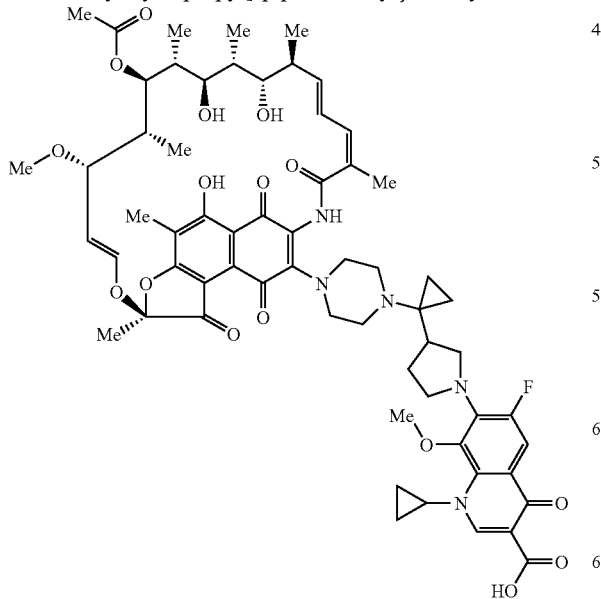

The title compound was prepared by using the same procedure as described for the preparation of Example 10 except 1-cyclopropyl-6-fluoro-8-methoxy-4-oxo-7-[3-(1-piperazin-1-yl-cyclopropyl)-pyrrolidin-1-yl]-1,4-dihydro-quinoline-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a black solid (25% yield). MS: (M+H$^+$) 1164.

EXAMPLE 57

(R/S)-3-{4-[1-(3-Carboxy-8-chloro-1-cyclopropyl-6-fluoro-4-oxo-1,4-dihydroquinoline-7-yl)-pyrrolidin-3-yl-cyclopropyl]-piperazin-1-yl}-rifamycin S

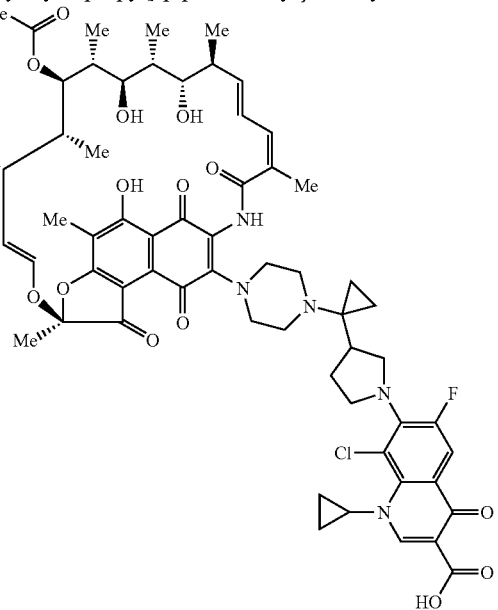

The title compound was prepared by using the same procedure as described for the preparation of Example 10 except 8-chloro-1-cyclopropyl-6-fluoro-4-oxo-7-[3-(1-piperazin-1-yl-cyclopropyl)-pyrrolidin-1-yl]-1,4-dihydro-quinoline-3-carboxylic acid was used instead of 1-cyclopropyl-6-fluoro-8-methoxy-7-(3-methyl-piperazin-1-yl)-4-oxo-1,4-dihydro-quinoline-3-carboxylic acid (gatifloxacin). The title compound was isolated as a black solid (25% yield). MS: (M+H$^+$) 1164.

EXAMPLE 58

(R/S)-3-{4-({1-[1-(3-Carboxy-1-(2,3-difluoro-phenyl)-6-fluoro-4-oxo-1,4-dihydro-[1,8]naphthyridine-7-yl)-pyrrolidin-3-yl]-cyclopropyl}-methyl-amino)-piperidin-1-yl}-rifamycin S

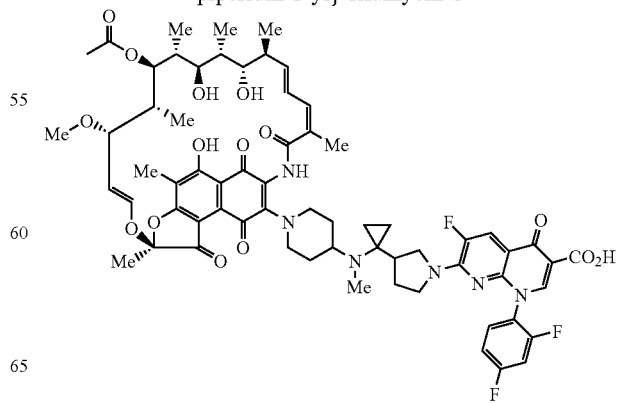

ESI MS m/z 1235.5 (M+H)+. 1H NMR (400 MHz, CDCl3) 1:1 mixture of diastereomers δ 13.31 (s, 1H), 8.60 (s, 1H), 8.00 (d, J=12.5 Hz, 1H), 7.51 (s, 1H), 7.43-7.29 (m, 1H), 7.15-7.00 (m, 1H), 6.34 (d, J=11.0 Hz, 1H), 6.20-6.09 (m, 1H), 6.04 (d, J=11.7 Hz, 1H), 5.12-5.02 (m, 2H), 4.10-3.18 (m, 9H), 3.08 (s, 3H), 3.04-2.90 (m, 3H), 2.76-2.27 (m, 7H), 2.24 (s, 3H), 2.22-2.12 (m, 4H), 2.06 (s, 3H), 2.02-1.74 (m, 6H), 1.72 (s, 3H), 1.69-1.08 (m, 6H), 1.00 (d, J=6.3 Hz, 3H), 0.87-0.76 (m, 3H), 0.72-0.60 (d, J=7.0 Hz, 3H), 0.60-0.27 (m, 2H), 0.15 (d, J=6.3 Hz, 3H).

EXAMPLE 59

(R/S)-3-{4-[1-(3-Carboxy-1-cyclopropyl-6-fluoro-4-oxo-1,4-dihydro-1-[1,8]naphthyridine-7-yl)-3-methoxyiminopyrrolidin-4-ylmethylamino]-piperidin-1-yl}rifamycin S

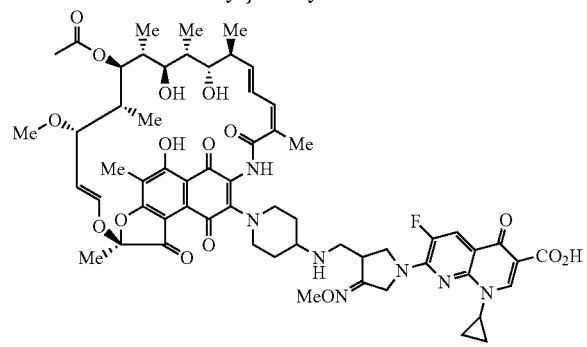

The title compound was prepared by using the same procedure as described for the preparation of Example 29 except (R/S)-7-(3-aminomethyl-4-methoxyiminopyrrolidin-1-yl)-1-cyclopropyl-6-fluoro-4-oxo-1,4-dihydro-[1,8]naphthyridine-3-carboxylic acid was used instead of (R/S)-7-[3-Aminopyrrolidin-1-yl]-8-chloro-1-cyclopropyl-6-fluoro-4-oxo-1,4-dihydro-quinoline-3-carboxylic acid. The title compound was isolated as a mixture of diastereomers as a black solid. ESI MS m/z 1166.5 (M+H)+. 1H NMR (400 MHz, CDCl3) 1:1 mixture of diastereomers δ 13.47-13.19 (br s, 1H), 8.71 (s, 1H), 8.05 (d, J=11.7 Hz, 1H), 7.51 (s, 1H), 7.10-6.93 (m, 1H), 3.91 (s, 3H), 3.73-3.10 (m, 12H), 3.07 (s, 3H), 3.06-2.63 (m, 8H), 2.40-2.29 (m, 3H), 2.24 (s, 3H), 2.06 (s, 3H), 2.01-1.75 (m, 9H), 1.72 (s, 3H), 1.71-1.04 (m, 9H), 1.01 (d, J=7.0 Hz, 3H), 0.85 (d, J=7.0 Hz, 3H), 0.68 (d, J=7.0 Hz, 3H), 0.15 (d, J=6.3 Hz, 3H).

EXAMPLE 60

3-[2-[3-Carboxy-1-(2,4-difluorophenyl)-6-fluoro-4-oxo-1,4-dihydronaphthyridin-7-yl]-2,7-diaza-spiro[4.5]decyl)-7-yl]rifamycin S

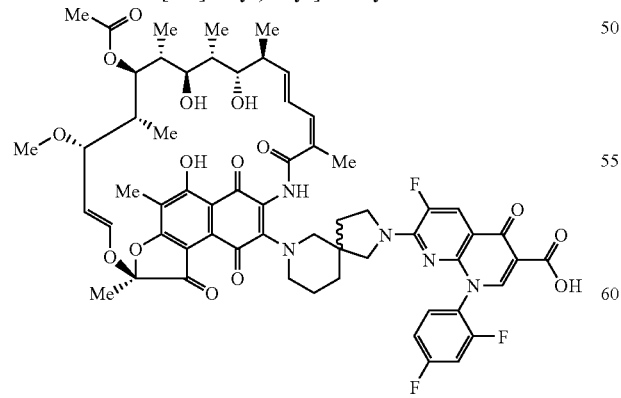

The title compound was prepared by using the same procedure as described for the preparation of Example 4 except 7-(2,7-diaza-spiro[4.5]dec-2-yl)-1-(2,4-difluoro-phenyl)-6-fluoro-4-oxo-1,4-dihydro-[1,8]naphthyridine-3-carboxylic acid (the linker was prepared as described in P. W. Smith, et al.; *J. Med. Chem.;* 1995; 38(19); 3772-3779 using N-Boc 3-piperidone instead of N-Boc 4-piperidone) was used in place of 1-cyclopropyl-6-fluoro-4-oxo-7-(piperazin-1-yl)-1,4-dihydro-quinoline-3-carboxylic acid (ciprofloxacin). The title product was isolated as a purple solid. ESI MS m/z 1152 (M+H+); 1H NMR (400 MHz, CDCl3): δ 13.0 (s, 1H), 8.60-8.40 (m, 1H), 7.98-7.95 (m, 1H), 7.45-7.30 (m, 1H), 7.00-6.80 (m, 2H), 6.30-5.75 (m, 3H), 5.00-4.80 (m, 1H), 4.60-4.40 (m, 1H), 4.00-3.75 (m, 2H), 3.65-2.80 (m, 5H), 1.80-1.20 (m, 24 H), 0.90-0.86 (m, 3H), 0.80-0.60 (m, 3H), 0.40-0.20 (m, 3H), −0.95-0.05 (m, 3H).

One skilled in the art readily appreciates that the disclosed invention is well adapted to carry out the mentioned and inherent objectives. Linkers, fluorophores, ligands of bacterial ribosome and functional equivalents thereof, pharmaceutical compositions, treatments, methods, procedures and techniques described herein are presented as representative of the preferred embodiments and are not intended as limitations of the scope of the invention. Thus, other uses will occur to those skilled in the art that are encompassed within the spirit and scope of the described invention.

What is claimed is:

1. A rifamycin compound having a structural formula I or II:

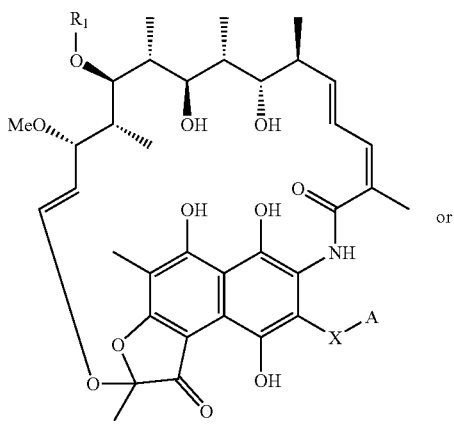

I or

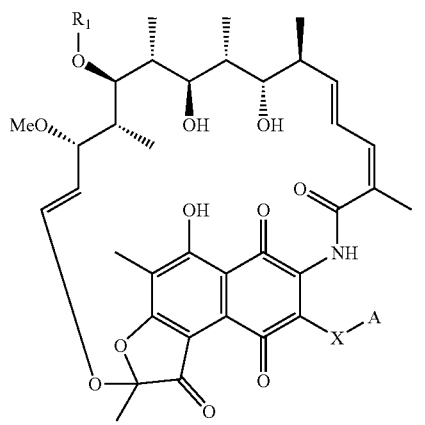

II wherein,
A is a quinolone or its pharmacophore, covalently coupled to a linker group "X";
X is a linker group that is covalently coupled to both rifamycin moiety at C-3 position and "A", wherein "X"

is selected from one or a combination of 1 to 3 of the following structural elements:
a) —$(C_1$-$C_6)$alkylene,
b) —$(C_1$-$C_6)$alkenylene,
c) —$(C_1$-$C_6)$alkynylene,
d) —$(C_3$-$C_8)$cycloalkylene,
e) —O—,
f) —C(H)=N—, provided the group was not directly attached to the C-3 position of the rifamycin moiety,
g) —C(=O)—,
h) —C(=N—O—$R_{13}$)—, wherein $R_{13}$ represents hydrogen, $(C_1$-$C_6)$alkyl, or substituted $(C_1$-$C_6)$alkyl,
i) —S(O)$_n$—, wherein n is a number between 0 and 2,
j) —N($R_{14}$)—, wherein $R_{14}$ represents hydrogen, $(C_1$-$C_6)$alkyl, or substituted $(C_1$-$C_6)$alkyl, and
k) arylene,
   wherein, the carbon or nitrogen atoms of the linker group "X" can be substituted by 1 to 3 substituents selected from $(C_1$-$C_6)$alkyl, substituted $(C_1$-$C_6)$alkyl, amino, $(C_1$-$C_6)$alkylamino, di$(C_1$-$C_6)$alkylamino, hydroxyl, and $(C_1$-$C_6)$alkoxy;
   $R_1$ is hydrogen, or acetyl,
   or a pharmaceutically acceptable salt of the structural formula I or II.

2. The rifamycin compound of claim 1, wherein $R_1$ is hydrogen.

3. The rifamycin compound of claim 1, wherein X comprises any one or a combination of the following structures:

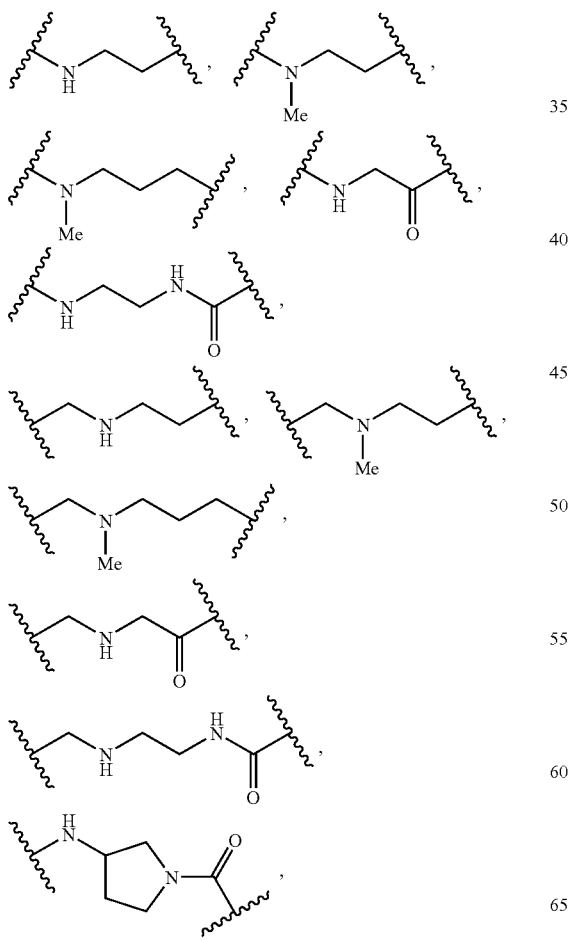

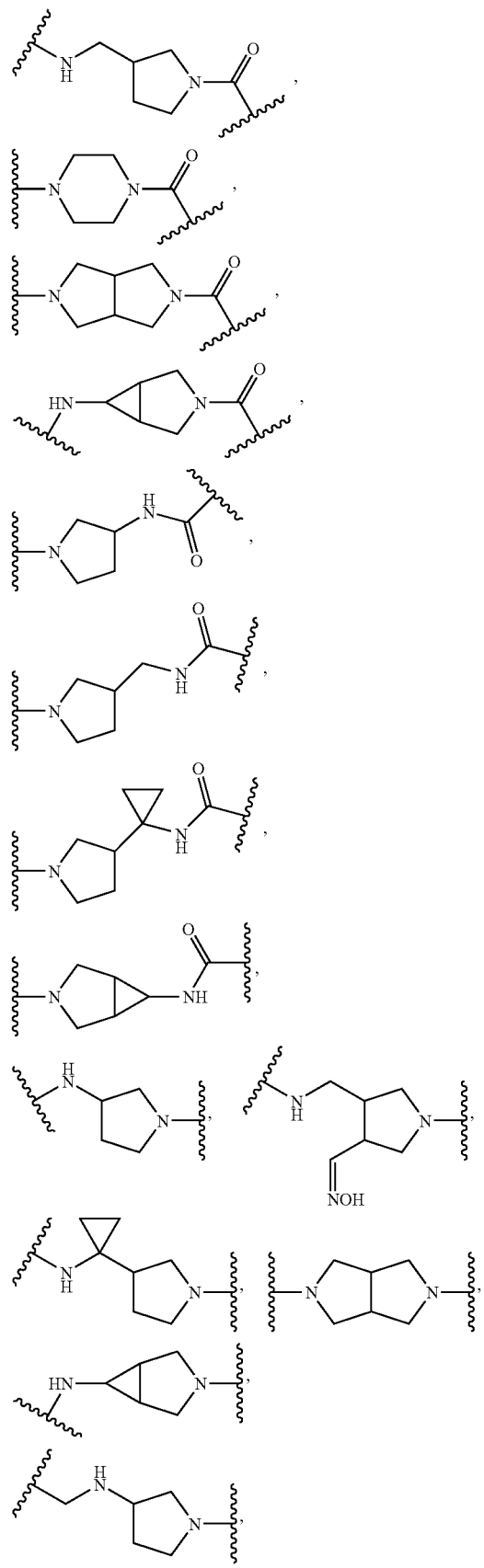

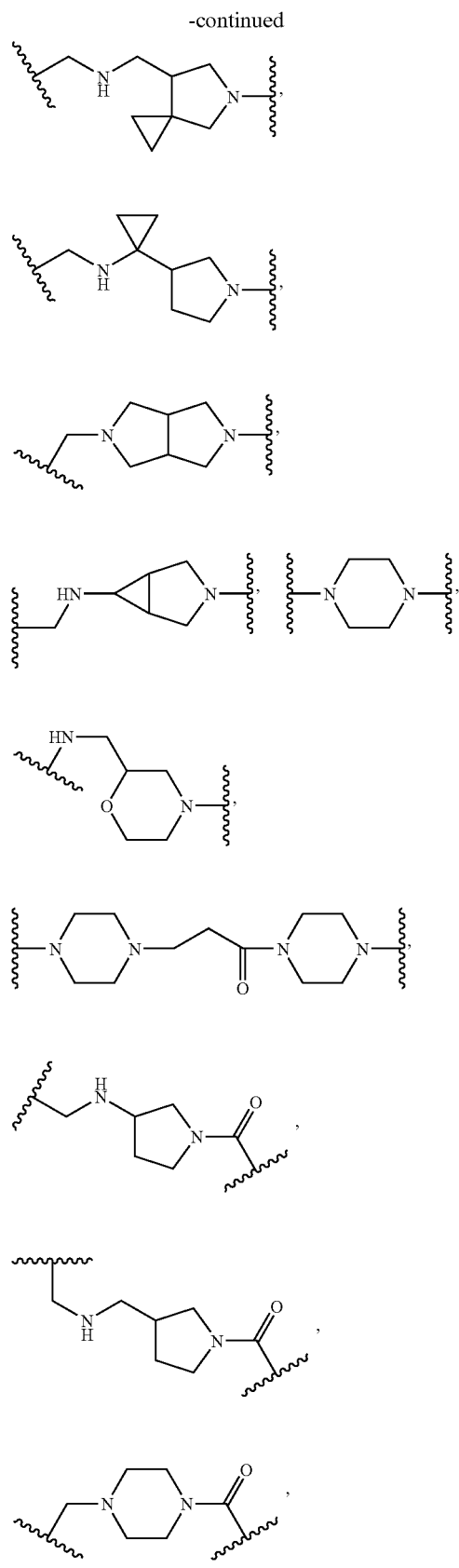
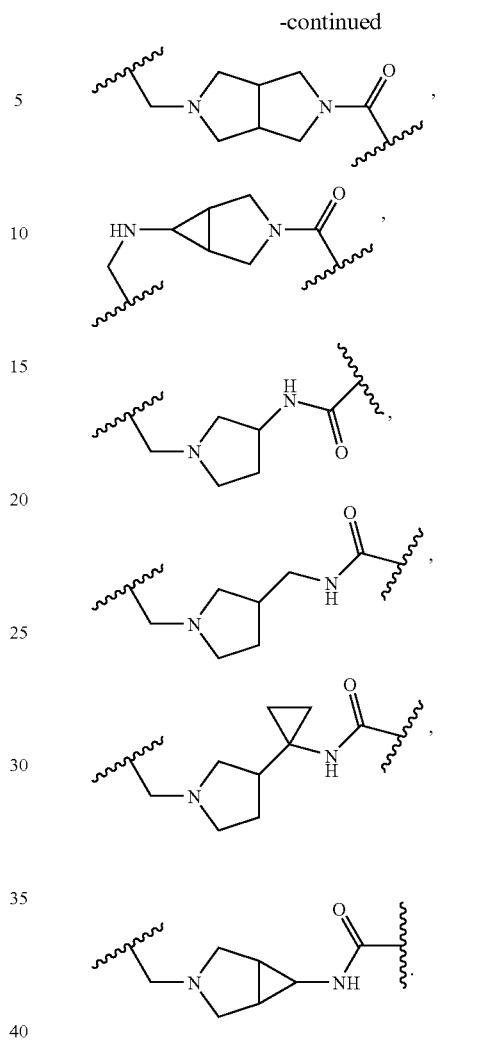
4. A rifamycin compound having a structural formula III or IV:
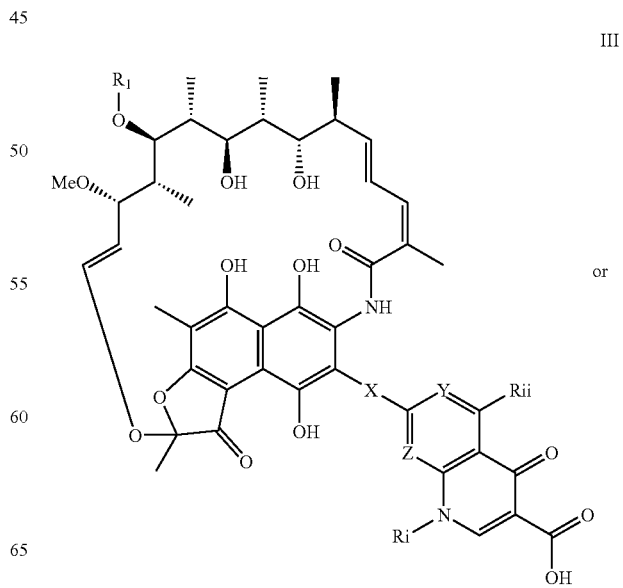

-continued

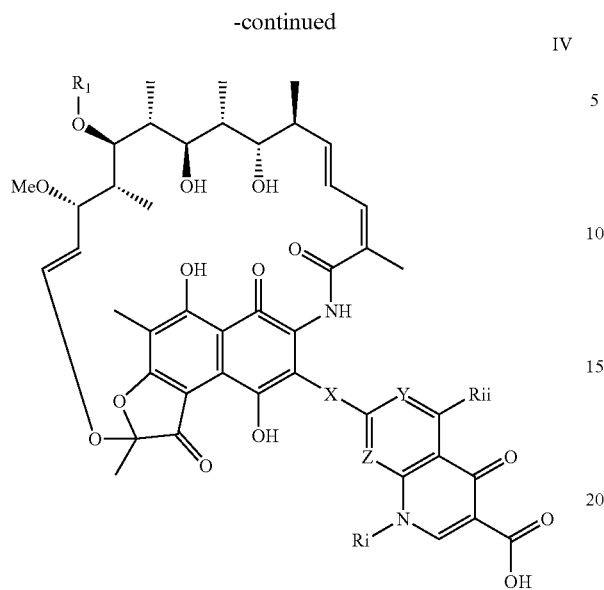

IV wherein,
$R_i$ is $(C_1-C_6)$alkyl, $(C_3-C_6)$cycloalkyl, substituted $(C_3-C_6)$ cycloalkyl, aryl, substituted aryl, heteroaryl, or substituted heteroaryl;
$R_{ii}$ is hydrogen, halogen, amino, nitro or methyl group;
Y is C—H, C—F, or N;
Z is C—H, C—F, C—Cl, C—CN, C—$CF_3$, C-Me, C—OMe, C—$OCH_2F$, C—$OCHF_2$, or N;
$R_1$ is hydrogen, or acetyl;
X is selected from one or a combination of two to three of the following structural elements:

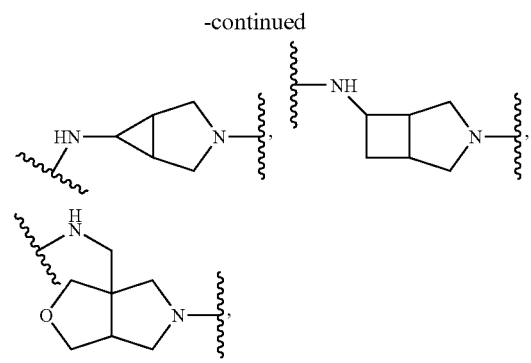

-continued

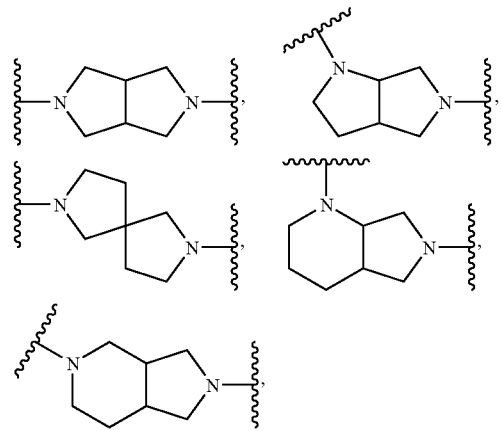

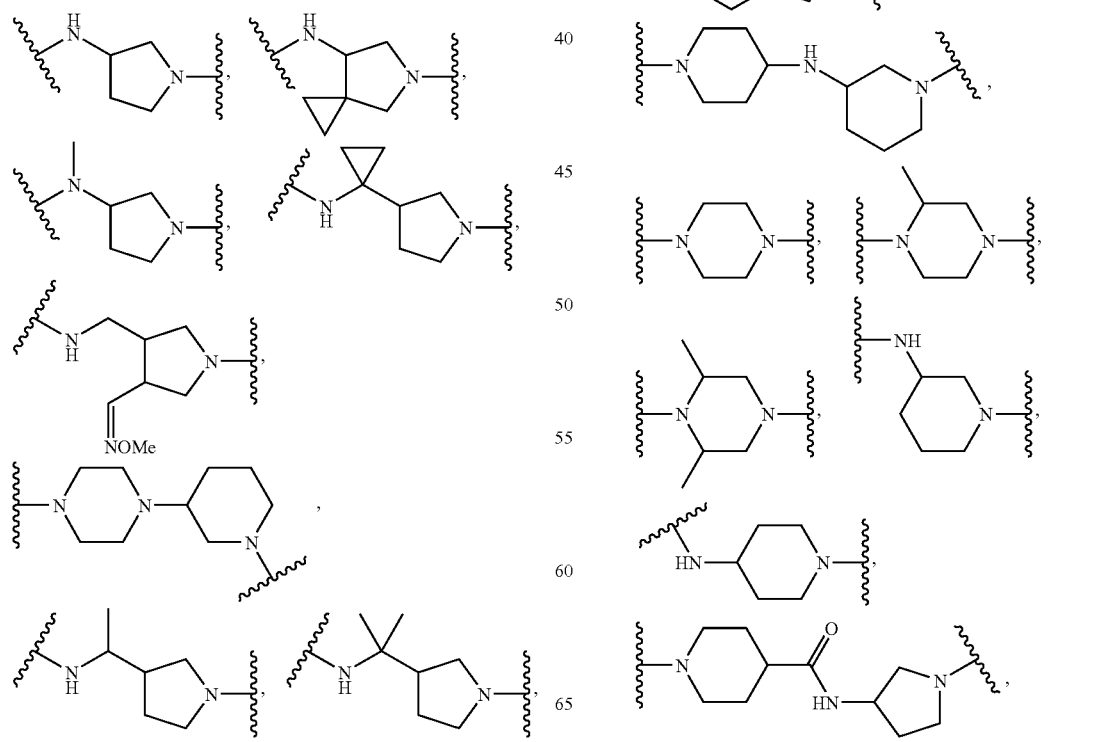

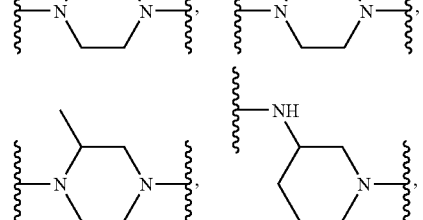

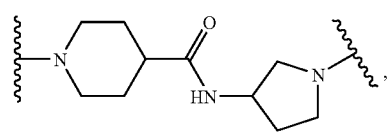

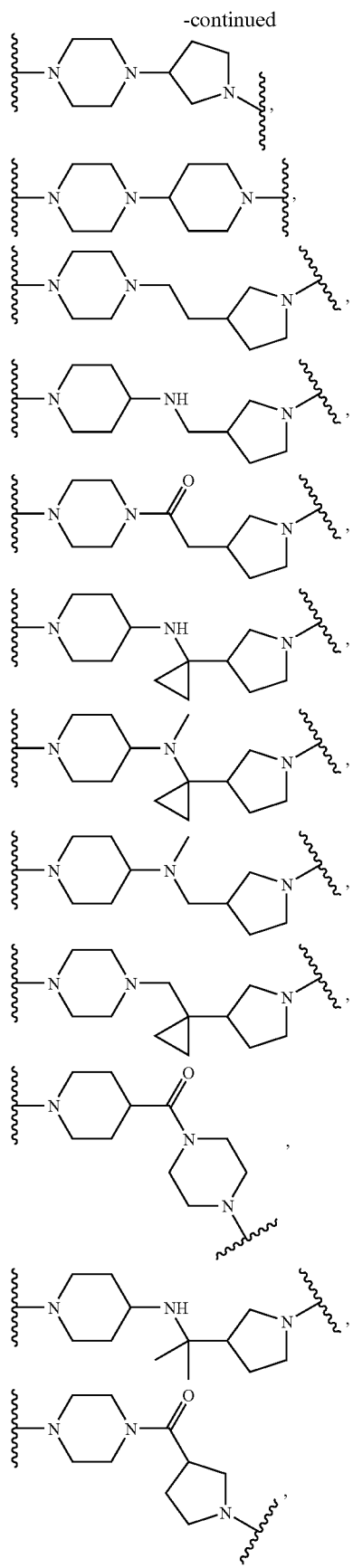

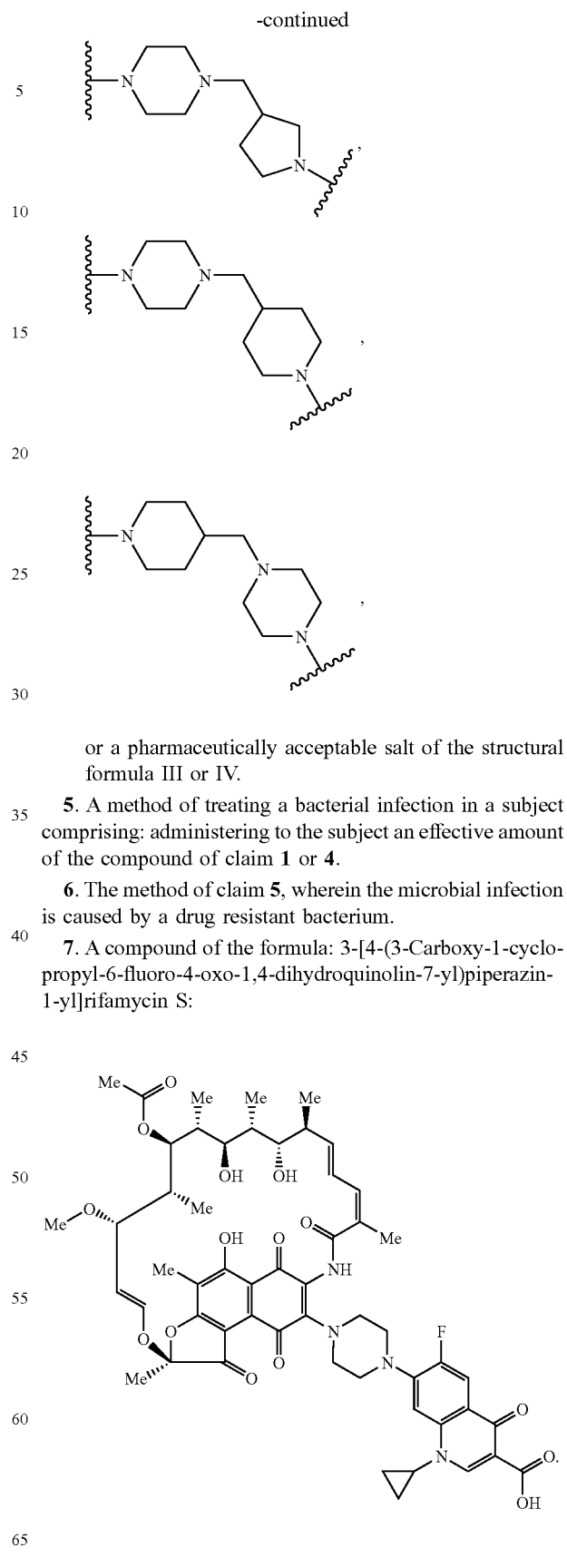

or a pharmaceutically acceptable salt of the structural formula III or IV.

5. A method of treating a bacterial infection in a subject comprising: administering to the subject an effective amount of the compound of claim 1 or 4.

6. The method of claim 5, wherein the microbial infection is caused by a drug resistant bacterium.

7. A compound of the formula: 3-[4-(3-Carboxy-1-cyclopropyl-6-fluoro-4-oxo-1,4-dihydroquinolin-7-yl)piperazin-1-yl]rifamycin S:

8. A compound of the formula: 3-[4-(3-Carboxy-1-(2,4-difluorophenyl)-6-fluoro-4-oxo-1,4-dihydronaphthyridin-7-yl)piperazin-1-yl]rifamycin S:

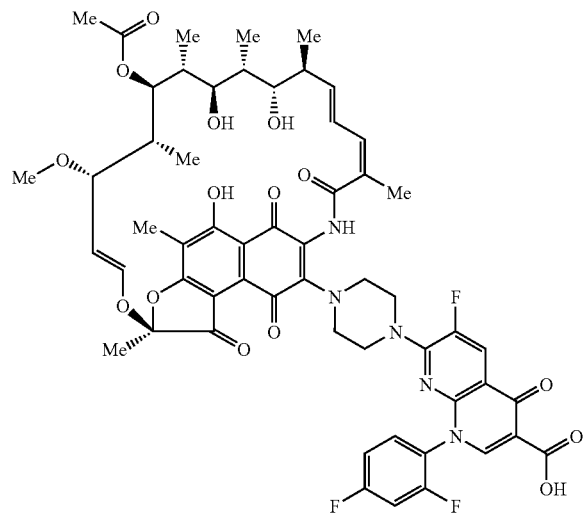

9. A compound of the formula: 3-[4-[3-[1-[3-Carboxy-1-(2,4-difluorophenyl)-6-fluoro-4-oxo-1,4-dihydronaphthyridin-7-yl]piperidin-4-yl]propyl]piperidin-1-yl]rifamycin S:

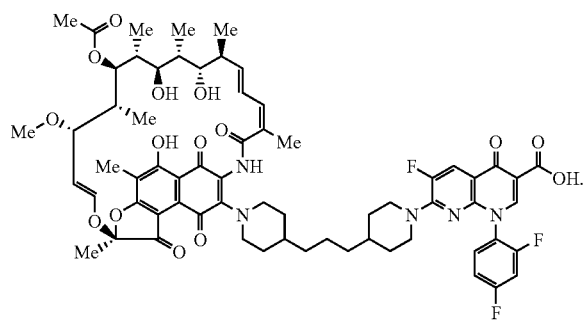

10. A compound of the formula: (R/S)-3-[1-(3-Carboxy-8-chloro-1-cyclopropyl-6-fluoro-4-oxo-1,4-dihydroquinolin-7-yl)-pyrrolidin-3-ylamino]rifamycin S:

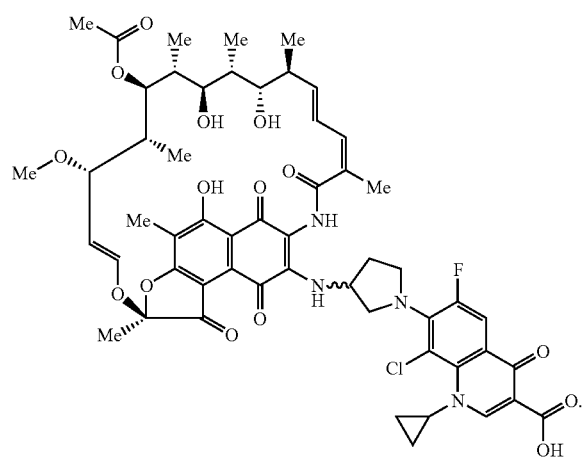

11. A compound of the formula: (R)-3-[1-(3-Carboxy-1-cyclopropyl-6-fluoro-4-oxo-1,4-dihydroquinolin-7-yl)-pyrrolidin-3-ylamino]rifamycin S:

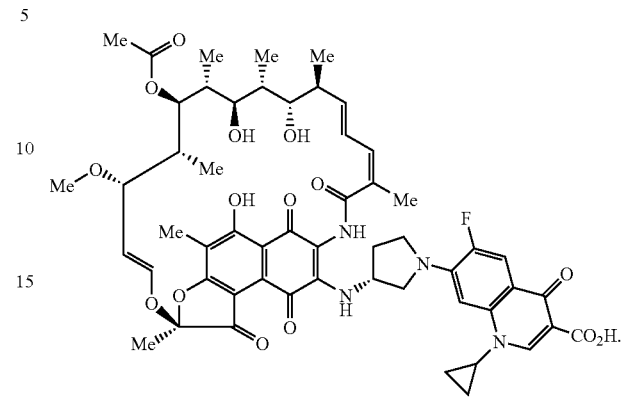

12. A compound of the formula: (S)-3-[1-(3-Carboxy-1-cyclopropyl-6-fluoro-4-oxo-1,4-dihydroquinolin-7-yl)-pyrrolidin-3-ylamino]rifamycin S:

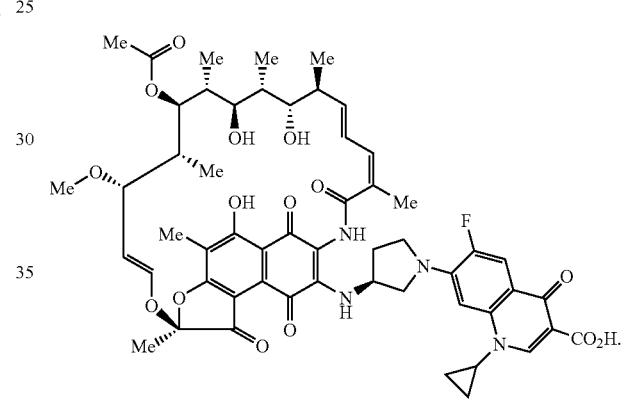

13. A compound of the formula: (R,S)-3-[4-(3-Carboxy-1-cyclopropyl-6-fluoro-8-methoxy-4-oxo-1,4-dihydroquinolin-7-yl)-2-methylpiperazin-1-yl]rifamycin S:

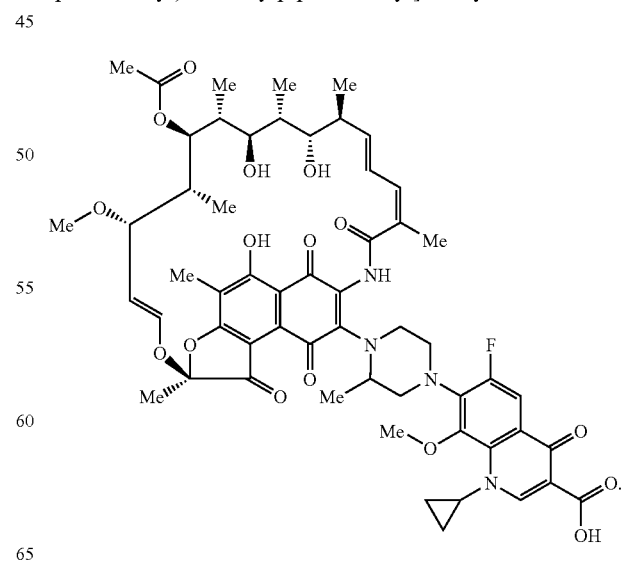

14. An antibiotic, comprising a compound of the formula: (R,S)-3-[4-(3-Carboxy-1-ethyl-6,8-difluoro-4-oxo-1,4-dihydroquinolin-7-yl)-2-methyl-piperazinyl]rifamycin SV:

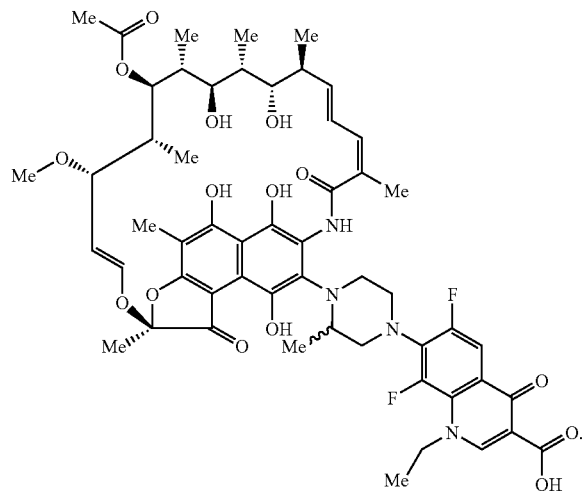

15. A compound of the formula: 3-[4-[3-Carboxy-1-cyclopropyl-6-fluoro-4-oxo-(1,4-dihydroquinolin-7-yl)]-piperazin-1-ylmethyl]rifamycin SV:

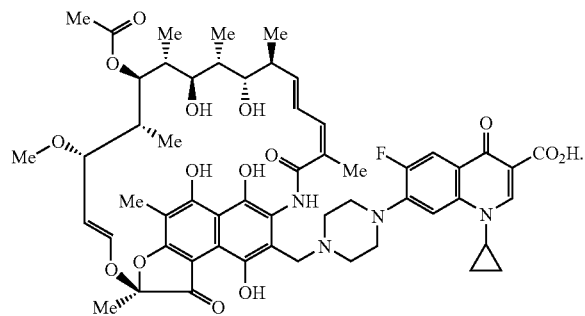

16. A compound of the formula: (R/S)-3-[1-(8-Chloro-3-carboxy-1-cyclopropyl-6-fluoro-4-oxo-1,4-dihydroquinolin-7-yl)-pyrrolidinyl-3-aminomethyl]rifamycin SV:

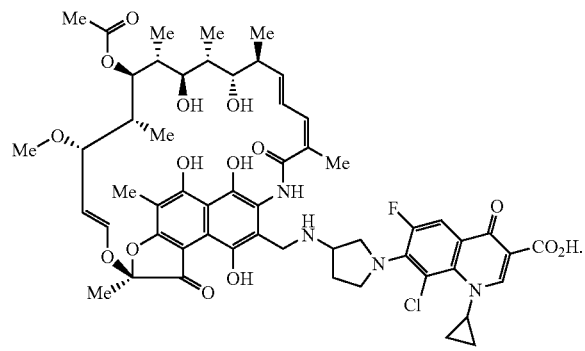

17. A compound of the formula: 3-[4-[3-carboxy-1-(2,4-Difluoro-phenyl)-6-fluoro-4-oxo-1,4-dihydro-[1,8]naphthyridin-7-yl]piperazin-1-ylmethyl]rifamycin SV:

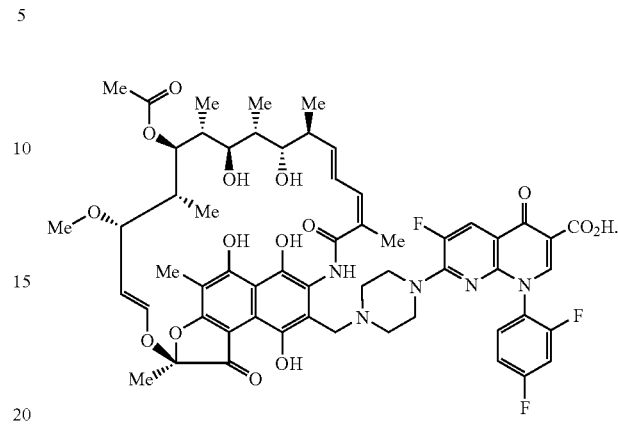

18. A compound of the formula: (R)-3-[1-(3-carboxy-1-cyclopropyl-6-fluoro-4-oxo-1,4-dihydroquinolin-7-yl)-pyrrolidinyl-3-aminomethyl]rifamycin SV:

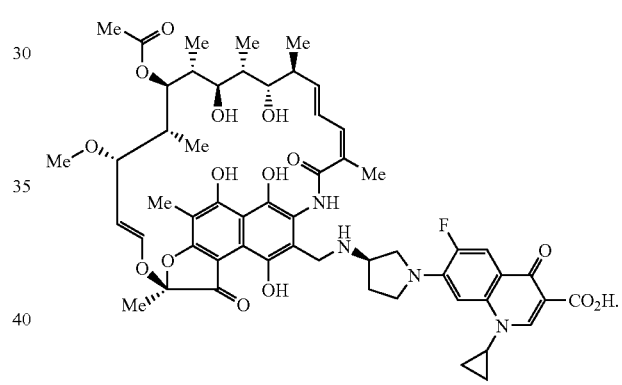

19. A compound of the formula: (S)-3-[1-(3-carboxy-1-cyclopropyl-6-fluoro-4-oxo-1,4-dihydroquinolin-7-yl)-pyrrolidinyl-3-aminomethyl]rifamycin SV:

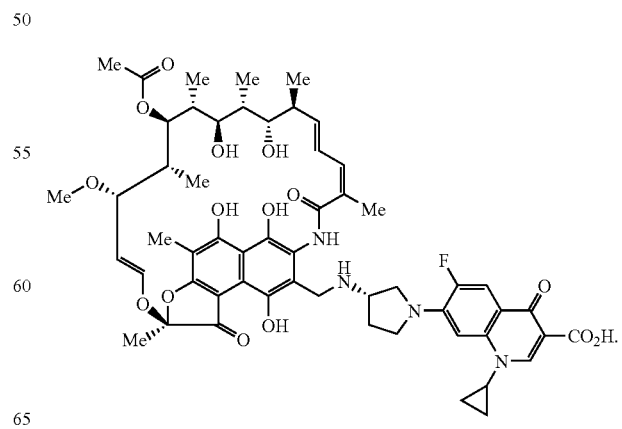

20. A compound of the formula: 3-[1-(3-Carboxy-1-cyclopropyl-6-fluoro-4-oxo-1,4-dihydroquinolin-7-yl)azetidin-3-methylamino)rifamycin S:

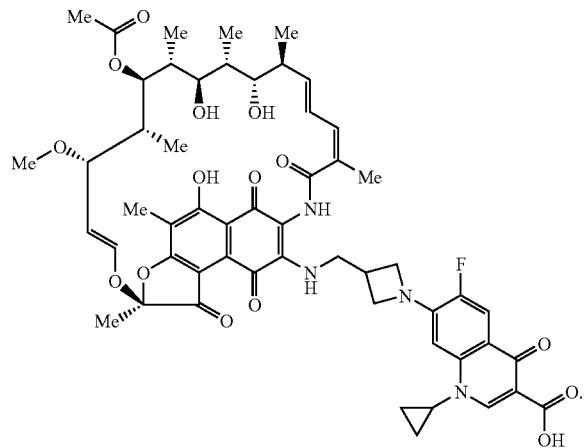

21. A compound of the formula: (R/S)-3-[4-(3-Carboxy-1-cyclopropyl-6-fluoro-8-methoxy-4-oxo-1,4-dihydroquinolin-7-yl)-piperazin-1-yl]rifamycin S:

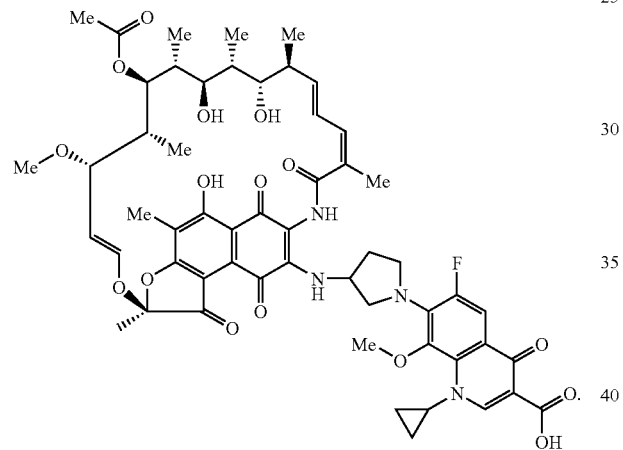

22. A compound of the formula: (R/S)-3-[1-(3-Carboxy-1-cyclopropyl-6-fluoro-8-methoxy-4-oxo-1,4-dihydroquinolin-7-yl)-pyrrolidin-3-ylamino-methyl]rifamycin S:

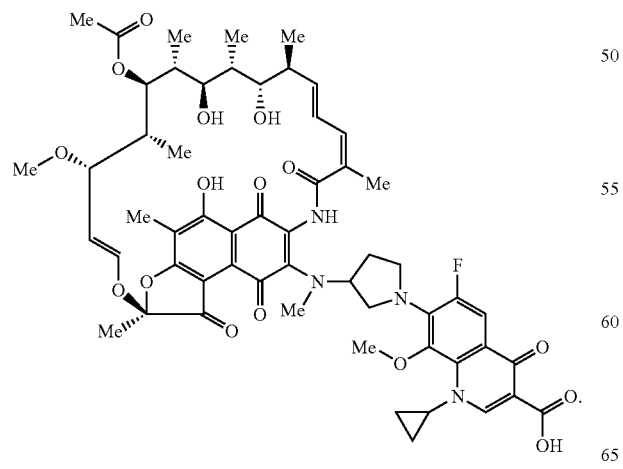

23. A compound of the formula: (R/S)-3-{4-[1-(3-Carboxy-8-chloro-1-cyclopropyl-6-fluoro-4-oxo-1,4-dihydroquinolin-7-yl)-pyrrolidin-3-ylamino]-piperidin-1-yl}rifamycin S:

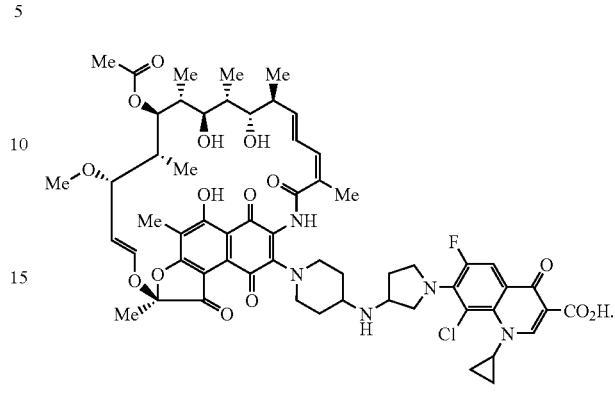

24. A compound of the formula: (R/S)-3-{4-[1-(3-Carboxy-1-cyclopropyl-6-fluoro-8-methoxy-4-oxo-1,4-dihydroquinolin-7-yl)-pyrrolidin-3-ylamino]-piperidin-1-yl}rifamycin S:

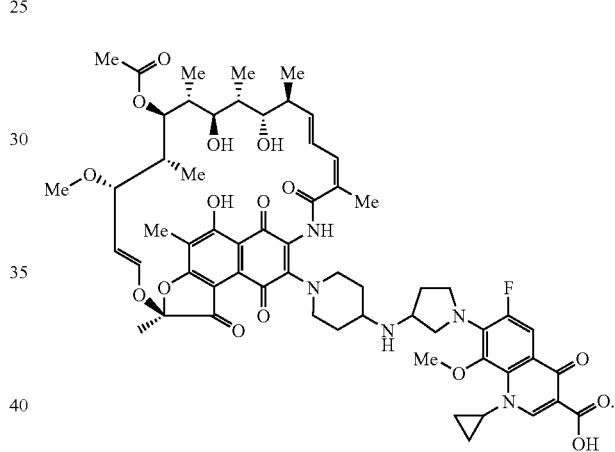

25. A compound of the formula: 3-{4-[1-(3-Carboxy-1-cyclopropyl-6-fluoro-8-methoxy-4-oxo-1,4-dihydroquinolin-7-yl)-piperazin-4-yl]-piperidin-1-yl}rifamycin S:

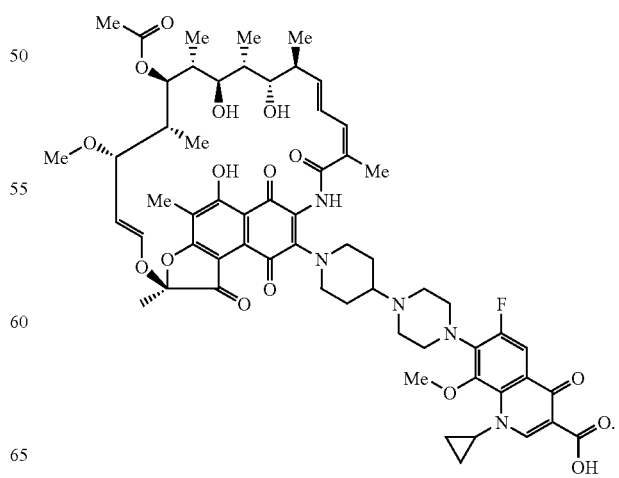

26. A compound of the formula: (R/S)-3-{4-[1-(3-Carboxy-1-cyclopropyl-6-fluoro-8-methoxy-4-oxo-1,4-dihydroquinolin-7-yl)-piperidin-3-ylamino]-piperidin-1-yl}rifamycin S:

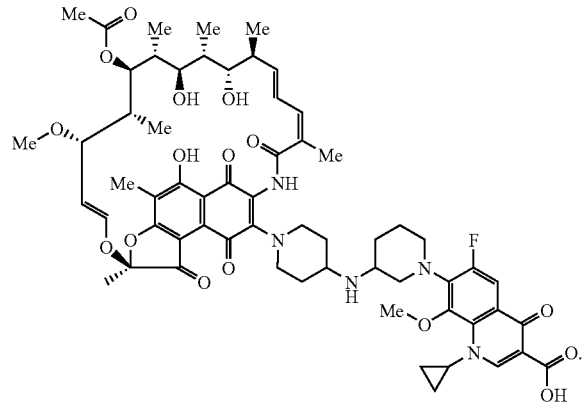

27. A compound of the formula: 3-{4-[1-(3-Carboxy-1-cyclopropyl-6-fluoro-8-methoxy-4-oxo-1,4-dihydroquinolin-7-yl)-azetidin-3-ylamino]-piperidin-1-yl}rifamycin S:

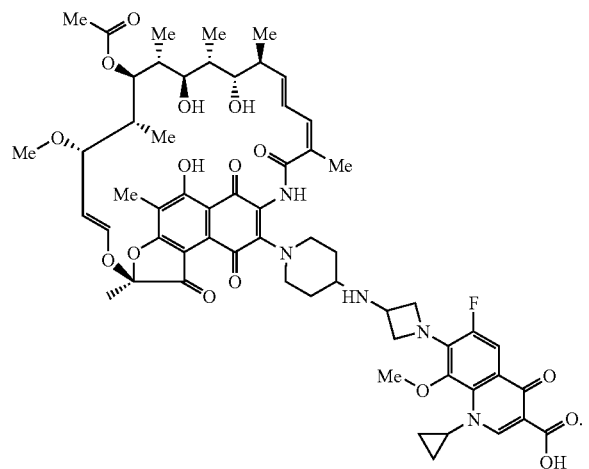

28. A compound of the formula: (R/S)-3-{4-[1-(3-Carboxy-1-cyclopropyl-6-fluoro-8-methoxy-4-oxo-1,4-dihydroquinolin-7-yl)-pyrrolidin-3-ylamino-methyl]-piperidin-1-yl}rifamycin S:

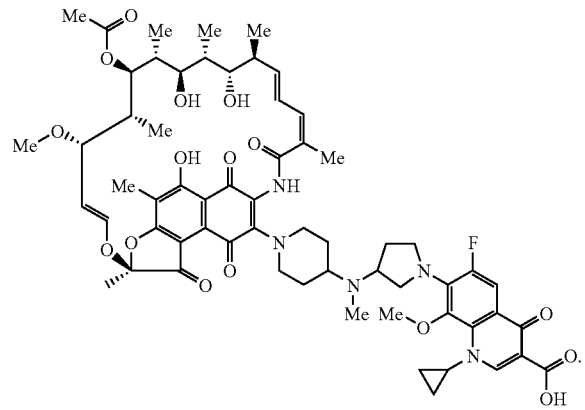

29. A compound of the formula: 3-{4-[6-(3-Carboxy-1-cyclopropyl-6-fluoro-8-methoxy-4-oxo-1,4-dihydroquinolin-7-yl)-octahydro-pyrrolo[3,4-b]-pyrridin-1-yl]-piperidin-1-yl}rifamycin S:

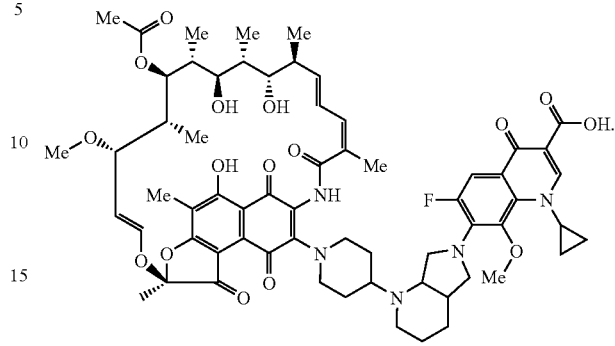

30. A compound of the formula: (R/S)-3-{4-[1-(3-Carboxy-8-chloro-1-cyclopropyl-6-fluoro-4-oxo-1,4-dihydroquinolin-7-yl)-(pyrrolidin-3-ylmethyl)-amino]-piperidin-1-yl}rifamycin S:

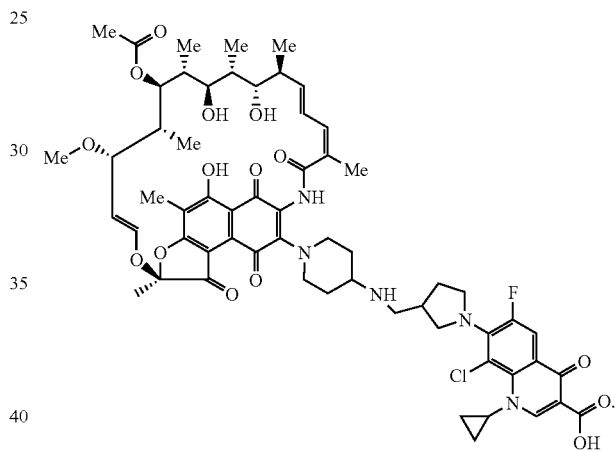

31. A compound of the formula: (R/S)-3-{4-[1-(3-Carboxy-1-(2,3-difluoro-phenyl)-6-fluoro-4-oxo-1,4-dihydro[1,8]naphthyridine-7-yl)-(pyrrolidin-3-ylmethyl)-amino]-piperidin-1-yl}rifamycin S:

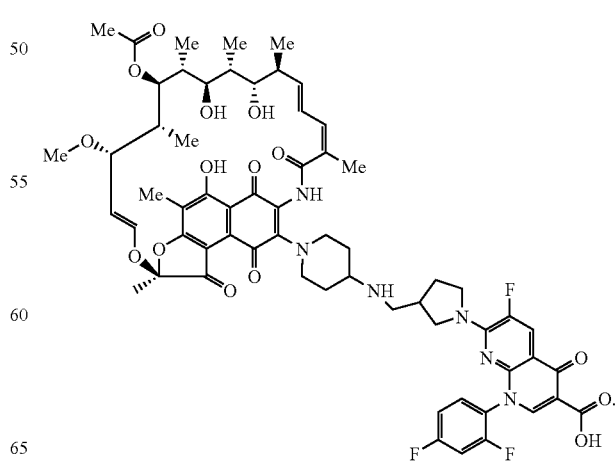

32. A compound of the formula: 3-{4-[1-(3-Carboxy-8-chloro-1-cyclopropyl-6-fluoro-4-oxo-1,4-dihydroquinolin-7-yl)-piperazin-4-yl]-piperidin-1-yl}rifamycin S:

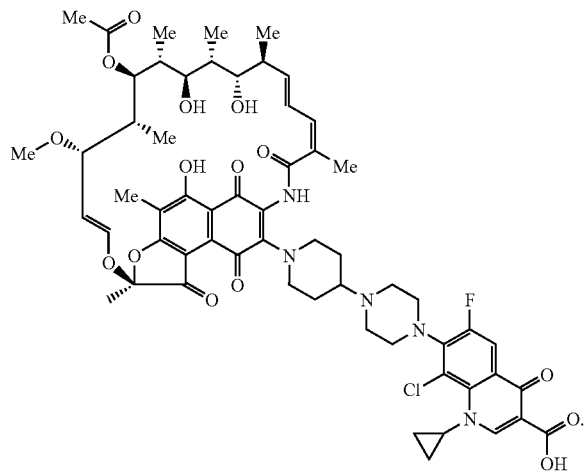

33. A compound of the formula: 3-{4-[1-(3-Carboxy-1-cyclopropyl-6-fluoro-8-methoxy-4-oxo-1,4-dihydroquinolin-7-yl)-pyrrolidin-3-ylethylamino]-piperidin-1-yl}rifamycin S:

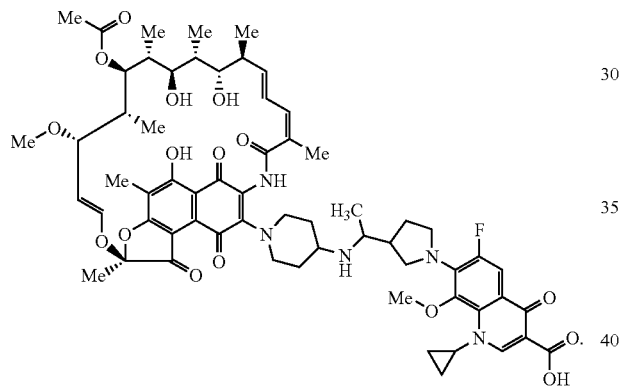

34. A compound of the formula: (R/S)-3-{4-(1-[1-(3-Carboxy-1-(2,3-difluoro-phenyl)-6-fluoro-4-oxo-1,4-dihydro-[1,8]naphthyridine-7-yl)-pyrrolidin-3-yl]-piperazin-1-yl)-piperidin-1-yl}-rifamycin S:

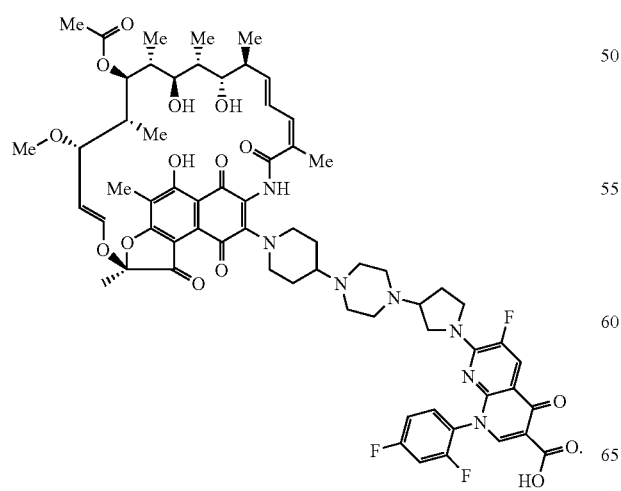

35. A compound of the formula: (R/S)-3-[4-{1-[1-(3-Carboxy-1-cyclopropyl-6-fluoro-8-methoxy-4-oxo-1,4-dihydro-quinoline-7-yl)-pyrrolidin-3-yl]-cyclopropylamino}-piperidin-1-yl]-rifamycin S:

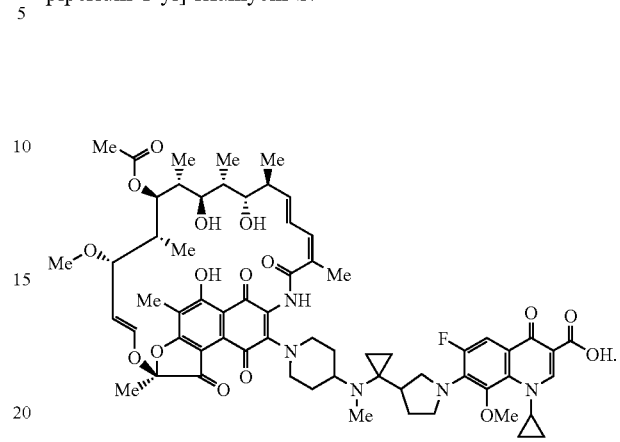

36. A compound of the formula: (R/S)-3-{4-({1-[1-(3-Carboxy-8-chloro-1-cyclopropyl-6-fluoro-4-oxo-1,4-dihydro-quinolin-7-yl)-pyrrolidin-3-yl]-cyclopropyl}-methyl-amino)-piperidin-1-yl]-rifamycin S:

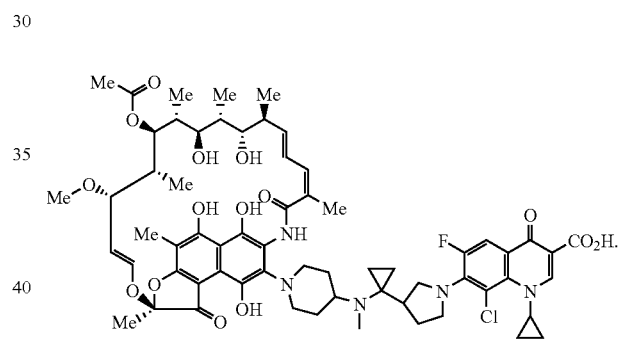

37. A compound of the formula: (R/S)-3-{3-[1-(3-Carboxy-8-chloro-1-cyclopropyl-6-fluoro-4-oxo-1,4-dihydro-quinolin-7-yl)-pyrrolidin-3-ylcarbamoyl]-azetidin-1-yl}rifamycin S:

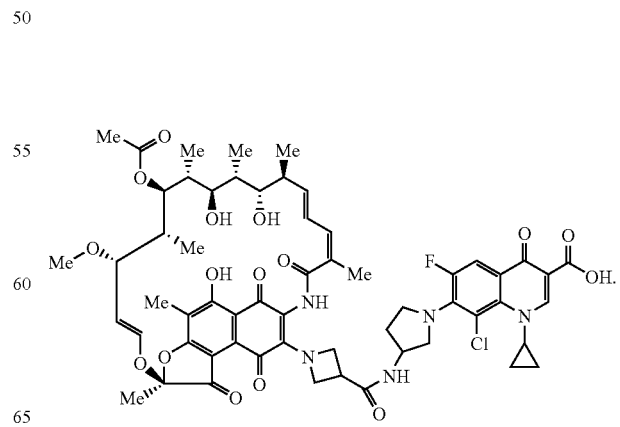

38. A compound of the formula: (R/S)-3-{3-[1-(3-Carboxy-1-cyclopropyl-6-fluoro-8-methoxy-4-oxo-1,4-dihydroquinolin-7-yl)-pyrrolidin-3-ylcarbamoyl]-azetidin-1-yl}rifamycin S:

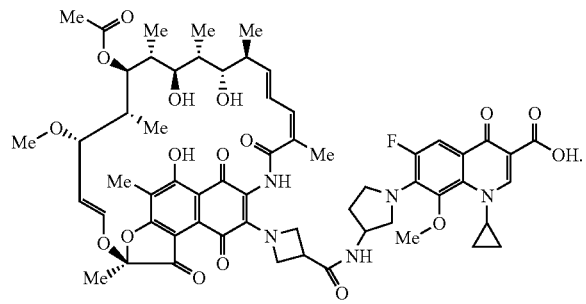

39. A compound of the formula: 3-{3-[4-(3-Carboxy-1-cyclopropyl-6-fluoro-8-methoxy-4-oxo-1,4-dihydroquinolin-7-yl)-piperazin-1-yl-carbonyl]-azetidin-1-yl}rifamycin S:

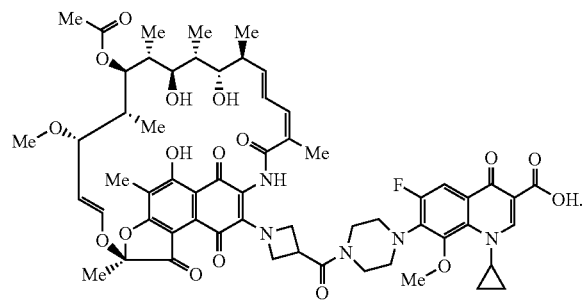

40. A compound of the formula: 3-{3-[1-(3-Carboxy-1-cyclopropyl-6-fluoro-8-methoxy-4-oxo-1,4-dihydroquinolin-7-yl)-piperidin-3-ylcarbamoyl]-azetidin-1-yl}rifamycin S:

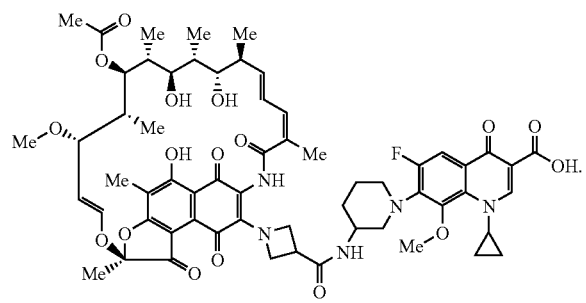

41. A compound of the formula: 3-{3-[1-(3-Carboxy-1-cyclopropyl-6-fluoro-8-methoxy-4-oxo-1,4-dihydroquinolin-7-yl)-azetidin-3-ylcarbamoyl]-azetidin-1-yl}rifamycin S:

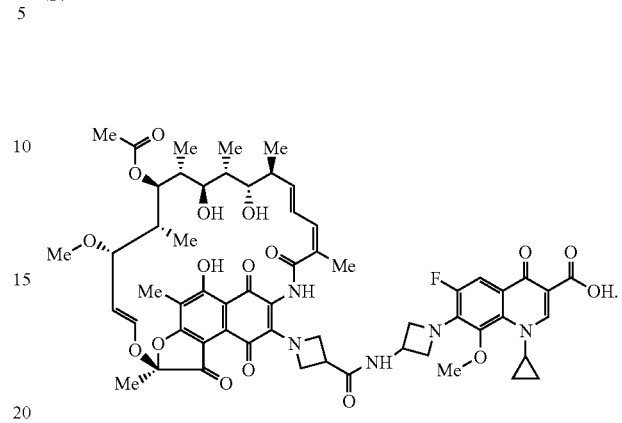

42. A compound of the formula: (R/S)-3-{4-[1-(3-Carboxy-8-chloro-1-cyclopropyl-6-fluoro-4-oxo-1,4-dihydroquinolin-7-yl)-pyrrolidin-3-ylcarbamoyl]-piperidin-1-yl}rifamycin S:

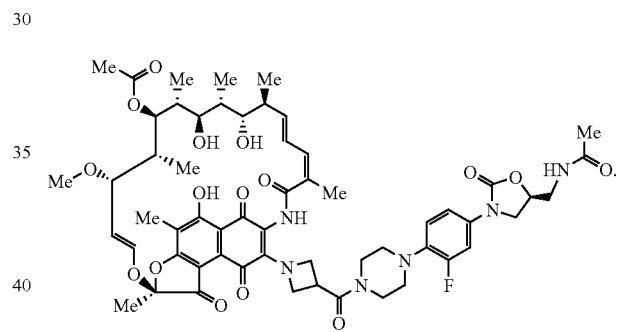

43. A compound of the formula: (R/S)-3-{4-[1-(3-Carboxy-1-cyclopropyl-6-fluoro-8-methoxy-4-oxo-1,4-dihydroquinolin-7-yl)-pyrrolidin-3-ylcarbamoyl]-piperidin-1-yl}rifamycin S:

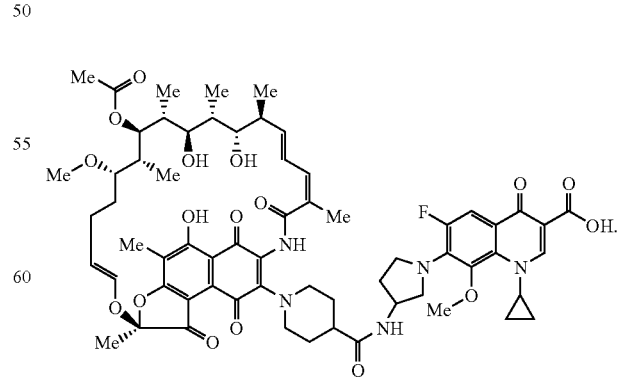

44. A compound of the formula: 3-{4-[4-(3-Carboxy-1-cyclopropyl-6-fluoro-8-methoxy-4-oxo-1,4-dihydroquinolin-7-yl)-piperazin-1-ylcarbonyl]-piperidin-1-yl}rifamycin S:

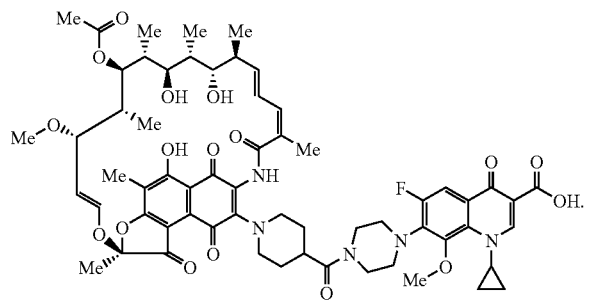

45. A compound of the formula: (R/S)-3-{4-[1-(3-Carboxy-1-cyclopropyl-6-fluoro-8-methoxy-4-oxo-1,4-dihydroquinolin-7-yl)-piperidin-3-ylcarbamoyl]-piperidin-1-yl}rifamycin S:

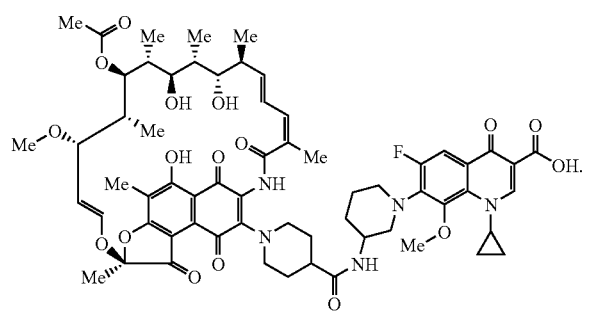

46. A compound of the formula: 3-{4-[1-(3-Carboxy-1-cyclopropyl-6-fluoro-8-methoxy-4-oxo-1,4-dihydroquinolin-7-yl)-azetidin-3-ylcarbamoyl]-piperidin-1-yl}rifamycin S:

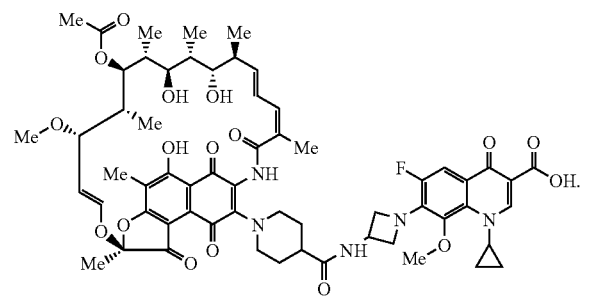

47. A compound of the formula: (R/S)-3-{4-[1-(3-Carboxy-1-(2,3-difluoro-phenyl)-6-fluoro-4-oxo-1,4-dihydro[1,8]naphthyridine-7-yl)-pyrrolidin-3-yl]-piperazin-1-yl}-rifamycin S:

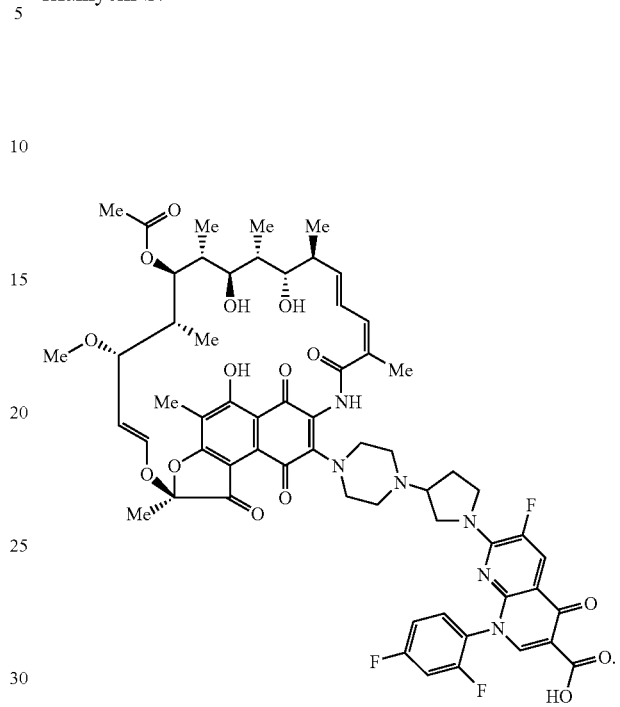

48. A compound of the formula: 3-[1-(3-Carboxy-1-cyclopropyl-6-fluoro-4-oxo-1,4-dihydro-[1,8]naphthyridine-7-yl)-piperazin-4-yl]-rifamycin S:

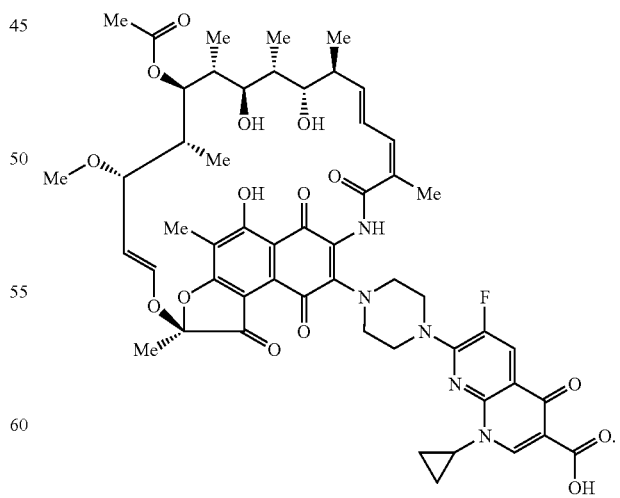

49. A compound of the formula: (R/S)-3-{4-[1-(3-Carboxy-1-cyclopropyl-6-fluoro-8-methoxy-4-oxo-1,4-dihydroquinoline-7-yl)-pyrrolidin-3-yl-cyclopropyl]-piperazin-1-yl}-rifamycin S:

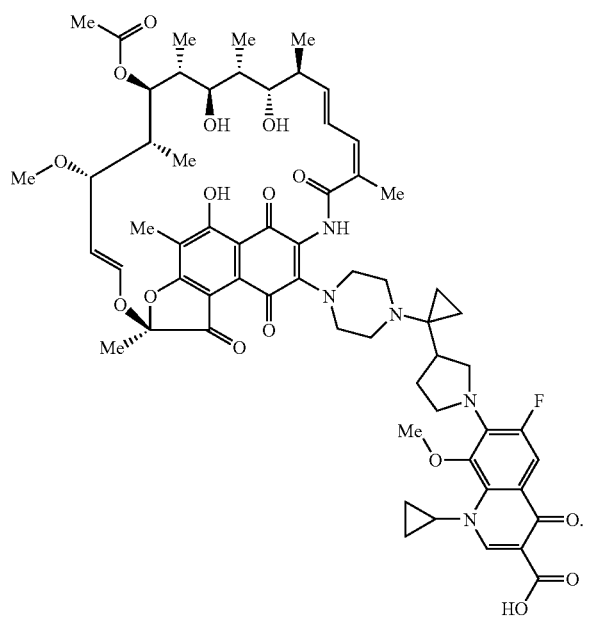

50. A compound of the formula: (R/S)-3-{4-[1-(3-Carboxy-8-chloro-1-cyclopropyl-6-fluoro-4-oxo-1,4-dihydroquinoline-7-yl)-pyrrolidin-3-yl-cyclopropyl]-piperazin-1-yl}-rifamycin S:

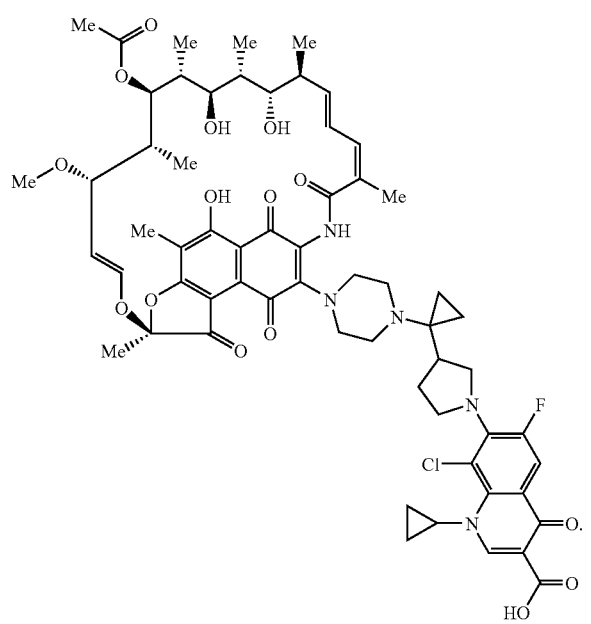

51. A compound of the formula: (R/S)-3-{4-({1-[1-(3-Carboxy-1-(2,3-difluoro-phenyl)-6-fluoro-4-oxo-1,4-dihydro-[1,8]naphthyridine-7-yl)-pyrrolidin-3-yl]-cyclopropyl}-methyl-amino)-piperidin-1-yl]-rifamycin S:

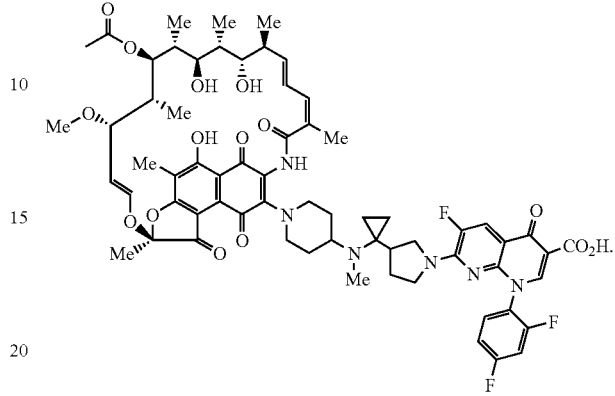

52. A compound of the formula: (R/S)-3-{4-[1-(3-Carboxy-1-cyclopropyl-6-fluoro-4-oxo-1,4-dihydro-[1,8]naphthyridine-7-yl)-3-methoxyiminopyrrolidin-4-ylmethylamino]-piperidin-1-yl}rifamycin S:

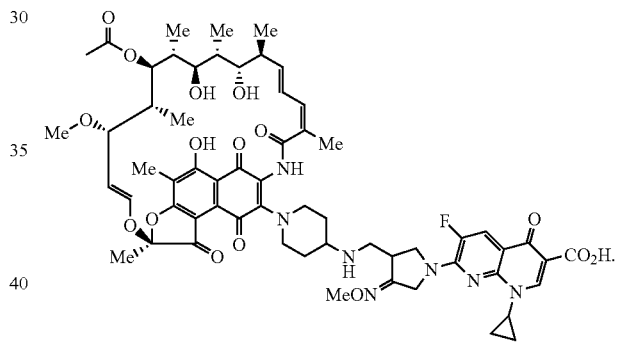

53. A compound of the formula: 3-[2-[3-Carboxy-1-(2,4-difluorophenyl)-6-fluoro-4-oxo-1,4-dihydronaphthyridin-7-yl]-2,7-diaza-spiro[4.5]decyl]-7-yl]rifamycin S:

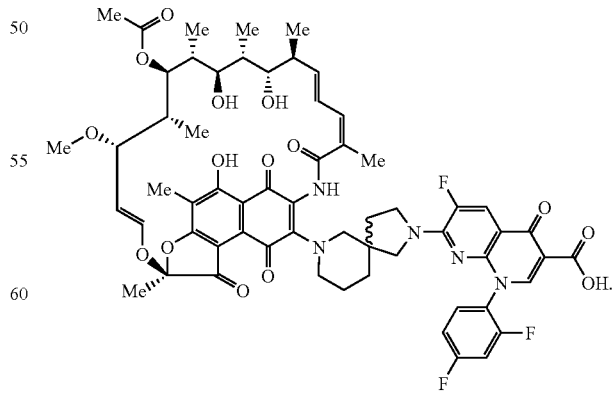

* * * * *